US012679848B2

(12) United States Patent
Bao et al.

(10) Patent No.: US 12,679,848 B2
(45) Date of Patent: Jul. 14, 2026

(54) PLASMA KALLIKREIN INHIBITORS

(71) Applicant: Merck Sharp & Dohme LLC, Rahway, NJ (US)

(72) Inventors: Jianming Bao, Princeton, NJ (US); Natalija Cernaka, Cupertino, CA (US); Alan C. Cheng, San Francisco, CA (US); Ying-Duo Gao, Middletown, NJ (US); Salman Jabri, Moraga, CA (US); Jovan Alexander Lopez, New Haven, CT (US); Rohan Merchant, Burlingame, CA (US); Anthony Ken Ogawa, San Mateo, CA (US); Skylar K. Osler, Pasadena, CA (US); Christopher J. Sinz, Walnut Creek, CA (US); Phillip Patrick Sharp, San Francisco, CA (US); Haiqun Tang, Belle Meade, NJ (US); Maoqun Tian, Forster, CA (US); Dong Xiao, Warren, NJ (US); Song Yang, San Francisco, CA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 562 days.

(21) Appl. No.: 18/252,261

(22) PCT Filed: Nov. 18, 2021

(86) PCT No.: PCT/US2021/059930
§ 371 (c)(1),
(2) Date: May 9, 2023

(87) PCT Pub. No.: WO2022/109161
PCT Pub. Date: May 27, 2022

(65) Prior Publication Data

US 2024/0025917 A1 Jan. 25, 2024

Related U.S. Application Data

(60) Provisional application No. 63/115,890, filed on Nov. 19, 2020.

(51) Int. Cl.
*C07D 498/10* (2006.01)

(52) U.S. Cl.
CPC .................................. *C07D 498/10* (2013.01)

(58) Field of Classification Search
CPC .................................................. C07D 498/10
USPC ......................................................... 514/230
See application file for complete search history.

(56) References Cited

U.S. PATENT DOCUMENTS

| | | | |
|---|---|---|---|
| 2008/0161373 A1 | 7/2008 | Pinto et al. | |
| 2017/0044183 A1 | 2/2017 | Lim et al. | |
| 2018/0311250 A1 | 11/2018 | Ali et al. | |

FOREIGN PATENT DOCUMENTS

| | | | | |
|---|---|---|---|---|
| JP | 2016519096 A | 6/2016 | | |
| JP | 2019507167 A | 3/2019 | | |
| RU | 2607045 C2 | 1/2017 | | |
| RU | 2712621 C2 | 1/2020 | | |
| WO | 2010118208 A1 | 10/2010 | | |
| WO | 2013005045 A1 | 1/2013 | | |
| WO | 2014160668 A1 | 10/2014 | | |
| WO | 2014188211 A1 | 11/2014 | | |
| WO | WO-2017074833 A1 * | 5/2017 | ................ | A61P 7/00 |
| WO | 2017151746 A1 | 9/2017 | | |

OTHER PUBLICATIONS

Bastin, R.J.; et al., Salt Selection and Optimization Procedures for Pharmaceutical New Chemical Entities, Organic Process Research and Development, 4, pp. 427-435, 2000.
Belikov, V.G., Pharmaceutical Chemistry, Moscow MEDpress-inform, 4th Edition, 27-29, 2007.
Dyson, G. and May, P., Chemistry of Synthetic Medicinal Substances, M: World, N/A, 12-19, 1964.
Kummerer, K., Pharmaceuticals in the environment, Annual Review of Environment and Resources, 35, 57-75, 2010.

(Continued)

*Primary Examiner* — Jeffrey H Murray
*Assistant Examiner* — Rilla Marie Samsell
(74) *Attorney, Agent, or Firm* — Daniel Woods; John C. Todaro

(57) ABSTRACT

The present invention provides a compound of Formula (I) and pharmaceutical compositions comprising one or more said compounds, and methods for using said compounds for treating or preventing one or more disease states that could benefit from inhibition of plasma kallikrein, including hereditary angioedema, uveitis, posterior uveitis, wet age related macular edema, diabetic macular edema, diabetic retinopathy and retinal vein occlusion. The compounds are selective inhibitors of plasma kallikrein.

(I)

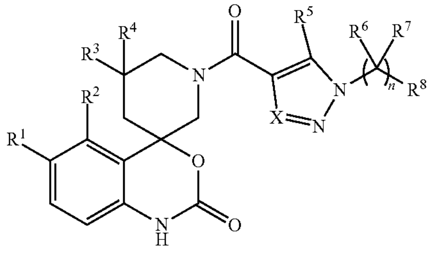

16 Claims, No Drawings

(56) References Cited

OTHER PUBLICATIONS

Chou, Ting-Chao et al., Quantitative Analysis of Dose-Effect Relationships: The Combined Effects of Multiple Drugs or Enzyme Inhibitors, Adv. Enzyme Regul., 1984, 27-55, 22.

Clermont, Allen et al., Plasma Kallikrein Mediates Retinal Vascular Dysfunction and Induces Retinal Thickening In Diabetic Rats, Diabetes, 2011, 1590-1598, 60.

Colman, Robert W., Contact Activation Pathway: Inflammatory, Fibrinolytic, Anticoagulant, Antiadhesive, and Antiangiogenic Activities, Hemostasis and Thrombosis, 2001, 103-121, Chapter 6.

Daiss, Jurgen, O. et al., Sila-venlafaxine, a Sila-Analogue of the Serotonin/Noradrenaline Reuptake Inhibitor Venlafaxine: Synthesis, Crystal Structure Analysis, and Pharmacological Characterization, Organometallics, 2006, pp. 1188-1198, vol. 25.

Nicolaou, K.C. et al., New Synthetic Technologies for the Construction of Heterocycles and Tryptamines, Journal of the American Chemical Society, 2009, 3690-3699, 131.

Schmaier, Alvin H., Contact Activation, Thrombosis and Hemorrhage, 1998, 105-127, Chapter 5.

Schneider, Lynda et al., Critical role of kallikrein in hereditary angioedema pathogenesis: A clinical trial of ecallantide, a novel kallikrein inhibitor, J Allergy Clin Immunol, 2007, 416-422, 120(2).

Showell, Graham, A. et al., (R)-Sila-venlafaxine: A selective noradrenaline reuptake inhibitor for the treatment of emesis, Bioorganic & Medicinal Chemistry Letters, 2006, pp. 2555-2558, vol. 16.

Bryant, J.W. et al., Human plasma kallikrein-kinin system: Physiological and biochemical parameters, Cardiovasc Hematol Agents Med Chem, 7(3), 234-250, 2009.

Dias, Jenny Pena et al., Kinin B1 Receptor Enhances the Oxidative Stress in a Rat Model of Insulin Resistance: Outcome in Hypertension, Allodynia and Metabolic Complications, PLoS ONE, vol. 5 | Issue 9 | e12622, 1-14, 2010.

Feener, Edward P. et al., Role of plasma kallikrein in diabetes and metabolism, Thromb Haemost, 110, 434-441, 2013.

Kita, Takeshi et al., Plasma Kallikrein-Kinin System as a VEGF-Independent Mediator of Diabetic Macular Edema, Diabetes, 64(10), 3588-3599, 2015.

Wang, Haidong et al., Bradykinin-bradykinin receptor (B1R) signalling is involved in the blood-brain barrier disruption in moyamoya disease, J Cell Mol Med, 27, 4069-4079, 2023.

Xie, Zhouling et al., Discovery and development of plasma kallikrein inhibitors for multiple diseases, European Journal of Medicinal Chemistry, 190: 112137, 1-14, 2020.

* cited by examiner

PLASMA KALLIKREIN INHIBITORS

CROSS-REFERENCE TO RELATED APPLICATIONS

This application is a National Stage application of International Patent Application No. PCT/US2021/059930, filed Nov. 18, 2021, which claims the benefit of priority to U.S. Provisional Patent Application No. 63/115,890, filed Nov. 19, 2020.

BACKGROUND OF THE INVENTION

Plasma kallikrein is a zymogen of a trypsin-like serine protease and is present in plasma. The gene structure is similar to that of factor XI. Overall, the amino acid sequence of plasma kallikrein has 58% homology to factor XI. Proteolytic activation by factor XIIa at an internal I 389-R390 bond yields a heavy chain (371 amino acids) and a light chain (248 amino acids). The active site of plasma kallikrein is contained in the light chain. The light chain of plasma kallikrein reacts with protease inhibitors, including alpha 2 macroglobulin and Cl-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R., "Contact Activation Pathway", Hemostasis and Thrombosis, pp. 103-122, Lippincott Williams & Wilkins (2001); Schmaier A. H., "Contact Activation", Thrombosis and Hemorrhage, pp. 105-128 (1998)).

Patients presenting genetic deficiency on Cl-esterase inhibitor suffer from hereditary angioedema (HAE), a lifelong disease that results in intermittent swelling throughout the body, including the hands, feet, face, throat, genitals and gastrointestinal tract. Analysis of blisters arising from acute episodes have been shown to contain high levels of plasma kallikrein, and treatment with a protein-based reversible plasma kallikrein inhibitor, Ecallantide (Kalbitor), has been approved by the FDA for the treatment of acute attacks of HAE (Schneider, L, et al., J. Allergy Clin. Immunol., 120: p. 416 (2007)).

Additionally, the plasma kallikrein-kinin system is abnormally abundant in patients diagnosed with advanced diabetic macular edema (DME). Recent publications have shown that plasma kallikrein contributes to observed retinal vascular leakage and dysfunction in diabetic rodent models (A. Clermont, et al., Diabetes, 60:1590 (2011)), and that treatment with a small molecule plasma kallikrein inhibitor ameliorated the observed retinal vascular permeability and other abnormalities related to retinal blood flow.

It would be desirable in the art to develop plasma kallikrein inhibitors having utility to treat a wide range of disorders, including hereditary angioedema, diabetic macular edema and diabetic retinopathy.

SUMMARY OF THE INVENTION

The present invention relates to compounds of Formula I:

I

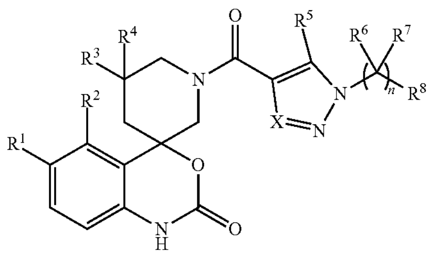

and pharmaceutically acceptable salts thereof. The compounds of Formula I are inhibitors of plasma kallikrein, and as such may be useful in the treatment, inhibition or amelioration of one or more disease states that could benefit from inhibition of plasma kallikrein, including hereditary angioedema, uveitis, posterior uveitis, wet age related macular edema, diabetic macular edema, diabetic retinopathy and retinal vein occlusion. The compounds of this invention could further be used in combination with other therapeutically effective agents, including but not limited to, other drugs useful for the treatment of hereditary angioedema, uveitis, posterior uveitis, wet age related macular edema, diabetic macular edema, diabetic retinopathy and retinal vein occlusion. The invention furthermore relates to processes for preparing compounds of Formula I, and pharmaceutical compositions which comprise compounds of Formula I and pharmaceutically acceptable salts thereof.

DETAILED DESCRIPTION OF THE INVENTION

The Present Invention Relates to Compounds of Formula I:

I

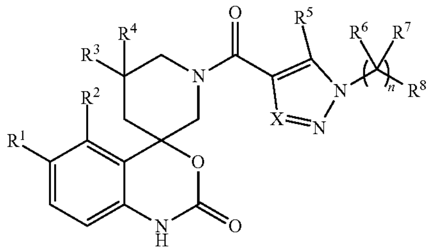

wherein X is N or CH;

$R^1$ is selected from the group consisting of hydrogen, halo, hydroxy and $C_{1-6}$ alkyl;

$R^2$ is selected from the group consisting of hydrogen, halo, hydroxy and $C_{1-6}$ alkyl;

$R^3$ is selected from the group consisting of hydrogen, halo, hydroxy and $C_{1-6}$ alkyl, wherein said alkyl group is optionally substituted with one to four substituents independently selected from the group consisting of halo, cyano and $OR^x$;

$R^4$ is selected from the group consisting of hydrogen, halo, hydroxy and $C_{1-6}$ alkyl; wherein said alkyl group is optionally substituted with one to four substituents independently selected from the group consisting of halo, cyano and $OR^x$;

$R^5$ is $NR^9R^{10}$ or $OR^x$;

each $R^6$ is independently selected from the group consisting of hydrogen, halo, hydroxy and $C_{1-6}$ alkyl, wherein said alkyl group is optionally substituted with one to three halo;

each $R^7$ is selected from the group consisting of hydrogen, halo, hydroxy and $C_{1-6}$ alkyl, wherein said alkyl group is optionally substituted with one to three halo;

or $R^6$ and $R^7$ can be taken together with the carbon atom to which they are attached to form a 3-6 membered cycloalkyl group, which is optionally substituted with one or two halo;

$R^8$ is selected from the group consisting of hydrogen; halo; hydroxy; $R^x$; $OR^x$; phenyl; indane; $OR^y$; heteroaryl, which can be monocyclic or bicyclic; heterocyclyl; and $C_{3-6}$ cycloalkyl, which can be monocyclic or bicyclic; wherein said phenyl and heteroaryl groups are optionally substituted with one to three substituents independently selected from the group consisting of oxo, halo, $R^x$, $OR^x$, $NR^9R^{10}$, $NR^9$ (C═O)$R^x$, $NR^9$ (C═O)$OR^x$, (C═O)$OR^x$, (C═O)$NR^9$, $R^y$ and $OR^y$; wherein said cycloalkyl and heterocyclyl groups are optionally substituted with one to three substituents independently selected from the group consisting of oxo, halo, $R^x$ and $OR^x$;

$R^9$ is hydrogen or $C_{1-3}$ alkyl;

$R^{10}$ is hydrogen or $C_{1-3}$ alkyl;

$R^x$ is hydrogen or $C_{1-6}$ alkyl, which is optionally substituted with one to three substituents selected from the group consisting of halo and hydroxy, $R^y$ is phenyl, heterocyclyl or $C_{3-6}$ cycloalkyl, wherein said phenyl group is optionally substituted with one to three halo, said heterocyclyl group is optionally substituted with one or two oxo and said cycloalkyl group is optionally substituted with $C_{1-6}$ alkyl;

n is an integer from zero to two;

or a pharmaceutically acceptable salt thereof.

In an embodiment of the invention, X is CH. In another embodiment of the invention, X is N.

In an embodiment of the invention, $R^1$ is halo. In a class of the embodiment, $R^1$ is chloro.

In an embodiment of the invention, $R^2$ is halo. In a class of the invention, $R^2$ is fluoro.

In an embodiment of the invention, $R^3$ is hydrogen. In another embodiment of the invention, $R^3$ is methyl.

In an embodiment of the invention, $R^4$ is hydrogen. In another embodiment of the invention, $R^3$ is methyl.

In an embodiment of the invention, $R^5$ is $NH_2$. In another embodiment of the invention, $R^5$ is OH.

In an embodiment of the invention, $R^6$ is hydrogen.

In an embodiment of the invention, $R^7$ is hydrogen.

In an embodiment of the invention, $R^8$ is phenyl; wherein said phenyl is optionally substituted with one to three substituents independently selected from the group consisting of halo, $R^x$, $OR^x$, $NR^9R^{10}$, $NR^9$(C═O)$R^x$, $NR^9$(C═O)$OR^x$, (C═O)$NR^9$, (C═O)$OR^x$, $R^y$ and $OR^y$. In a class of the embodiment, $R^8$ is phenyl; wherein said phenyl is optionally substituted with one to three substituents independently selected from the group consisting of halo, $R^x$, $OR^x$, $R^y$ and $OR^y$.

In an embodiment of the invention, n is zero. In another embodiment of the invention, n is one. In another embodiment of the invention, n is two.

Reference to the preferred classes and subclasses set forth above is meant to include all combinations of particular and preferred groups unless stated otherwise.

Specific embodiments of the present invention include, but are not limited to the compounds identified herein as Examples 1 to 133, or pharmaceutically acceptable salts thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention includes compositions for treating diseases or condition in which plasma kallikrein activity is implicated. Accordingly the invention includes compositions for treating impaired visual activity, diabetic retinopathy, diabetic macular edema, retinal vein occlusion, hereditary angioedema, diabetes, pancreatitis, cerebral hemorrhage, nephropathy, cardiomyopathy, neuropathy, inflammatory bowel disease, arthritis, inflammation, septic shock, hypotension, cancer, adult respiratory distress syndrome, disseminated intravascular coagulation, blood coagulation during cardiopulmonary bypass surgery, and bleeding from postoperative surgery in a mammal, comprising a compound of the invention in a pharmaceutically acceptable carrier. A class of the invention includes compositions for treating hereditary angioedema, uveitis, posterior uveitis, wet age related macular edema, diabetic macular edema, diabetic retinopathy and retinal vein occlusion. These compositions may optionally include anti-inflammatory agents, anti-VEGF agents, immunosuppressive agents, anticoagulants, antiplatelet agents, and thrombolytic agents. The compositions can be added to blood, blood products, or mammalian organs in order to effect the desired inhibitions.

The invention also includes compositions for preventing or treating retinal vascular permeability associated with diabetic retinopathy and diabetic macular edema in a mammal, comprising a compound of the invention in a pharmaceutically acceptable carrier. These compositions may optionally include anti-inflammatory agents, anti-VEGF agents, immunosuppressive agents, anticoagulants, antiplatelet agents, and thrombolytic agents.

The invention also includes compositions for treating inflammatory conditions of the eye, which includes, but is not limited to, uveitis, posterior uveitis, macular edema, acute macular degeneration, wet age related macular edema, retinal detachments, retinal vein occlusion, ocular tumors, fungal infections, viral infections, multifocal choroiditis, diabetic uveitis, diabetic macular edema, diabetic retinopathy, proliferative vitreoretinopathy, sympathetic opthalmia, Vogt Koyanagi-Harada syndrome, histoplasmosis and uveal diffusion. These compositions may optionally include anti-inflammatory agents, anti-VEGF agents, immunosuppressive agents, anticoagulants, antiplatelet agents, and thrombolytic agents.

The invention also includes compositions treating posterior eye disease, which includes, but is not limited to, uveitis, posterior uveitis, wet age related macular edema, diabetic macular edema, diabetic retinopathy and retinal vein occlusion. These compositions may optionally include anti-inflammatory agents, anti-VEGF agents, immunosuppressive agents, anticoagulants, antiplatelet agents, and thrombolytic agents.

It will be understood that the invention is directed to the compounds of structural Formula I described herein, as well as the pharmaceutically acceptable salts of the compounds of structural Formula I and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfamate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undecenate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, manganous, potassium, sodium, zinc, and the like. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

If the compounds of Formula I simultaneously contain acidic and basic groups in the molecule the invention also includes, in addition to the salt forms mentioned, inner salts or betaines (zwitterions).

The present invention encompasses all stereoisomeric forms of the compounds of Formula I. Unless a specific stereochemistry is indicated, the present invention is meant to comprehend all such isomeric forms of these compounds. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both each individual enantiomer and mixtures thereof, are embraced within the Formula. When a particular configuration is depicted, that entantiomer (either (R) or (S), at that center) is intended. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

Unless a specific enantiomer or diastereomer is indicated, the invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($1_H$) and deuterium ($2_H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable (e.g. $R^x$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted herein, the terms "alkyl" and "alkylene" are intended to include both branched- and straight-chain saturated aliphatic hydrocarbon groups having the specified number of carbon atoms. Commonly used abbreviations for alkyl groups are used throughout the specification, e.g. methyl, may be represented by conventional abbreviations including "Me" or $CH_3$ or a symbol that is an extended bond as the terminal group, e.g.

“  ”, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_{1-4}$ alkyl") for example, means linear or branched chain alkyl groups, including all isomers, having the specified number of carbon atoms. For example, the structures

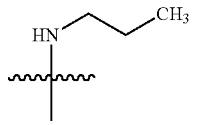

and

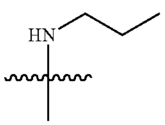

have equivalent meanings. $C_{1-4}$ alkyl includes n-, iso-, sec- and t-butyl, n- and isopropyl, ethyl and methyl. If no number is specified, 1-4 carbon atoms are intended for linear or branched alkyl groups.

Except where noted, the term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, and so on.

Except where noted, the term "aryl", as used herein, represents a stable monocyclic or bicyclic ring system of up to 10 carbon atoms in each ring, wherein at least one ring is aromatic. Bicyclic aryl ring systems include fused ring systems, where two rings share two atoms, and spiro ring systems, where two rings share one atom. Aryl groups within the scope of this definition include, but are not limited to: phenyl, indene, isoindene, naphthalene, and tetralin.

Except where noted, the term "heteroaryl", as used herein, represents a stable monocyclic or bicyclic ring system of up to 10 atoms in each ring, wherein at least one ring is aromatic, and at least one ring contains from 1 to 4 heteroatoms selected from the group consisting of O, N and S. Bicyclic heteroaryl ring systems include fused ring systems, where two rings share two atoms, and spiro ring systems, where two rings share one atom. Heteroaryl groups within the scope of this definition include but are not limited to: azaindolyl, benzoimidazolyl, benzisoxazolyl, benzofuranyl, benzofurazanyl, benzopyrazolyl, benzotriazolyl, benzothiophenyl, benzoxazolyl, carbazolyl, carbolinyl, cinnolinyl, dihydroindenyl, furanyl, indolinyl, indolyl, indolazinyl, indazolyl, isobenzofuranyl, isoindolyl, isoquinolyl, isothiazolyl, isoxazolyl, naphthalenyl, naphthpyridinyl, oxadiazolyl, oxazolyl, oxazoline, isoxazoline, pyranyl, pyrazinyl, pyrazolyl, pyrazolopyrimidinyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, dihydrobenzodioxinyl, dihydropyrazoloxazinyl, dihydropyrazolyothiazinedioxidyl, methylenedioxybenzene, benzothiazolyl, benzothienyl, quinolinyl, isoquinolinyl, oxazolyl, tetra-hydroquinoline, sulfolanyl, 1,3-benzodioxolyl, and 3-oxo-3,4dihydro-2N-benzo[b][1,4]thiazine. If the heteroaryl contains nitrogen atoms, it is understood that the corresponding N-oxides thereof are also encompassed by this definition.

The term "heterocycle" or "heterocyclyl" as used herein is intended to mean a stable nonaromatic monocyclic or bicyclic ring system of up to 10 atoms in each ring, unless otherwise specified, containing from 1 to 4 heteroatoms selected from the group consisting of O, N, S, SO, or $SO_2$. Bicyclic heterocyclic ring systems include fused ring systems, where two rings share two atoms, and spiro ring systems, where two rings share one atom. "Heterocyclyl" therefore includes, but is not limited to the following: azaspirononanyl, azaspirooctanyl, azetidinyl, dioxanyl, oxadiazaspirodecenyl, oxaspirooctanyl, oxazolidinonyl, piperazinyl, piperidinyl, pyrrolidinyl, morpholinyl, thiomorpholinyl, tetrahydrofuranyl, tetrahydropyranyl, dihydropiperidinyl, tetrahydrothiophenyl and the like. If the heterocycle contains a nitrogen, it is understood that the corresponding N-oxides thereof are also encompassed by this definition.

Except where noted, the term "halogen" or "halo" means fluorine, chlorine, bromine or iodine.

"Celite®" (Fluka) diatomite is diatomaceous earth, and can be referred to as "celite".

Except where noted herein, structures containing substituent variables such as variable "R" below:

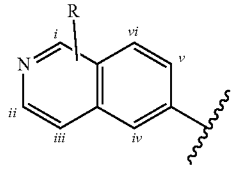

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also relates to medicaments containing at least one compound of the Formula I and/or of a pharmaceutically acceptable salt of the compound of the Formula I and/or an optionally stereoisomeric form of the compound of the Formula I or a pharmaceutically acceptable salt of the stereoisomeric form of the compound of Formula I, together with a pharmaceutically suitable and pharmaceutically acceptable vehicle, additive and/or other active substances and auxiliaries.

The term "patient" used herein is taken to mean mammals such as primates, humans, sheep, horses, cattle, pigs, dogs, cats, rats, and mice.

The medicaments according to the invention can be administered by oral, inhalative, rectal or transdermal administration or by subcutaneous, intraarticular, intraperitoneal or intravenous injection. Oral administration is preferred. Coating of stents with compounds of the Formulas I and other surfaces which come into contact with blood in the body is possible.

The invention also relates to a process for the production of a medicament, which comprises bringing at least one compound of the Formula I into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the plasma kallikrein inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the plasma kallikrein inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the plasma kallikrein inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of Formula I can be administered both as a monotherapy and in combination with other therapeutic agents, including but not limited to anti-inflammatory agents, anti-VEGF agents, immunosuppressive agents, anticoagulants, antiplatelet agents, and thrombolytic agents.

An "anti-inflammatory agent" is any agent which is directly or indirectly effective in the reduction of inflammation when administered at a therapeutically effective level. "Anti-inflammatory agent" includes, but is not limited to steroidal anti-inflammatory agents and glucocorticoids. Suitable anti-inflammatory agents include, but are not limited to, cortisone, dexamethasone, hydrocortisone, methylprednisolone, prednisolone, prednisone and triamcinolone.

An "anti-VEGF agent" is any agent which is directly or indirectly effective in inhibiting the activity of VEGF (Vascular Endothelial Growth Factor). Suitable anti-VEGF agents include, but are not limited to, bevacizumab, ranibizumab and aflibercept.

An "immunosuppressant agent" is any agent which is directly or indirectly effective in suppressing, or reducing, the strength of the body's immune system. Suitable immunosuppressant agents include, but are not limited to, corticosteroids (for example, prednisone, budesonide, prednisolone), janus kinase inhibitors (for example, tofacitinib), calcineurin inhibitors (for example, cyclosporin, tacrolimus), mTOR inhibitors (for example, sirolimus, everolimus), IMDH inhibitors (for example, azathioprine, leflunomide, mycophenolate), biologics (for example, abatacept, adalimumab, anakinra, certolizumab, etanercept, golimumab, infliximab, ixekizumab, natalizumab, rituximab, secukinumab, tocilizumab, ustekinumab, vedolizumab), and monoclonal antibodies (for example, basiliximab, daclizumab).

Suitable anticoagulants include, but are not limited to, factor XIa inhibitors, thrombin inhibitors, thrombin receptor antagonists, factor VIIa inhibitors, factor Xa inhibitors, factor IXa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors.

In certain embodiments the anti-inflammatory agents, anti-VEGF agents, immunosuppressant agents, anticoagulants, antiplatelet agents, and thrombolytic agents described herein are employed in their conventional dosage ranges and regimens as reported in the art, including, for example, the dosages described in editions of the *Physicians' Desk Reference*, such as the 70th edition (2016) and earlier editions. In other embodiments, the anti-inflammatory agents, anti-VEGF agents, immunosuppressant agents, anticoagulants, antiplatelet agents, and thrombolytic agents described herein are employed in lower than their conventional dosage ranges.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g., olmesartan medoxomil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, eplerenone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprikalim, loprazolam); sympatholytics; beta-adrenergic blocking drugs (e.g., acebutolol, atenolol, betaxolol, bisoprolol, carvedilol, metoprolol, metoprolol tartrate, nadolol, propranolol, sotalol, timolol); alpha adrenergic blocking drugs (e.g., doxazosin, prazosin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; inhibitors of glucose uptake, such as sodium-glucose transporter (SGLT) inhibitors and its various isoforms, such as SGLT-1, SGLT-2 (e.g., ASP-1941, TS-071, BI-10773, tofogliflozin, LX-4211, canagliflozin, dapagliflozin, ertugliflozin, ipragliflozin, remogliflozin and sotagliflozin), and SGLT-3; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of the plasma kallikrein inhibitors of the invention in combination with other suitable agents may be the same as those doses of plasma kallikrein inhibitors administered without coadministration of additional agents, or may be substantially less that those doses of plasma kallikrein inhibitors administered without coadministration of additional agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e., prevent, inhibit or ameliorate) the disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of each of the compounds when administered individually as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. The administration of each component does not need to be via the same route of administration; for example, one component can be administered orally, and another can be delivered into the vitreous of the eye.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

General Methods

Compounds of the present invention may be prepared using conventional techniques or according to the methodology outlined in the following general synthetic schemes. One skilled in the art can vary the procedures and reagents shown to arrive at similar intermediates and/or final compounds.

NMR spectra were measured on VARIAN or Bruker NMR Systems (400, 500 or 600 MHz). Chemical shifts are reported in ppm downfield and up field from tetramethylsilane (TMS) and referenced to either internal TMS or solvent resonances ($^1H$ NMR: δ 7.27 for $CDCl_3$, δ 2.50 for $(CD_3)(CHD_2)SO$, and $^{13}C$ NMR: δ 77.02 for $CDCl_3$, δ 39.51 for $(CD_3)_2SO$. Coupling constants (J) are expressed in hertz (Hz), and spin multiplicities are given as s (singlet), d (doublet), dd (double doublet), t (triplet), m (multiplet), and br (broad). Chiral resolutions were performed on either Waters Thar 80 SFC or Berger MG II preparative SFC systems. LC-MS data were recorded on SHIMADZU LC-MS-2020, SHIMADZU LC-MS-2010, or Agilent 1100 series LC-MS, Agilent Prime-1260, or Waters Acquity LC-MS instruments using C18 columns employing a MeCN gradient in water containing 0.02 to 0.1% TFA. UV detections were at 220 and/or 254 nm and ESI ionization was used for MS detection.

When chiral resolution was achieved by chromatography using chiral columns, the chiral columns used for SFC chiral resolutions are listed in tables. Some of the chiral columns used were CHIRALPAK AD, CHIRALCEL OJ, CHIRALPAK AS, CHIRALPAK AY, CHIRALPAK IA, CHIRALPAK AD-H, and CHIRALPAK AS-H. Henceforth, they will be referred by their two or three letter abbreviations. As a convention, the fast-eluting isomer from a chiral resolution is always listed first in this table followed immediately by the slower-eluting isomer from the same resolution. If more than two isomers were separated, they will be always listed in the tables in order they were eluted, such as Peak 1 followed by Peak 2, Peak 3 and so on. A * symbol near a chiral center in a structure denotes that this chiral center was resolved by chiral resolution without its stereochemical configuration unambiguously determined.

Also, TLC is thin layer chromatography; UV is ultraviolet; W is watts; wt. % is percentage by weight; ×g is times gravity; $\alpha_D$ is the specific rotation of polarized light at 589 nm; ° C. is degrees Celsius; % w/v is percentage in weight of the former agent relative to the volume of the latter agent; Hz is hertz; cpm is counts per minute; $\delta_H$ is chemical shift; d is doublet; dd is doublet of doublets; MHz is megahertz; MS is mass spectrum, and a mass spectrum obtained by ES-MS may be denoted herein by "LC-MS"; m/z is mass to charge ratio; n is normal; N is normal; nm is nanometer; nM is nanomolar.

For purposes of this specification, the following abbreviations have the indicated meanings: $[Mes\text{-}Acr\text{-}Me]^+$ is 9-mesityl-10-methylacridinium tetrafluoroborate; X-PHOS Pd G2 is Chloro(2-dicyclohexylphosphino-2',4',6'-triisopropyl-1,1'-biphenyl)[2-(2'-amino-1,1'-biphenyl)]palladium (II).

Ac acetyl
ACN acetonitrile
AcOH acetic acid
aq. aqueous
Boc or BOC tert-butoxycarbonyl
br broad
Bu or $^n$Bu Butyl (normal)
Bz benzoyl
° C. degrees Celsius
calcd. calculated
δ chemical shift
d doublet
DAST (diethylamino)sulfur trifluoride
DBU 1,8-diazabicyclo[5.4.0]undec-7-ene
DCM dichloromethane
dd doublet of doublets
DIEA, DIPEA N,N-diisopropylethylamine or Hünig's base
DMF dimethylformamide
DMSO dimethyl sulfoxide
DPPA diphenylphosphoryl azide
dqd doublet of a quartet of doublets
DTT dithiothreitol
EDC 1-ethyl-3-(3-dimethylaminopropyl)carbodiimide
EDTA ethylenediamine tetraacetic acid
equiv. equivalent
ESI electrospray ionization
Et Ethyl
$Et_2O$ diethyl ether
EtOH Ethanol
EtOAc ethyl acetate
g Grams
GST glutathione S-transferase
h hour
HATU N,N,N,N-tetramethyl-O-(7-azabenzotriazol-1-yl) uronium hexafluorophosphate
HPLC high-performance liquid chromatography
Hz Hertz
IPA isopropanol
$^i$Pr isopropyl
J coupling constant
LC liquid chromatography
LCMS liquid chromatography mass spectrometry
LED light emitting diode
m multiplet
M molar
Me methyl
MeOH methanol
mg milligrams
MHz megahertz
min minute
μL microliters
mL milliliters
mM millimolar
mmol millimoles
MS mass spectrometry
MTBE methyl tert-butyl ether
N nitrogen substituted
nm nanometer
nM nanomolar
NMP 1-methylpyrrolidinone
NMR nuclear magnetic resonance spectroscopy
OAc acetate
Ph phenyl Pr propyl
q quartet
rac racemic mixture
RT or rt room temperature (ambient, about 25° C.)
s singlet
satd. saturated
SFC supercritical fluid chromatography
t triplet
T3P propanephosphonic acid anhydride
TBAF tert-butyl ammonium fluoride
TBS or TBDMS tert-butyldimethyl silyl
TBSCl tert-butyldimethylsilyl chloride
$^t$Bu tert-butyl
$^t$BuOH tert-butyl alcohol
TCFH tetramethylchloroformamidinium hexafluorophosphate
TEA triethylamine ($Et_3N$)

| Chiral Column | Stationary Phase | Method |
|---|---|---|
| AD-H | 40% $EtOH/CO_2$ | A |
| IC | 20% $EtOH/CO_2$ | B |
| AD-H | 40% $MeOH/CO_2$ | C |
| AD-H | 40% $^i PrOH/CO_2$ | D |
| AD-H | 25% $^i PrOH/CO_2$ | E |
| AD-H | 35% $^i PrOH/CO_2$ | F |
| OD-H | 20% $EtOH/CO_2$ | G |
| AS-H | 20% $EtOH/CO_2$ | H |
| IC | 25% $^i PrOH/CO_2$ | I |
| OJ-H | 30% $EtOH/CO_2$ | J |

General Schemes

Scheme A.

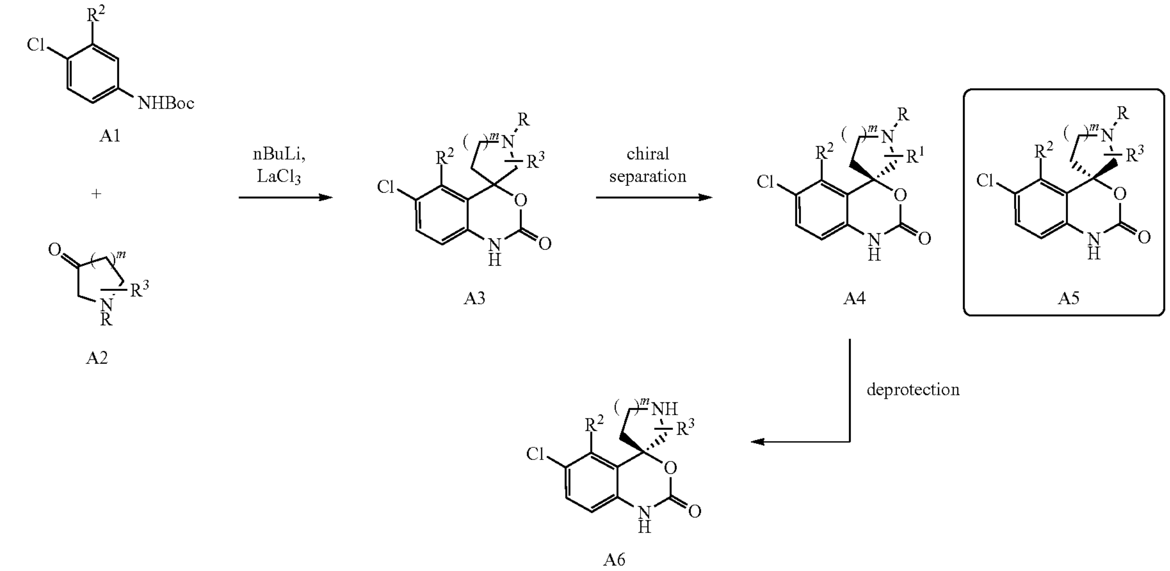

A1 A2 A3 A4 A5 A6 m = 1 or 2
R is any suitable (protecting) group tert tertiary
TFA trifluoroacetic acid
THF tetrahydrofuran
TLC thin layer chromatography
TMS trimethylsilyl
TMSCl chlorotrimethylsilane
Tris tris(hydroxymethyl)aminomethane
Ts toluenesulfonyl (tolyl)
tt triplet of triplets
X-phos or X-2-dicyclohexylphosphino-2',4',6'
PHOS triisopropylbiphenyl General Methods Starting materials used were obtained from commercial sources or prepared in other examples, unless otherwise noted. The methods used for the preparation of the compounds of this invention are illustrated by the following schemes. Unless specified otherwise, all starting materials used are commercially available.

Chiral Separation Methods

The general preparative conditions for separating diastereomeric or enantiomeric mixtures of compounds using chiral SFC are as follows:

Scheme A illustrates the synthetic sequence for preparation of substituted spirocarbamates such as A6 from Boc-protected aniline A1 and ketones such as A2. Directed lithiation of aniline A1 and addition into the heterocyclic ketone A2 occurs in the presence of Lewis acid (eg. $LaCl_3$). The tertiary alcohol undergoes in situ cyclization onto the carbamate to give spirocarbamate derivatives such as A3, which can be subjected to chiral separation, preferably using supercritical flow chromatography (SFC) to afford enantiomers A4 and A5. Deprotection of either enantiomer (A4, e.g.) gives the secondary amine A6.

Scheme B.

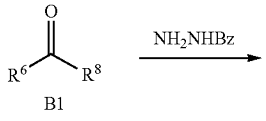

B1

-continued

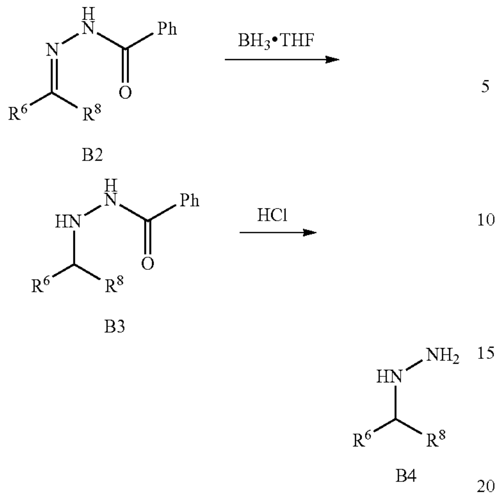

B2

B3

B4

Scheme B illustrates the synthetic sequence for preparation of alkyl hydrazines such as B4 from carbonyl derivatives such as B1. Condensation of carbonyl B1 with benzohydrazide gives intermediate B2 which is reduced to the protected hydrazine B3. Deprotection under acidic conditions gives the alkyl hydrazine B4.

Scheme C.

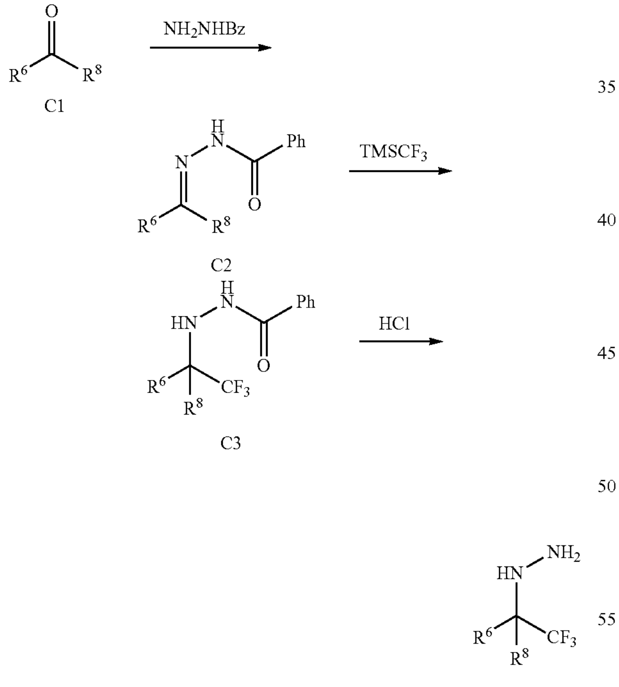

C1

C2

C3

C4

Scheme C illustrates the synthetic sequence for preparation of $CF_3$ ethyl hydrazine derivatives such as C4 from carbonyl derivatives such as C1. Condensation of carbonyl C1 with benzohydrazide gives intermediate C2. Addition of $CF_3$ with $TMSCF_3$ to C2 provides $CF_3$-ethyl intermediate C3 which is deprotected under acidic conditions to give the hydrazine derivatives C4.

Scheme D.

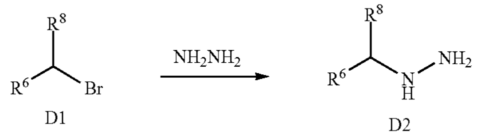

D1

D2

Scheme D illustrates the synthesis of alkyl hydrazines derivatives such as D2 from alkyl halides such as D1. Alkylation of hydrazine with alkyl halides D1 provides the alkyl hydrazines D2.

Scheme E.

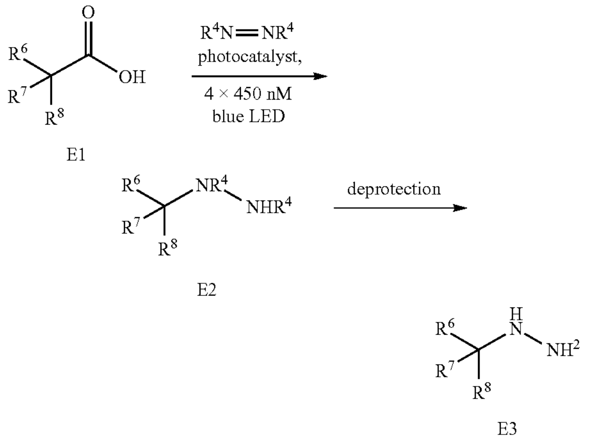

E1

E2

E3

Scheme E illustrates the synthetic sequence for preparation of alkyl hydrazine derivatives such as E3 from carboxylic acid derivatives such as E1. Photoredox decarboxylative hydrazidation of carboxylic acids E1 provides the protected hydrazine intermediate E2. Deprotection gives the alkyl hydrazine derivatives E3.

Scheme F.

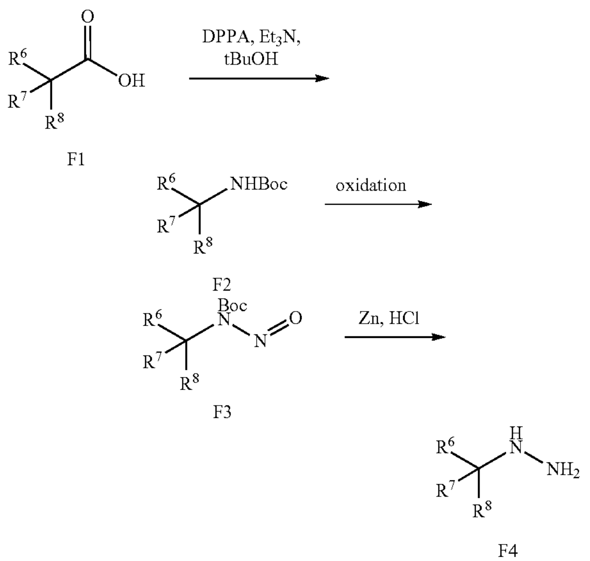

F1

F2

F3

F4

Scheme F illustrates the synthetic sequence for preparation of alkyl hydrazine derivatives such as F4 from alkyl carboxylic derivatives such as F1. Curtius rearrangement of alkyl carboxylic acid F1 gives protected amine F2. Oxidation of F2 provides the N-nitroso intermediate F3 which is reduced and deprotected to give the alkyl hydrazine derivatives F4.

Scheme G.

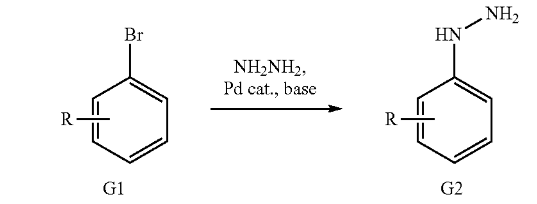

G1 G2

R is any suitable group, as defined within $R^8$ of compound I

Scheme G illustrates the synthesis of aryl hydrazines such as G2 from aryl bromides such as G1. Aryl hydrazines G2 are prepared via palladium-catalyzed cross-coupling reaction of aryl bromides such as G1 with hydrazine in the presence of suitable base.

Scheme H.

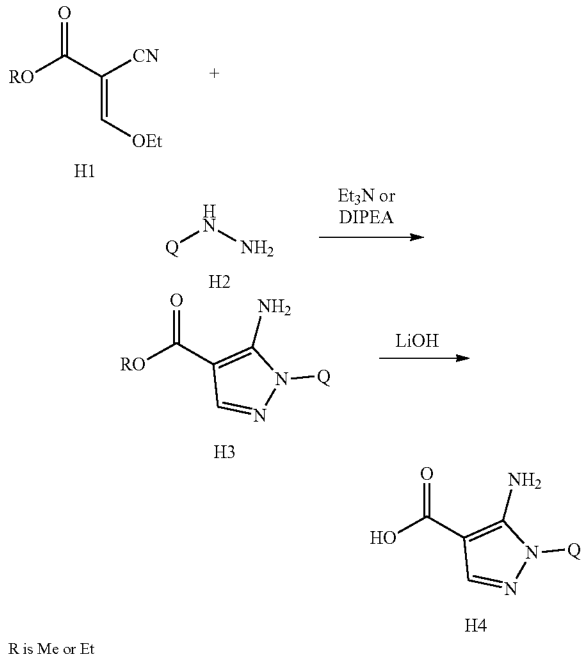

H1 H2 H3 H4

R is Me or Et
Q is any group as defined for compound I

Scheme H illustrates the synthetic sequence for preparation of aminopyrazole derivatives such as H4 from hydrazine derivatives such as H2 and cyano alkoxyacrylate H1. Condensation of substituted hydrazines H2 with cyano ethoxy acrylate H1 affords the ester aminopyrazole derivatives such as H3. Saponification of H3 gives the carboxylic acid H4.

Scheme I.

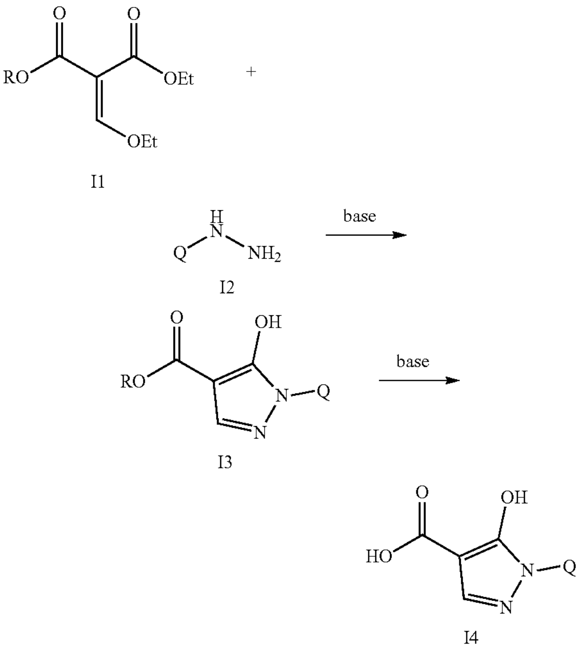

I1 I2 I3 I4

R is Me or Et
Q is any group as defined for compound I

Scheme I illustrates the synthetic sequence for preparation of hydroxypyrazole derivatives such as I4 from hydrazine derivatives such as I2 and alkoxymethylene malonate I1. Condensation of substituted hydrazines 12 with malonate I1 affords the ester hydroxypyrazole derivatives such as I3. Saponification of I3 gives the carboxylic acid I4.

Scheme J.

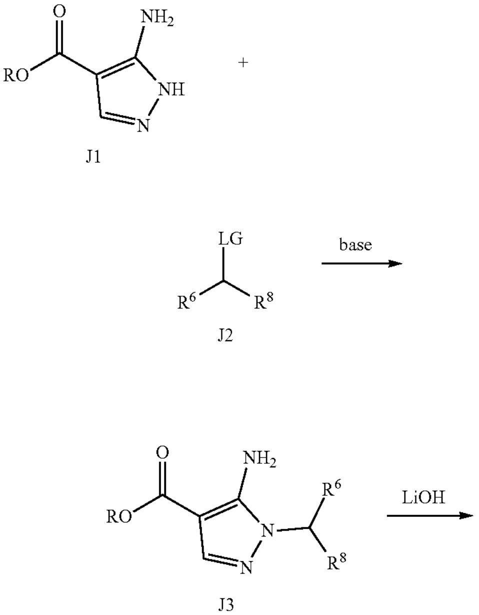

J1 J2 J3

-continued

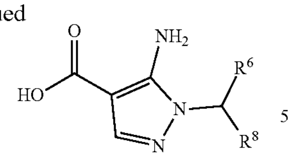

J4

R is Me or Et
LG is a suitable leaving group

Scheme J illustrates the synthetic sequence for preparation of N-substituted aminopyrazole derivatives such as J4 from unsubstituted aminopyrazole derivatives such as J1. Alkylation of aminopyrazole J1 provides the N-substituted aminopyrazole J3. Saponification of J3 provides the carboxylic acid of N-substituted aminopyrazole J4.

Scheme K.

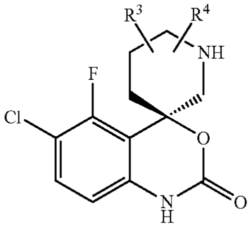

K1

-continued

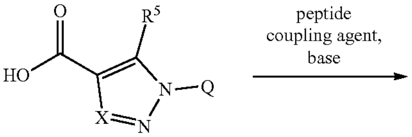

K2

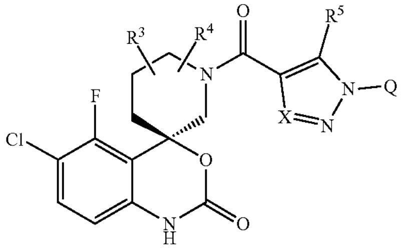

K3

Q is a group as defined for compound I

Scheme K illustrates the preparation of spirocarbamate pyrazole or triazole derivatives such as K1 from spirocarbamate piperidine derivatives such as K1 and carboxylic acid derivates such as K2. Coupling of carboxylic acid K2 with spirocarbamate K1 using peptide coupling agents such as TCFH, EDC, HATU or T3P provides the amide K3.

Scheme L.

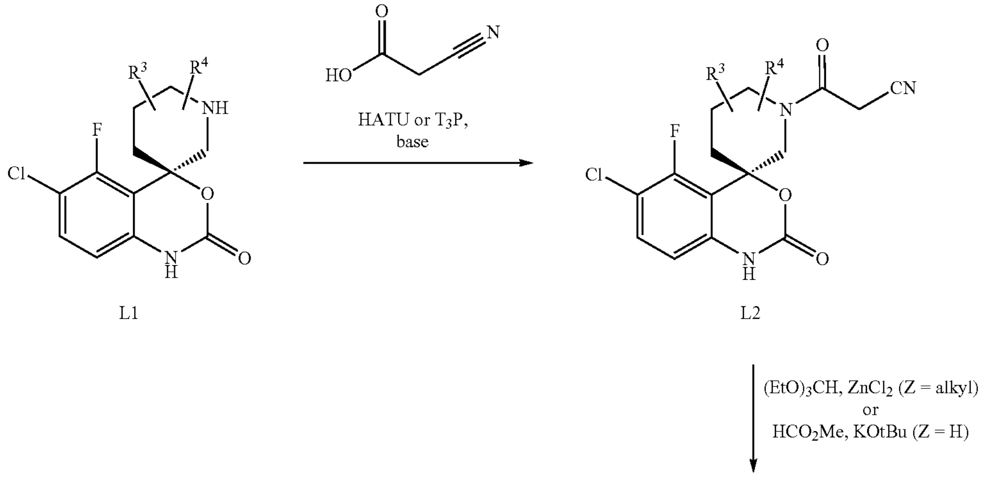

L1

L2

-continued

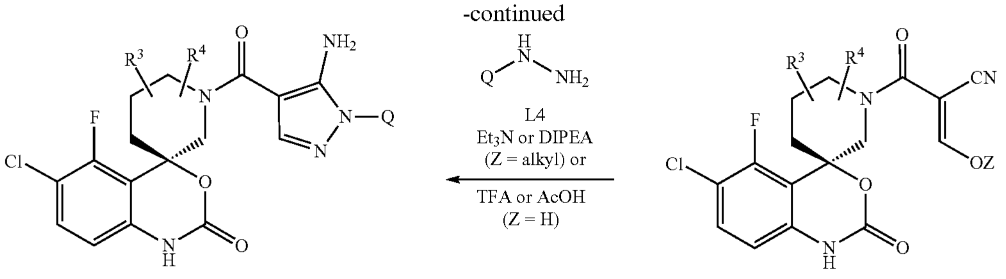

L5

L3

Q is a group as defined for compound I

Scheme L illustrates the synthetic sequence for the preparation of spirocarbamate aminopyrazole derivatives such as L5 from spirocarbamate piperidine derivatives such as L1. Coupling of spirocarbamate L1 with cyanoacetic acid provides intermediate L2 which undergoes condensation to give cyano acrylate derivates such as L3. Condensation of L3 with various hydrazines L4 under basic or acidic conditions provides aminopyrazoles such as L5.

Intermediate A2-1

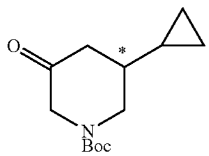 [SMILES: CC(C)(C)OC(=O)N1CC(=O)CC(C2CC2)C1]

Tert-butyl 3-cyclopropyl-5-oxopiperidine-1-carboxylate

Cyclopropylmagnesium bromide (30.0 mL, 15.2 mmol, 0.5 M in THF) was added at −78° C. to a suspension of CuI (1.45 g, 7.61 mmol) in THF (20 mL) under $N_2$ atmosphere. The resulting mixture was allowed to warm to 0° C. and stirred for an additional 1 h to generate the organocuprate reagent. The solution was then cooled to −78° C. followed by addition of a THF solution (5 mL) of tert-butyl 3-oxo-3,6-dihydropyridine-1(2H)-carboxylate (1.0 g, 5.1 mmol) and TMSCl (1.30 mL, 10.1 mmol). The reaction mixture was stirred at −78° C. for 1 h before quenching with MeOH. The mixture was diluted with EtOAc and satd. aq. $NH_4Cl$, and the layers separated. The organic layers were dried over $MgSO_4$, filtered and concentrated under reduced pressure. The crude residue was purified by silica gel chromatography to afford the title compound. $^1H$ NMR (600 MHz, $CDCl_3$) δ 4.12-3.74 (m, 3H), 3.18 (br s, 1H), 2.66 (dd, J=16.3, 4.6 Hz, 1H), 2.33 (dd, J=16.1, 10.5 Hz, 1H), 1.49 (s, 9H), 1.32-1.24 (m, 1H), 0.63 (tt, J=8.7, 4.7 Hz, 1H), 0.55 (dd, J=12.9, 5.3 Hz, 2H), 0.25 (s, 1H), 0.18-0.11 (m, 1H).

Intermediate A2-2

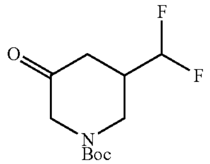 [SMILES: CC(C)(C)OC(=O)N1CC(=O)CC(C(F)F)C1]

tert-butyl 3-(difluoromethyl)-5-oxopiperidine-1-carboxylate

To a solution of tert-butyl 3-oxo-3,6-dihydropyridine-1(2H)-carboxylate (1.1 g, 5.6 mmol) and zinc difluoromethanesulfinate (2.5 g, 8.4 mmol) in trifluorotoluene (22 mL) and $H_2O$ (9 mL), tert-Butyl hydroperoxide (1.70 mL, 12.6 mmol, 70% wt/v in $H_2O$) was added dropwise at rt. The reaction mixture was heated to 35° C. and stirred for 12 h. Then, the flask was cooled to rt, diluted with $H_2O$ and DCM and the layers were separated. The combined organic layers were dried over $MgSO_4$, filtered and concentrated under reduced pressure. The crude residue was purified by silica gel chromatography (EtOAc:hexanes) to afford the title compound. $^1H$ NMR (600 MHz, $CDCl_3$) δ 5.80 (t, J=55.5 Hz, 1H), 4.12-3.72 (m, 3H), 3.50 (br s, 1H), 2.63 (dd, J=15.7, 5.3 Hz, 1H), 2.59-2.53 (m, 1H), 2.50 (dd, J=15.6, 8.7 Hz, 1H), 1.47 (s, 9H).

Intermediate A2-3

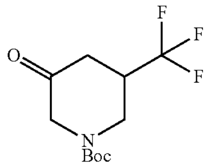 [SMILES: CC(C)(C)OC(=O)N1CC(=O)CC(C(F)(F)F)C1]

Tert-butyl 3-oxo-5-(trifluoromethyl)piperidine-1-carboxylate

To a solution of tert-butyl 3-hydroxy-5-(trifluoromethyl) piperidine-1-carboxylate (8.0 g, 29.7 mmol) in DCM (50 mL), $NaHCO_3$ (7.5 g, 89 mmol) and Dess-Martin Periodinane (15.1 g, 35.7 mmol) was added at rt. The reaction mixture was stirred at rt for 1 h. Then, the reaction was quenched with $H_2O$ and diluted with DCM. The layers were separated and the aq. phase was extracted with DCM. The combined organic layers were dried over $MgSO_4$, filtered and concentrated under reduced pressure. The crude residue was purified by silica gel chromatography (EtOAc:hexanes) to afford the title compound. $^1$H NMR (600 MHz, $CDCl_3$) δ 4.32-3.77 (m, 3H), 3.72-3.20 (m, 1H), 2.83 (d, J=6.9 Hz, 1H), 2.73 (dd, J=16.7, 6.1 Hz, 1H), 2.57 (dd, J=16.6, 9.4 Hz, 1H), 1.47 (s, 9H).

Intermediate A6-1

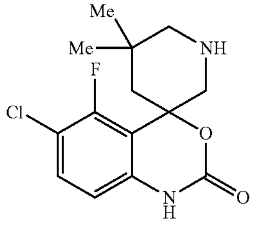 [SMILES: CC1(C)CNCC2(C1)OC(=O)Nc1ccc(Cl)c(F)c12]

6-Chloro-5-fluoro-5',5'-dimethylspiro[benzo[d][1,3]oxazine-4,3'-piperidin]-2(1H)-one Step 1: tert-Butyl 6-chloro-5-fluoro-5',5'-dimethyl-2-oxo-1,2-dihydrospiro[benzo[d][1,3]oxazine-4,3'-piperidine]-1'-carboxylate: THF (55 mL) was added to a round-bottom flask containing tert-butyl (4-chloro-3-fluorophenyl)carbamate (2.21 g, 9.0 mmol) under $N_2$ atmosphere, and the solution was cooled to −78° C. To the stirring solution, $^{n}$BuLi (11.2 mL, 27.9 mmol, 2.5 M in hexanes) was added over 40 minutes. The reaction mixture was allowed to stir at −78° C. for and additional 45 minutes, at which time, a solution of $LaCl_3$·2LiCl (22.5 mL, 13.5 mmol, 0.6 M in THF) and tert-butyl 3,3-dimethyl-5-oxopiperidine-1-carboxylate (3.10 g, 13.5 mmol) was added at −78° C. over a period of 40 minutes to the reaction mixture. The reaction mixture was allowed to warm to rt and stirred for 16 h. KO$^{t}$Bu (5.3 mL, 9.0 mmol, 1.7 M in THF) was added to the reaction mixture, and the solution was heated to 60° C. for an additional 3 h. The reaction was cooled to rt, quenched with 1 M HCl and diluted with EtOAc. The layers were separated and aq. phase was extracted with EtOAc. The combined organic layers were dried over $MgSO_4$, filtered and concentrated under reduced pressure. The crude residue was purified by silica gel chromatography (EtOAc:hexanes) to afford the title compound. LCMS [M+Na]$^+$=421.1 (calcd. 421.1).

Step 2: 6-Chloro-5-fluoro-5',5'-dimethylspiro[benzo[d][1,3]oxazine-4,3'-piperidin]-2(1H)-one HCl (25.0 mL, 100 mmol, 4 M in dioxane) was added to a round-bottom flask containing a suspension of tert-butyl 6-chloro-5-fluoro-5',5'-dimethyl-2-oxo-1,2-dihydrospiro[benzo[d][1,3]oxazine-4,3'-piperidine]-1'-carboxylate (7.98 g, 20.0 mmol) in 1,4-dioxane (30 mL). The reaction mixture was heated to 90° C. and stirred vigorously for 12 h. The reaction was cooled to rt and concentrated to give the crude title compound that was carried forward to the next step without further purification. LCMS [M+H]$^+$=299.1 (calcd. 299.1).

TABLE A

The following compounds were prepared using procedures similar to those described for Intermediate A6-1 using the appropriate starting materials.

| Intermediate | Structure | Name | LCMS [M + H]$^+$ |
|---|---|---|---|
| A6-2 | 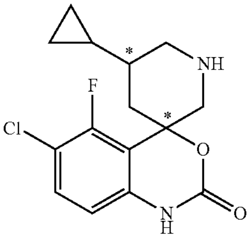 [SMILES: O=C1Nc2ccc(Cl)c(F)c2C2(CNCC(C3CC3)C2)O1] | (4R and S,5'S and R)-6-Chloro-5'-cyclopropyl-5-fluorospiro[benzo[d][1,3]oxazine-4,3'-piperidin]-2(1H)-one | Calcd. 311.1, found 311.0 |
| A6-3 | 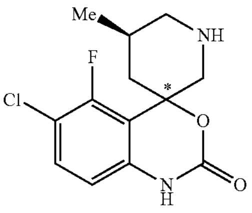 [SMILES: C[C@H]1CNCC2(C1)OC(=O)Nc1ccc(Cl)c(F)c12] | (4R and S,5'R)-6-Chloro-5-fluoro-5'-methylspiro[benzo[d][1,3]oxazine-4,3'-piperidin]-2(1H)-one | Calcd. 285.1, found 285.0 |

TABLE A-continued

The following compounds were prepared using procedures similar to those described for Intermediate A6-1 using the appropriate starting materials.

| Intermediate | Structure | Name | LCMS $[M + H]^+$ |
|---|---|---|---|
| A6-4 | 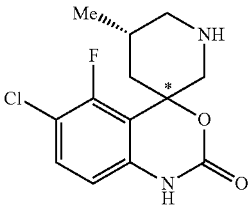 [SMILES: C[C@@H]1CNCC2(C1)OC(=O)Nc1ccc(Cl)c(F)c12] | (4R and S,5'S)-6-Chloro-5-fluoro-5'-methylspiro[benzo[d][1,3]oxazine-4,3'-piperidin]-2(1H)-one | Calcd. 311.0, found 311.0 |
| A6-5 | 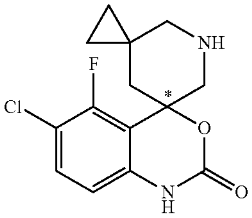 [SMILES: O=C1Nc2ccc(Cl)c(F)c2C2(CNCC3(CC3)C2)O1] | (R)- and (S)-6-Chloro-5-fluorodispiro[benzo[d][1,3]oxazine-4,3'-piperidine-5',1"-cyclopropan]-2(1H)-one | Calcd. 297.1, found 297.0 |
| A6-6 | 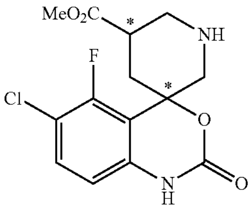 [SMILES: COC(=O)C1CNCC2(C1)OC(=O)Nc1ccc(Cl)c(F)c12] | Methyl (4R and S,5'S and R)-6-chloro-5-fluoro-2-oxo-1,2-dihydrospiro[benzo[d][1,3]oxazine-4,3'-piperidine]-5'-carboxylate | Calcd. 329.1, found 329.0 |
| A6-7 | 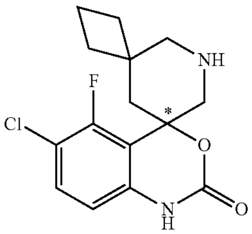 [SMILES: O=C1Nc2ccc(Cl)c(F)c2C2(CNCC3(CCC3)C2)O1] | (R)- and (S)-6-Chloro-5-fluorodispiro[benzo[d][1,3]oxazine-4,3'-piperidine-5',1"-cyclobutan]-2(1H)-one | Calcd. 311.1, found 311.0 |
| A6-8 | 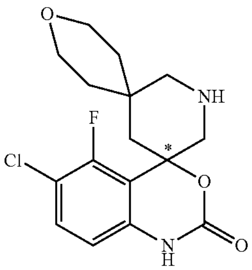 [SMILES: O=C1Nc2ccc(Cl)c(F)c2C2(CNCC3(CCOCC3)C2)O1] | (R)- and (S)-6-Chloro-5-fluoro-2",3",5",6"-tetrahydrodispiro[benzo[d][1,3]oxazine-4,3'-piperidine-5',4"-pyran]-2(1H)-one | Calcd. 341.1, found 341.0 |
| A6-9 | 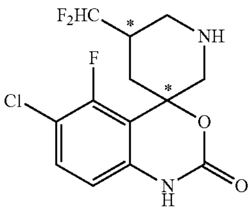 [SMILES: O=C1Nc2ccc(Cl)c(F)c2C2(CNCC(C(F)F)C2)O1] | (4R and S,5'S and R)-6-Chloro-5'-(difluoromethyl)-5-fluorospiro[benzo[d][1,3]oxazine-4,3'-piperidin]-2(1H)-one | Calcd. 321.1, found 321.0 |

TABLE A-continued

The following compounds were prepared using procedures similar to those described for Intermediate A6-1 using the appropriate starting materials.

| Intermediate | Structure | Name | LCMS $[M + H]^+$ |
|---|---|---|---|
| A6-10 | 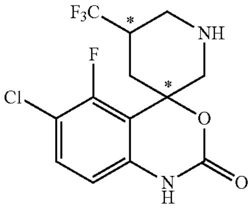 [SMILES: O=C1Nc2ccc(Cl)c(F)c2C2(CNCC(C(F)(F)F)C2)O1] | (4R and S,5'S and R)-6-Chloro-5-fluoro-5'-(trifluoromethyl)spiro[benzo[d][1,3]oxazine-4,3'-piperidin]-2(1H)-one, hydrogen salt | Calcd. 339.1, found 338.9 |
| A6-11 | 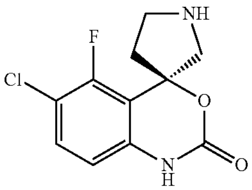 [SMILES: O=C1Nc2ccc(Cl)c(F)c2[C@@]2(CCNC2)O1] | (R)-6-chloro-5-fluorospiro[benzo[d][1,3]oxazine-4,3'-pyrrolidin]-2(1H)-one | Calcd. 257.1, found 257.0 |
| A6-12 | 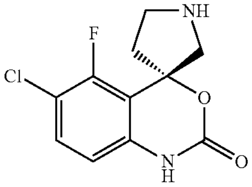 [SMILES: O=C1Nc2ccc(Cl)c(F)c2[C@]2(CCNC2)O1] | (S)-6-chloro-5-fluorospiro[benzo[d][1,3]oxazine-4,3'-pyrrolidin]-2(1H)-one | Calcd. 257.1, found 257.0 |
| A6-13 | 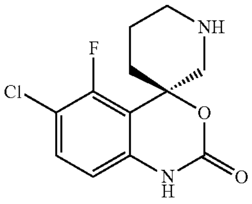 [SMILES: O=C1Nc2ccc(Cl)c(F)c2[C@@]2(CCCNC2)O1] | (R)-6-Chloro-5-fluorospiro[benzo[d][1,3]oxazine-4,3'-piperidin]-2(1H)-one | Calcd. 271.1, found 271.0 |
| A6-14 | 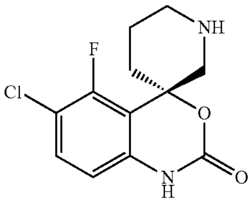 [SMILES: O=C1Nc2ccc(Cl)c(F)c2[C@]2(CCCNC2)O1] | (S)-6-Chloro-5-fluorospiro[benzo[d][1,3]oxazine-4,3'-piperidin]-2(1H)-one | Calcd. 271.1, found 271.0 |

Intermediate A6-15

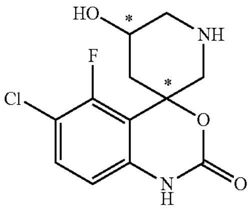 [SMILES: O=C1Nc2ccc(Cl)c(F)c2C2(CNCC(O)C2)O1]

(Rac)-tert-Butyl (4R or S,5'R or S)-6-chloro-5-fluoro-5'-hydroxy-2-oxo-1,2-dihydrospiro[benzo[d][1,3]oxazine-4,3'-piperidine]-1'-carboxylate Step 1: tert-Butyl 3-((tert-butyldimethylsilyl)oxy)-5-oxopiperidine-1-carboxylate: A flask containing a solution of tert-butyl 3-hydroxy-5-oxopiperidine-1-carboxylate (22.4 g, 104 mmol) in DMF (224 mL) was cooled to 0° C. Imidazole (21.2 g, 312 mmol) and TBSCl (18.8 g, 125 mmol) were added, and the reaction mixture was warmed to rt and stirred for 16 h. The reaction was quenched with $H_2O$ and extracted with MTBE. The layers were separated, and the combined organic layers washed with brine. The organic layer was dried over $Na_2SO_4$, filtered and concentrated to afford a crude residue that was purified by silica gel chromatography (EtOAc:petroleum ether) to afford the title compound. LCMS $[M-55]^+$=274.3 (calcd. 274.2).

Step 2: (rac)-tert-Butyl (4R or S,5'R or S)-5'-((tert-butyldimethylsilyl)oxy)-6-chloro-5-fluoro-2-oxo-1,2-dihydrospiro

[benzo[d][1,3]oxazine-4,3'-piperidine]-1'-carboxylate and (rac)-tert-butyl (4S or R, 5'S or R)-5'-((tert-butyldimethylsilyl)oxy)-6-chloro-5-fluoro-2-oxo-1,2-dihydrospiro[benzo[d][1,3]oxazine-4,3'-piperidine]-1'-carboxylate: THF (188 mL) was added to a round-bottom flask containing tert-butyl (4-chloro-3-fluorophenyl)carbamate (12.5 g, 50.9 mmol), and the mixture was cooled to −78° C. $^{n}$BuLi (63.1 mL, 158 mmol, 2.5 M in hexanes) was added over 1 h, followed by a solution of $LaCl_3 \cdot 2LiCl$ (×102 mL, 61.1 mmol, 0.6 M in THF) and tert-butyl 3-((tert-butyldimethylsilyl)oxy)-5-oxopiperidine-1-carboxylate (20.1 g, 61.1 mmol) that was added dropwise at −78° C. over 5 min. The reaction mixture was stirred at −78° C. for 1 h, and warmed to rt for an additional 12 h. The reaction was quenched with satd. aq. $NH_4Cl$, poured into a flask containing ice and stirred for 15 min. The mixture was diluted with EtOAc, the layers were separated and the combined organic layers dried over $MgSO_4$, filtered and concentrated to afford a crude residue that was purified by silica gel chromatography (EtOAc: petroleum ether) to afford the title compound as a mixture of diastereomers. The diasteromers were separated by preparative reverse phase HPLC (ACN/water+10 mM $NH_4HCO_3$). The faster eluting diastereomer of the title compound was obtained: LCMS $[M+Na]^+$=523.3 (calcd. 523.2). The slower eluting diastereomer of the title compound was obtained: LCMS $[M+Na]^+$=523.3 (calcd. 523.2).

Step 3: (rac)-(4R or S,5'R or S)-6-Chloro-5-fluoro-5'-hydroxyspiro[benzo[d][1,3]oxazine-4,3'-piperidin]-2(1H)-one: A flask containing (rac)-tert-butyl (4S or R,5'S or R)-5'-((tert-butyldimethylsilyl)oxy)-6-chloro-5-fluoro-2-oxo-1,2-dihydrospiro[benzo[d][1,3]oxazine-4,3'-piperidine]-1'-carboxylate (slower eluting peak from previous step, 1.0 g, 2.0 mmol) in THF (20 mL) was cooled to 0° C. TBAF (6.0 mL, 6.0 mmol) was added, and the reaction mixture was warmed to 40° C. for 12 h. The reaction was quenched with ice-water and stirred for 15 min. The mixture was diluted with EtOAc, the layers were separated, and the combined organic layers were washed with brine. The organic layer was dried over $MgSO_4$, filtered and concentrated under reduced pressure to afford the crude product that was carried forward without further purification. HCl (0.9 mL, 3.5 mmol, 4 M in dioxane) was added to a vial containing a suspension of crude product (34 mg, 0.090 mmol) in 1,4-dioxane (0.8 mL). The reaction mixture was stirred vigorously at rt for 12 h and concentrated to give the crude title compound. The crude product was carried forward to the next step without further purification. LCMS $[M+H]^+$=287.0 (calcd. 287.1).

Intermediate A6-16

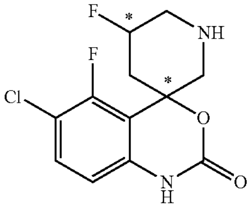 [SMILES: O=C1Nc2ccc(Cl)c(F)c2C2(CNCC(F)C2)O1]

(Rac)-(4R or S,5'R or S)-6-Chloro-5,5'-difluorospiro[benzo[d][1,3]oxazine-4,3'-piperidin]-2(1H)-one Step 1: (rac)-tert-Butyl (4R or S,5'R or S)-6-chloro-5,5'-difluoro-2-oxo-1,2-dihydrospiro[benzo[d][1,3]oxazine-4,3'-piperidine]-1'-carboxylate: A flask containing (rac)-tert-butyl (4S or R,5'S or R)-5'-((tert-butyldimethylsilyl)oxy)-6-chloro-5-fluoro-2-oxo-1,2-dihydrospiro[benzo[d][1,3]oxazine-4,3'-piperidine]-1'-carboxylate (slower eluting peak from step 1 of Intermediate A6-15, 1.0 g, 2.0 mmol) in THF (20 mL) was cooled to 40° C. TBAF (6.0 mL, 6.0 mmol, 1 M THF solution) was added to the flask, and the reaction mixture was warmed to 40° C. for 12 h. The reaction was quenched with ice-water and stirred for 15 min. The mixture was diluted with EtOAc, layers were separated and the combined organic layers were washed with brine. The organic layer was dried over $MgSO_4$, filtered and concentrated under reduced pressure to afford a crude product that was carried forward without further purification. The crude alcohol (100 mg, 0.260 mmol) in DCM (5 mL) under $N_2$ atmosphere was cooled to −78° C. DAST (625 mg, 0.390 mmol) in DCM (2 mL) was added dropwise, and the reaction mixture was stirred at −78° C. for 1 h. The reaction mixture was purified directly by silica gel chromatography (EtOAc:DCM) to afford the title compound. LCMS $[M+H]^+$=411.3 (calcd. 411.1).

Step 2: (rac)-(4R or S,5'R or S)-6-Chloro-5,5'-difluorospiro[benzo[d][1,3]oxazine-4,3'-piperidin]-2(1H)-one: HCl (0.6 mL, 2.3 mmol, 4 M in dioxane) was added to a vial containing (rac)-tert-butyl (4R or S,5'R or S)-6-chloro-5,5'-difluoro-2-oxo-1,2-dihydrospiro[benzo[d][1,3]oxazine-4,3'-piperidine]-1'-carboxylate (45 mg, 0.12 mmol) in 1,4-dioxane (0.6 mL), and the reaction mixture was stirred at rt for 3 h. The solvents were removed under reduced pressure to give a crude product that was carried forward to the next step without further purification. LCMS $[M+H]^+$=289.1 (calcd. 289.1).

Intermediate A6-17

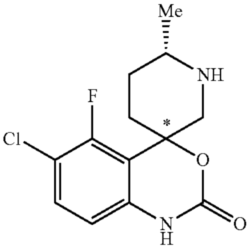 [SMILES: C[C@H]1CCC2(CN1)OC(=O)Nc1ccc(Cl)c(F)c12]

(4R and S,6'S)-6-Chloro-5-fluoro-6'-methylspiro[benzo[d][1.3]oxazine-4,3'-piperidin]-2(1H)-one Step 1: Benzyl (4R and S,6'S)-6-chloro-5-fluoro-6'-methyl-2-oxo-1,2-dihydrospiro[benzo[d][1,3]oxazine-4,3'-piperidine]-1'-carboxylate: THF (15 mL) was added to a tert-butyl (4-chloro-3-fluorophenyl)carbamate (600 mg, 2.44 mmol) and cooled to −78° C. $^{n}$BuLi (3.0 mL, 7.57 mmol, 2.5 M in hexanes) was added over 40 min, and the resulting mixture was stirred at −78° C. for an additional 45 min. A solution of $LaCl_3 \cdot 2LiCl$ (6.1 mL, 3.66 mmol, 0.6 M in THF) and benzyl (S)-2-methyl-5-oxopiperidine-1-carboxylate (900 mg, 3.66 mmol) was added at −78° C. over 40 min, and the reaction mixture was warmed to rt and stirred for 16 h. KO$^t$Bu (1.40 mL, 2.44 mmol, 1.7 M in THF) was added, and the reaction was heated to 60° C. for an additional 3 h. The reaction was cooled to rt, quenched with 1 M HCl and diluted with EtOAc. The layers were separated and aq. layer was extracted with EtOAc. The combined organic layers were dried over $MgSO_4$, filtered and concentrated to afford a crude residue that was purified by silica gel chromatography (EtOAc:hexanes) to afford the title compound as a mixture of diastereomers. LCMS $[M+H]^+$=419.0 (calcd. 419.1).

Step 2: (4R and S,6'S)-6-Chloro-5-fluoro-6'-methylspiro[benzo[d][1,3]oxazine-4,3'-piperidin]-2(1H)-one: HBr (3.9 mL, 71.6 mmol, 33 wt % in AcOH) was added to a vial containing benzyl (4R and S,6'S)-6-chloro-5-fluoro-6'-methyl-2-oxo-1,2-dihydrospiro[benzo[d][1,3]oxazine-4,3'-piperidine]-1'-carboxylate (600 mg, 1.43 mmol). The reaction mixture was heated to 80° C. for 12 h. The reaction was cooled to rt and concentrated to give the crude title compound that was carried forward to the next step without further purification. LCMS $[M+H]^+$=285.1 (calcd. 285.1).

Intermediate B4-1

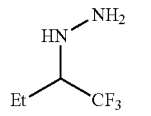

Rac-(1,1,1-Trifluorobutan-2-yl)hydrazine

Step 1: N'-(1,1,1-Trifluorobutan-2-ylidene)benzohydrazide: To a solution of 1,1,1-trifluorobutan-2-one (1.39 g, 11.0 mmol) in toluene (10 mL) was added benzohydrazide (1.50 g, 11.0 mmol), and the reaction mixture was heated to 110° C. for 18 h. The reaction was cooled to rt, poured into water and then filtered. The solid was washed with water and further dried to give the desired crude title compound. LCMS $[M+H]^+$=245.4 (calcd. 245.1)

Step 2: N-(1,1,1-Trifluorobutan-2-yl)benzohydrazide: A solution of N'-(1,1,1-trifluorobutan-2-ylidene)benzohydrazide (500 mg, 2.05 mmol) in THF (6 mL) was cooled to 0° C. and $BH_3$-THF (4.09 mL, 4.09 mmol, 1.0 M THF solution) was added dropwise. The reaction was allowed to warm to rt and was stirred for 14 h. The reaction was recooled to 0° C. and quenched with MeOH. The solvents were removed under reduced pressure and dichloromethane was added. The slurry was filtered to remove insoluble material, and the organic layer was washed with satd. aq. $NH_4Cl$, dried over $MgSO_4$, filtered and concentrated to afford the title compound. LCMS $[M+H]^+$=246.7 (calcd. 247.1).

Step 3: (1,1,1-Trifluorobutan-2-yl)hydrazine: To a solution of N-(1,1,1-trifluorobutan-2-yl)benzohydrazide (274 mg, 1.11 mmol) in MeOH (3 mL) was added hydrogen chloride (1.48 mL, 17.8 mmol, 37% aq. solution), and the resulting mixture was heated to 80° C. for 16 h. The reaction was cooled to rt and concentrated under reduced pressure. EtOAc was added, and the precipitate was filtered and washed with EtOAc to afford the title compound. $^1H$ NMR (400 MHz, $CD_3OD$) δ 3.34-3.49 (m, 1H), 1.80 (dqd, J=14.7, 7.5, 4.4 Hz, 1H), 1.46-1.65 (m, 1H), 0.97-1.27 (m, 3H).

TABLE B

The following compounds were prepared using procedures similar to those described in Intermediate B4-1 using the appropriate starting materials.

| Intermediate | Structure | Name | LCMS $[M + H]^+$ |
|---|---|---|---|
| B4-2 | 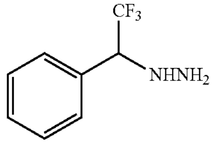 [SMILES: NNC(c1ccccc1)C(F)(F)F] | (2,2,2-Trifluoro-1-phenylethyl)hydrazine | Calcd. 191.1, found 191.1 |

Intermediate C4-1

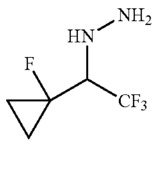 [SMILES: NNC(C(F)(F)F)C1(F)CC1]

(2,2,2-Trifluoro-1-(1-fluorocyclopropyl)ethyl)hydrazine

Step 1: N-((1-Fluorocyclopropyl)methylene)benzohydrazide: 1-Fluorocyclopropane-1-carbaldehyde (176 mg, 2.0 mmol) was added to a solution of benzohydrazide (272 mg, 2.0 mmol) in toluene (4 mL), and the reaction mixture was heated to 60° C. for 1 h. The reaction was cooled to rt and concentrated to afford a crude product that was carried forward to the next step without any purification. LCMS $[M+H]^+$=207.1 (calcd. 207.1).

Step 2: N-(2,2,2-Trifluoro-1-(1-fluorocyclopropyl)ethyl)benzohydrazide: Allyltrimethylsilane (0.48 mL, 3.0 mmol) and $BF_3 \cdot Et_2O$ (0.37 mL, 3.0 mmol) were successively added to a suspension of N'-((1-fluorocyclopropyl)methylene)benzohydrazide (412 mg, 2.0 mmol) in 1,2-dichloroethane (4.0 mL), and the mixture was heated at reflux for 5 min. The solvent was evaporated under vacuum, and the resulting residue was dissolved in DMF (4 mL). $TMSCF_3$ (0.60 mL, 4.0 mmol) and NaOAc (660 mg, 8.0 mmol) were added, and the mixture was heated to 55° C. for 3 h. The reaction was cooled to rt and quenched with satd. aq. $Na_2CO_3$, and stirred for additional 5 min. The mixture was diluted with $H_2O$ and extracted with EtOAc. The combined organic layers were dried over $MgSO_4$, filtered, and concentrated to afford a crude residue that was purified by silica gel chromatography (EtOAc:hexanes) to afford the title compound. LCMS $[M+H]^+$=277.1 (calcd. 277.1).

Step 3: (2,2,2-Trifluoro-1-(1-fluorocyclopropyl)ethyl)hydrazine: To a solution of N-(2,2,2-trifluoro-t-(1-fluorocyclopropyl)ethyl)benzohydrazide (140 mg, 0.51 mmol) in MeOH (0.75 mL) was added HCl (0.7 mL, 8.1 mmol, 37% aq. solution), and the resulting mixture was heated to 80° C.

for 16 h. The reaction was cooled to rt, and concentrated to afford a crude product that was azeotroped with toluene to afford the title compound, which was carried forward without purification. LCMS $[M+H]^+$=173.1 (calcd. 173.1).

TABLE C

The following compounds were prepared using procedures similar to those described in Intermediate C4-1 using the appropriate starting materials.

| Intermediate | Structure | Name | LCMS $[M + H]^+$ |
|---|---|---|---|
| C4-2 | 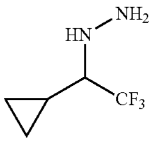 | (1-Cyclopropyl-2,2,2-trifluoroethyl)hydrazine | Calcd. 155.1, found 155.1 |
| C4-3 | 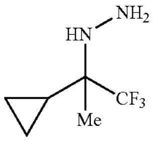 [SMILES: CC(NN)(C1CC1)C(F)(F)F] | (2-Cyclopropyl-1,1,1-trifluoropropan-2-yl)hydrazine | Calcd. 169.1, found 169.1 |
| C4-4 | 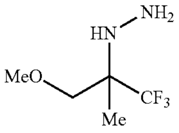 [SMILES: COCC(C)(NN)C(F)(F)F] | (1,1,1-Trifluoro-3-methoxy-2-methylpropan-2-yl)hydrazine | Calcd. 173.1, found 173.1 |
| C4-5 | 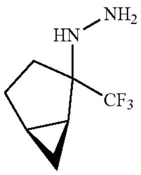 [SMILES: NNC1(C(F)(F)F)CC[C@@H]2C[C@@H]21] | ((1S,5R)-2-(Trifluoromethyl)bicyclo[3.1.0]hexan-2-yl)hydrazine | Calcd. 181.1, found 181.1 |
| C4-6 | 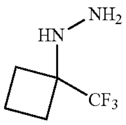 | (1-(Trifluoromethyl)cyclobutyl)hydrazine | Calcd. 155.1, found 155.1 |
| C4-7 | 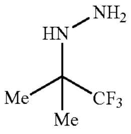 | (1,1,1-Trifluoro-2-methylpropan-2-yl)hydrazine | Calcd. 143.1, found 143.1 |
| C4-8 | 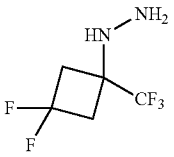 [SMILES: NNC1(C(F)(F)F)CC(F)(F)C1] | (3,3-Difluoro-1-(trifluoromethyl)cyclobutyl)hydrazine | Calcd. 191.1, found 191.1 |
| C4-9 | 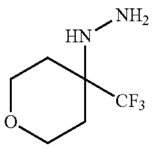 [SMILES: NNC1(C(F)(F)F)CCOCC1] | (4-(Trifluoromethyl)tetrahydro-2H-pyran-4-yl)hydrazine | Calcd. 185.1, found 185.1 |

Intermediate D2-1

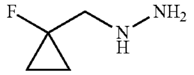

((1-Fluorocyclopropyl)methyl)hydrazine

Hydrazine (0.33 mL, 0.33 mmol, 1.0 M THF solution) was added to vial containing 1-(bromomethyl)-1-fluorocyclopropane (50 mg, 0.33 mmol) in EtOH (0.3 mL), and the resulting mixture was heated to 70° C. for 16 h. The reaction was cooled to rt and concentrated to afford a crude product that was azeotroped with toluene to afford the title compound, which was carried forward without purification. LCMS $[M+H]^+$=105.1 (calcd. 105.1).

TABLE D

The following compounds were prepared using procedures similar to those described in Intermediate D2-1 using the appropriate starting materials.

| Intermediate | Structure | Name | LCMS $[M + H]^+$ |
|---|---|---|---|
| D2-2 | 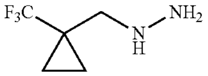 | ((1-(Trifluoromethyl)-cyclopropyl)methyl)hydrazine | Calcd. 155.1, found 155.0 |

Intermediate E3-1

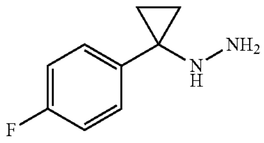 [SMILES: NNC1(c2ccc(F)cc2)CC1]

(1-(4-Fluorophenyl)cyclopropyl)hydrazine

Step 1: Di-tert-butyl 1-(1-(4-fluorophenyl)cyclopropyl)hydrazine-1,2-dicarboxylate Acetonitrile (20 mL) was added to a vial containing 1-(4-fluorophenyl)cyclopropane-1-carboxylic acid (360 mg, 2.0 mmol) and $[Mes-Acr-Me]^+$ photocatalyst (16 mg, 0.04 mmol). The solution was degassed with $N_2$ for 5 min. After degassing, DBU (0.06 mL, 0.4 mmol) and di-tert-butyl azodicarboxylate (576 mg, 2.5 mmol) were added in quick succession. The vial was placed in front of 450 nm blue LEDs (Merck photoreactor) and left to stir for 12 h. The solvents were removed under reduced pressure, and the crude mixture was purified by silica gel chromatography (EtOAc:hexanes) to afford the title compound. LCMS $[M-155]^+$=211.1 (calcd. 211.2).

Step 2: (1-(4-Fluorophenyl)cyclopropyl)hydrazine: HCl (6.6 mL, 26.2 mmol, 4.0 M dioxane solution) was added to a vial containing di-tert-butyl 1-(1-(4-fluorophenyl)cyclopropyl) hydrazine-1,2-dicarboxylate (640 mg, 1.75 mmol), and the reaction mixture was stirred at rt for 16 h. The solvents were removed under reduced pressure, and the mixture was azeotroped with toluene to afford the title compound, which was carried forward without purification. LCMS $[M+H]^+$ =167.0 (calcd. 167.1).

TABLE E

The following compounds were prepared using procedures similar to those described in Intermediate E3-1 using the appropriate starting materials.

| Intermdiate | Structure | Name | LCMS $[M-NHNH_2]^+$ |
|---|---|---|---|
| E3-2 | 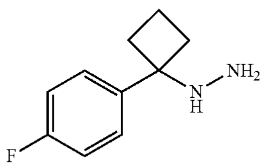 [SMILES: NNC1(c2ccc(F)cc2)CCC1] | (1-(4-Fluorophenyl)cyclobutyl)hydrazine | Calcd. 149.1, found 149.1 |

Intermediate F4-1

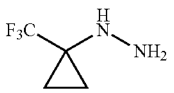

(1-(Trifluoromethyl)cyclopropyl)hydrazine

Step 1: tert-Butyl (1-(trifluoromethyl)cyclopropyl)carbamate: To a solution of 1-(trifluoromethyl)cyclopropanecarboxylic acid (5.00 g, 32.4 mmol) in $^t$BuOH (5 mL) was added TEA (5.00 mL, 35.7 mmol) and diphenylphosphinyl azide (11.8 g, 48.7 mmol), and the resulting mixture was stirred at rt for 0.5 h and heated to 100° C. for 15 h. The reaction was diluted with EtOAc and washed with 5% citric acid, satd. aq. $NaHCO_3$, and brine. The organic layers were dried over $Na_2SO_4$, filtered and concentrated to afford the crude product which was purified by silica gel chromatography (EtOAc:petroleum ether) to give the title compound. $^1$H NMR (400 MHz, $CDCl_3$) δ 4.99-5.12 (m, 1H), 1.45 (s, 9H), 1.26 (br s, 2H), 1.11 (br s, 2H).

Step 2: tert-Butyl nitroso(1-(trifluoromethyl)cyclopropyl) carbamate: Nitrosyl tetrafluoroborate (78 mg, 0.67 mmol) was added over small portions to a solution of tert-butyl (1-(trifluoromethyl)cyclopropyl)carbamate (100 mg, 0.440 mmol) in pyridine (0.2 mL) and acetonitrile (2 mL) at −30° C. The solution was stirred at −30° C. for 30 min, then warmed to 0° C. for 2 h. The reaction was concentrated under reduced pressure to give crude product which was purified by preparatory TLC (EtOAc:petroleum ether) to afford the title compound. $^1$H NMR (400 MHz, $CDCl_3$) δ 1.69 (s, 9H), 1.57-1.62 (m, 4H).

Step 3: (1-(Trifluoromethyl)cyclopropyl)hydrazine: tert-Butyl nitroso(1-(trifluoromethyl)cyclopropyl)carbamate (100 mg, 0.390 mmol) in MeOH (2 mL) was stirred at −78° C. for 30 min. HCl (0.32 mL, 3.9 mmol, 37% aq. solution) and zinc (257 mg, 3.93 mmol) were added at −78° C., and the resulting mixture was stirred for 2 h. The reaction was warmed to rt, filtered and concentrated to afford the title compound, which was carried forward without purification. LCMS $[M+H]^+$=141.0 (calcd. 141.1).

Intermediate G2-1

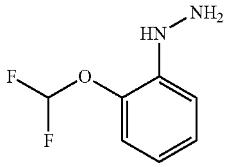 [SMILES: NNc1ccccc1OC(F)F]

(2-(Difluoromethoxy)phenyl)hydrazine

THF (1 ml) was added to a mixture of $NaO^tBu$ (129 mg, 1.35 mmol) and X-PHOS Pd G2 (10.6 mg, 0.0130 mmol). 1-Bromo-2-(difluoromethoxy)benzene (300 mg, 1.35 mmol) was added, and the mixture was stirred at rt for 10 min. Hydrazine (42 μL, 1.3 mmol) was added in one portion, and the vial was heated to 90° C. (preheated bath) and allowed to stir for 12 h. The reaction was cooled to rt, diluted with MeOH and filtered. The filtrate was concentrated to dryness and the crude mixture that was purified by reversed-phase preparatory-HPLC (C18 stationary phase, ACN/water+0.1% TFA) to afford the title compound. LCMS $[M+H]^+$=175.0 (calcd. 175.1).

TABLE G

The following compounds were prepared using procedures similar to those described in Intermediate G2-1 using the appropriate starting materials.

| Intermediate | Structure | Name | LCMS $[M + H]^+$ |
|---|---|---|---|
| G2-2 | 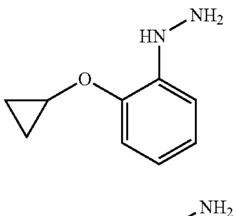 | (2-Cyclopropoxyphenyl)hydrazine | Calcd. 165.1, found 165.0 |
| G2-3 | 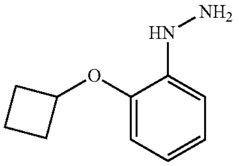 [SMILES: NNc1ccccc1OC1CCC1] | (2-Cyclobutoxyphenyl)hydrazine | Calcd. 179.1, found 179.0 |
| G2-4 | 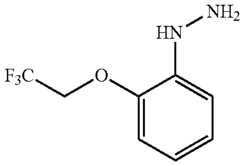 [SMILES: NNc1ccccc1OCC(F)(F)F] | (2-(2,2,2-Trifluoroethoxy)phenyl)hydrazine | Calcd. 207.1, found 207.0 |

TABLE G-continued

The following compounds were prepared using procedures similar to those described in Intermediate G2-1 using the appropriate starting materials.

| Intermediate | Structure | Name | LCMS $[M + H]^+$ |
|---|---|---|---|
| G2-5 | 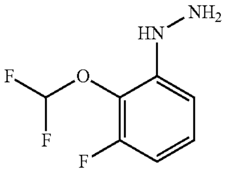 [SMILES: NNc1cccc(F)c1OC(F)F] | (2-(Difluoromethoxy)-3-fluorophenyl)hydrazine | Calcd. 193.1, found 193.1 |
| G2-6 | 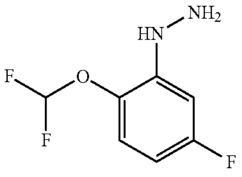 [SMILES: NNc1cc(F)ccc1OC(F)F] | (2-(Difluoromethoxy)-5-fluorophenyl)hydrazine | Calcd. 193.1, found 193.1 |
| G2-7 | 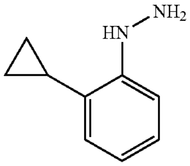 [SMILES: NNc1ccccc1C1CC1] | (2-Cyclopropylphenyl)hydrazine | Calcd. 149.1, found 149.1 |
| G2-8 | 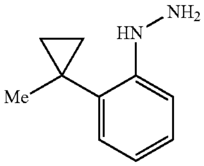 [SMILES: CC1(c2ccccc2NN)CC1] | (2-(1-Methylcyclopropyl)phenyl)hydrazine | Calcd. 163.1, found 163.0 |

Intermediate H4-1

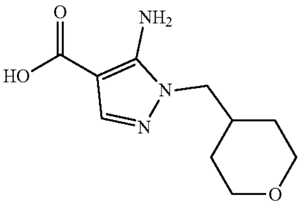 [SMILES: Nc1c(C(=O)O)cnn1CC1CCOCC1]

5-Amino-1-((tetrahydro-2H-pyran-4-yl)methyl)-1H-pyrazole-4-carboxylic Acid

Step 1: Ethyl 5-amino-1-((tetrahydro-2H-pyran-4-yl)methyl)-1H-pyrazole-4-carboxylate Sodium hydride (30.9 mg, 1.29 mmol) was added to a stirred solution of ethyl 5-amino-1H-pyrazole-4-carboxylate (100 mg, 0.650 mmol) in ACN (1 mL) 0'° C. After 1 h, 4-(bromomethyl)tetrahydro-2H-pyran (173 mg, 0.970 mmol) was added, and the resulting mixture was heated to 80° C. for 12 h. The reaction was cooled to rt and quenched with satd. aq. $NH_4Cl$. The aq. phase was extracted with EtOAc, and the combined organic layers were dried over $Na_2SO_4$, filtered and concentrated under reduced pressure. The crude product was purified by preparative reverse phase HPLC (C18 stationary phase, ACN/water+0.04% $NH_4OH$) to afford the title compound. LCMS $[M+H]^+$=254.2 anhydrous (calcd. 254.1).

Step 2: 5-Amino-1-((tetrahydro-2H-pyran-4-yl)methyl)-1H-pyrazole-4-carboxylic acid: To a solution of ethyl 5-amino-1-((tetrahydro-2H-pyran-4-yl)methyl)-1H-pyrazole-4-carboxylate (100 mg, 0.400 mmol) in EtOH (1 mL) and $H_2O$ (0.2 mL) was added $LiOH{\cdot}H_2O$ (20 mg, 0.47 mmol), and the resulting mixture was heated to 60° C. for 12 h. The mixture was concentrated to give the crude product was used in the next step without any purification LCMS $[M+H]^+$=226.0 (calcd. 226.1).

TABLE H

The following compounds were prepared using procedures similar to those described in Intermediate H4-1 using the appropriate starting materials.

| Intermediate | Structure | Name | LCMS $[M + H]^+$ |
|---|---|---|---|
| H4-2 | 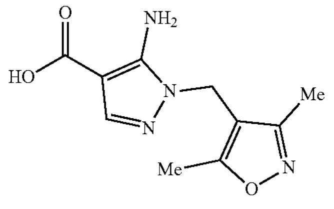 [SMILES: Cc1noc(C)c1Cn1ncc(C(=O)O)c1N] | 5-Amino-1-((3,5-dimethylisoxazol-4-yl)methyl)-1H-pyrazole-4-carboxylic acid | Calcd. 237.1, found 237.0 |
| H4-3 | 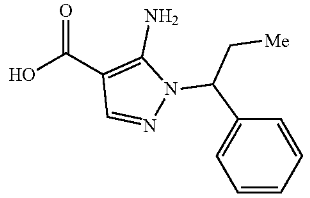 [SMILES: CCC(c1ccccc1)n1ncc(C(=O)O)c1N] | 5-Amino-1-(1-phenylpropyl)-1H-pyrazole-4-carboxylic acid | Calcd. 246.1, found 246.1 |
| H4-4 | 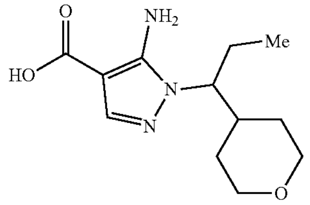 [SMILES: CCC(C1CCOCC1)n1ncc(C(=O)O)c1N] | 5-Amino-1-(1-(tetrahydro-2H-pyran-4-yl)propyl)-1H-pyrazole-4-carboxylic acid | Calcd. 254.1, found 254.2 |
| H4-5 | 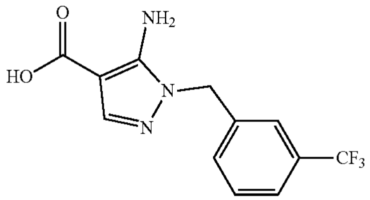 [SMILES: Nc1c(C(=O)O)cnn1Cc1cccc(C(F)(F)F)c1] | 5-Amino-1-(3-(trifluoromethyl)benzyl)-1H-pyrazole-4-carboxylic acid | Calcd. 286.1, found 286.0 |
| H4-6 | 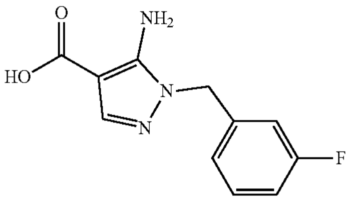 [SMILES: Nc1c(C(=O)O)cnn1Cc1cccc(F)c1] | 5-Amino-1-(3-fluorobenzyl)-1H-pyrazole-4-carboxylic acid | Calcd. 236.1, found 236.0 |

Intermediate I4-1

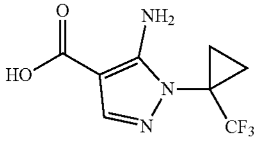 [SMILES: Nc1c(C(=O)O)cnn1C1(C(F)(F)F)CC1]

5-Amino-1-(1-(trifluoromethyl)cyclopropyl)-1H-pyrazole-4-carboxylic Acid

Step 1: Ethyl 5-amino-1-(1-(trifluoromethyl)cyclopropyl)-1H-pyrazole-4-carboxylate: A solution of (1-(trifluoromethyl)cyclopropyl)hydrazine (50 mg, 0.36 mmol), methyl 2-cyano-3-ethoxyacrylate (56 mg, 0.36 mmol) and DIEA (0.31 mL, 1.8 mmol) in EtOH (1 mL) was heated to 80° C. for 12 h. The reaction was cooled to rt, and concentrated under reduced pressure to give a crude product that was purified by preparatory TLC (EtOAc:petroleum ether) to afford the title compound. LCMS $[M+H]^+$=264.1 (calcd. 264.1).

Step 2: 5-Amino-1-(1-(trifluoromethyl)cyclopropyl)-1H-pyrazole-4-carboxylic acid: To a solution of ethyl 5-amino-1-(1-(trifluoromethyl)cyclopropyl)-1H-pyrazole-4-carboxylate (50 mg, 0.20 mmol) in MeOH (2 mL) and $H_2O$ (0.5 mL) was added $LiOH·H_2O$ (42.1 mg, 1.0 mmol). The resulting mixture was heated to 70° C. for 5 h. The reaction was cooled to rt, concentrated, acidified by 1 M HCl to pH 2 and extracted with EtOAc. The combined organic layers were dried over $Na_2SO_4$, filtered, and concentrated under reduced pressure to give a crude product that was carried forward without further purification. LCMS $[M+H]^+$=235.9 (calcd. 236.1).

Intermediate I4-2

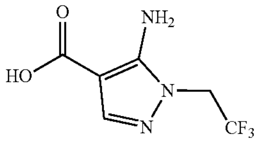 [SMILES: Nc1c(C(=O)O)cnn1CC(F)(F)F]

Intermediate I4-2 was prepared following procedures similar to those described above for Intermediate I4-1. LCMS $[M+H]^+$=210.1 (calcd. 210.0).

Intermediate L3-1

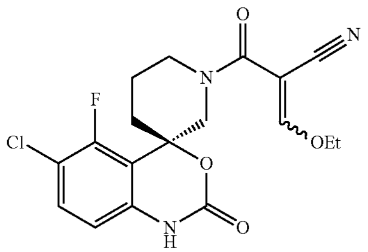

(R,E/Z)-2-(6-Chloro-5-fluoro-2-oxo-1,2-dihydrospiro[benzo[d][1,3]oxazine-4,3'-piperidine]-1'-carbonyl)-3-ethoxyacrylonitrile Step 1: 3-(6-Chloro-5-fluoro-2-oxo-1,2-dihydrospiro[benzo[d][1,3]oxazine-4,3'-piperidin]-1'-yl)-3-oxopropanenitrile: DIEA (7.06 mL, 40.4 mmol) was added to a solution of 6-chloro-5-fluoro-2-oxo-1,2-dihydrospiro[benzo[d][1,3]oxazine-4,3'-piperidin]-1'-ium chloride (4.14 g, 13.5 mmol) and 2-cyanoacetic acid (1.26 g, 14.8 mmol) in EtOAc (41 mL) and DMF (6.2 mL). 1-Propanephonic anhydride (9.60 ml, 16.2 mmol) was added, and the resulting mixture was stirred at rt overnight. The reaction was quenched with $H_2O$ and extracted with EtOAc. The combined organic layers were washed with brine, dried over $MgSO_4$ and concentrated to afford a crude residue that was purified by silica gel chromatography (((3:1)EtOH:EtOAc):hexanes) to afford the title compound. LCMS $[M+H]^+$=337.9 (calcd. 338.1).

Step 2: (R,E/Z)-2-(6-Chloro-5-fluoro-2-oxo-1,2-dihydrospiro[benzo[d][1,3]oxazine-4,3'-piperidine]-1'-carbonyl)-3-ethoxyacrylonitrile: $ZnCl_2$ (anhydrous, 303 mg, 2.21 mmol) was added to 3-(6-chloro-5-fluoro-2-oxo-1,2-dihydrospiro[benzo[d][1,3]oxazine-4,3'-piperidin]-1'-yl)-3-oxopropanenitrile (2.50 g, 7.40 mmol) in triethyl orthoformate (18.5 mL, 111 mmol) and NMP (0.8 mL), and the reaction mixture was heated to 130° C. for 4 h. The reaction was cooled to rt, quenched with satd. aq. $NaHCO_3$ and extracted with EtOAc. The combined organic layers were dried over $MgSO_4$, filtered, and concentrated to afford a crude residue that was purified by silica gel chromatography (EtOAc: hexanes) to afford the title compound. LCMS $[M+H]^+$=394.0 (calcd. 394.1).

Intermediate L3-2

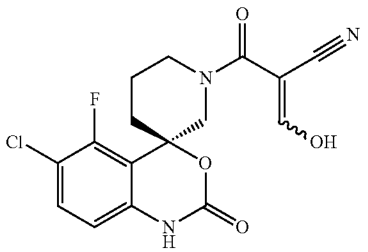 [SMILES: CCOC=C(C#N)C(=O)N1CCC[C@@]2(C1)OC(=O)Nc1ccc(Cl)c(F)c12]

(R)-2-(6-Chloro-5-fluoro-2-oxo-1,2-dihydrospiro[benzo[d][1,3]oxazine-4,3'-piperidine]-1'-carbonyl)-3-hydroxyacrylonitrile THF (15 mL) was added to a mixture of (R)-3-(6-chloro-5-fluoro-2-oxo-1,2-dihydrospiro[benzo[d][1,3]oxazine-4,3'-piperidin]-1'-yl)-3-oxopropanenitrile (1.82 g, 4.43 mmol) and methyl formate (3.99 g, 66.5 mmol). The reaction mixture was sonicated to dissolve the solid followed by dropwise addition of a solution of $KO^tBu$ (14.2 mL, 14.2 mmol, 1 M in THF), and the resulting mixture was stirred at rt for 12 h. The reaction was diluted with $H_2O$, neutralized with 1 M HCl to pH 6, and extracted with EtOAc. The combined organic layers were dried over $MgSO_4$, filtered and concentrated to afford the crude title compound that was carried forward to the next step without any purification. LCMS $[M+H]^+$=366.4 (calcd. 366.1).

Example 1

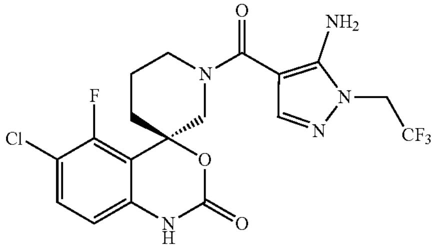 [SMILES: Nc1c(C(=O)N2CCC[C@@]3(C2)OC(=O)Nc2ccc(Cl)c(F)c23)cnn1CC(F)(F)F]

(R)-1'-(5-Amino-1-(2,2,2-trifluoroethyl)-1H-pyrazole-4-carbonyl)-6-chloro-5-fluorospiro[benzo[d][1,3]oxazine-4,3'-piperidin]-2(1H)-one (R,E/Z)-2-(6-Chloro-5-fluoro-2-oxo-1,2-dihydrospiro[benzo[d][1,3]oxazine-4,3'-piperidine]-1'-carbonyl)-3-ethoxyacrylonitrile (0.25 mL, 0.10 mmol, 0.4 M stock solution in EtOH) was added to a vial containing (2,2,2-trifluoroethyl)hydrazine (17 mg, 0.15 mmol). TEA (42 µL, 0.30 mmol) was added to the vial, and the mixture was heated to 70° C. for 12 h. The reaction was cooled to rt and was purified directly by preparative reverse phase HPLC (C18 stationary phase, ACN/water+0.05% TFA) to afford the title compound.: $^1H$ NMR (500 MHz, $CD_3OD$) δ 7.55 (s, 1H), 7.43 (t, J=8.1 Hz, 1H), 6.74 (d, J=8.6 Hz, 1H), 4.76-4.66 (m, 3H), 4.46 (d, J=13.3 Hz, 1H), 3.53 (s, 1H), 3.24-3.16 (m, 1H), 2.52 (t, J=11.5 Hz, 1H), 2.30 (d, J=13.6

Hz, 1H), 2.17 (q, J=10.4 Hz, 1H), 1.73 (d, J=12.7 Hz, 1H). LCMS $[M+H]^+$=462.3 (calcd. 462.1).

Example 2

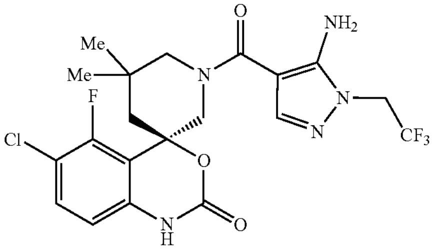 [SMILES: CC1(C)CN(C(=O)c2cnn(CC(F)(F)F)c2N)C[C@]2(C1)OC(=O)Nc1ccc(Cl)c(F)c12]

(R)-1'-(5-Amino-1-(2,2,2-trifluoroethyl)-1H-pyrazole-4-carbonyl)-6-chloro-5-fluoro-5',5'-dimethylspiro[benzo[d][1,3]oxazine-4,3'-piperidin]-2(1H)-one A 3 mL vial was charged with (R)-6-chloro-5-fluoro-5',5'-dimethylspiro[benzo[d][1,3]oxazine-4,3'-piperidin]-2(1H)-one (67 mg, 0.20 mmol) and 5-amino-1-(2,2,2-trifluoroethyl)-1H-pyrazole-4-carboxylic acid (84 mg, 0.40 mmol) in DMF (0.2 mL). To this mixture, TEA (0.14 mL, 1.0 mmol) was added followed by the addition of T3P (0.18 μL, 0.6 mmol, 50% w/v in DMF), and the resulting mixture was allowed to stir at rt for 2 h. The reaction mixture was purified directly via preparative reverse phase HPLC (C18 stationary phase, ACN/water+0.05% $HCO_2H$) to afford the title compound. $^1$H NMR (500 MHz, $CD_3OD$) δ 7.62 (s, 1H), 7.44-7.40 (m, 1H), 6.74 (dd, J=8.7, 1.1 Hz, 1H), 4.79-4.70 (m, 3H), 4.27 (d, J=12.9 Hz, 1H), 3.73 (s, 1H), 2.97 (d, J=12.4 Hz, 1H), 2.17-2.03 (m, 2H), 1.24 (s, 3H), 1.03 (s, 3H). LCMS $[M+H]^+$=490.4 (calcd. 490.1).

Examples 3 and 4

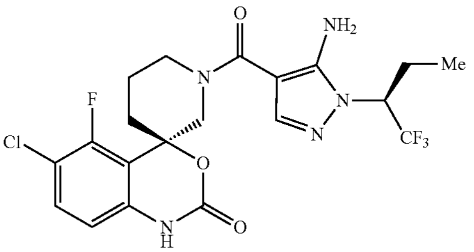

and

-continued

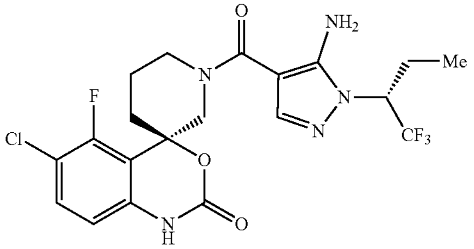

(R)-1'-(5-amino-1-((R)-1,1,1-trifluorobutan-2-yl)-1H-pyrazole-4-carbonyl)-6-chloro-5-fluorospiro[benzo[d][1,3]oxazine-4,3'-piperidin]-2(1H)-one and (R)-1'-(5-amino-1-((S)-1,1,1-trifluorobutan-2-yl)-1H-pyrazole-4-carbonyl)-6-chloro-5-fluorospiro[benzo[d][1,3]oxazine-4,3'-piperidin]-2(1H)-one (R)-2-(6-Chloro-5-fluoro-2-oxo-1,2-dihydrospiro[benzo[d][1,3]oxazine-4,3'-piperidine]-1'-carbonyl)-3-hydroxyacrylonitrile (0.25 mL, 0.01 mmol, 0.4 M stock solution in AcOH) was added to a vial containing R- and S-(1,1,1-trifluorobutan-2-yl)hydrazine (31 mg, 0.15 mmol), and the resulting mixture was heated to 80° C. for 12 h. The crude mixture was purified directly via preparative reverse phase HPLC (C18 stationary phase, ACN/water+0.05% TFA) to afford a mixture of diastereomers of the title compound. The title compounds were resolved by preparative chiral SFC with Method A. The faster eluting isomer of the title compound was obtained (Example 3): $^1$H NMR (400 MHz, $CD_3OD$) δ 7.57 (s, 1H), 7.41 (dd, J=8.6, 7.8 Hz, 1H), 6.72 (dd, J=8.7, 1.3 Hz, 1H), 4.74-4.81 (m, 1H), 4.68 (br d, J=13.4 Hz, 1H), 4.45 (br d, J=12.2 Hz, 1H), 3.43-3.58 (m, 1H), 3.05-3.25 (m, 1H), 2.42-2.58 (m, 1H), 2.24-2.34 (m, 2H), 2.11-2.22 (m, 1H), 1.95-2.07 (m, 1H), 1.72 (dt, J=11.3, 2.2 Hz, 1H), 0.82 (t, J=7.3 Hz, 3H). LCMS $[M+H]^+$=490.1 (calcd. 490.1). The slower eluting isomer of the title compound was obtained (Example 4). $^1$H NMR (400 MHz, $CD_3OD$) δ 7.57 (s, 1H), 7.41 (dd, J=8.7, 7.7 Hz, 1H), 6.73 (dd, J=8.7, 1.3 Hz, 1H), 4.76-4.80 (m, 1H), 4.68 (br d, J=14.9 Hz, 1H), 4.46 (br d, J=11.5 Hz, 1H), 3.41-3.62 (m, 1H), 3.02-3.25 (m, 1H), 2.45-2.60 (m, 1H), 2.22-2.36 (m, 2H), 2.10-2.22 (m, 1H), 2.00 (dqd, J=14.1, 7.3, 3.9 Hz, 1H), 1.65-1.77 (m, 1H), 0.80-0.88 (m, 3H). LCMS $[M+H]^+$=490.2 (calcd. 490.1).

TABLE 1

Following procedures similar to those described for Examples 1-4, the following compounds were prepared using appropriate starting materials.

| Example | Structure | Name | Exact Mass $[M + H]^+$ |
| --- | --- | --- | --- |
| 5 | 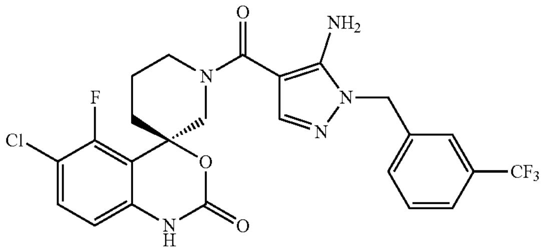 [SMILES: Nc1c(C(=O)N2CCC[C@@]3(C2)OC(=O)Nc2ccc(Cl)c(F)c23)cnn1Cc1cccc(C(F)(F)F)c1] | (R)-1'-(5-Amino-1-(3-(trifluoromethyl)benzyl)-1H-pyrazole-4-carbonyl)-6-chloro-5-fluorospiro[benzo[d][1,3]oxazine-4,3'-piperidin]-2(1H)-one | Calcd. 538.1, found 539.0 |
| 6 | 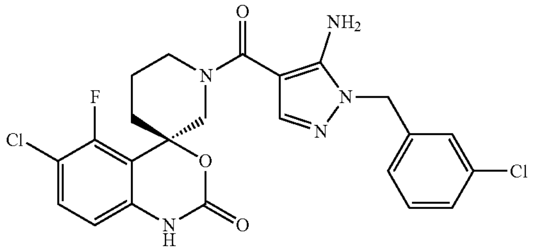 [SMILES: Nc1c(C(=O)N2CCC[C@@]3(C2)OC(=O)Nc2ccc(Cl)c(F)c23)cnn1Cc1cccc(Cl)c1] | (R)-1'-(5-Amino-1-(3-chlorobenzyl)-1H-pyrazole-4-carbonyl)-6-chloro-5-fluorospiro[benzo[d][1,3]oxazine-4,3'-piperidin]-2(1H)-one | Calcd. 504.1, found 504.1 |
| 7 | 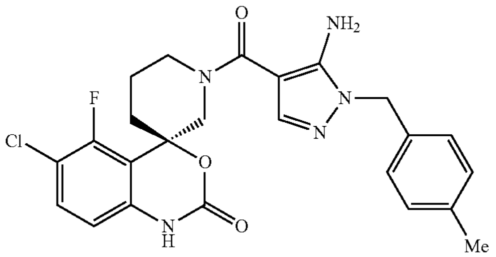 [SMILES: Cc1ccc(Cn2ncc(C(=O)N3CCC[C@@]4(C3)OC(=O)Nc3ccc(Cl)c(F)c34)c2N)cc1] | (R)-1'-(5-Amino-1-(4-methylbenzyl)-1H-pyrazole-4-carbonyl)-6-chloro-5-fluorospiro[benzo[d][1,3]oxazine-4,3'-piperidin]-2(1H)-one | Calcd. 484.2, found 484.2 |
| 8 | 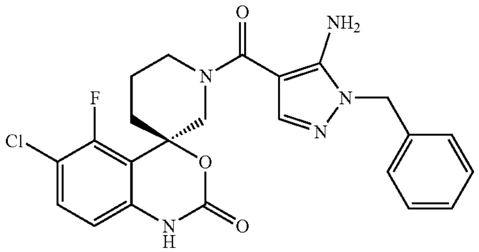 [SMILES: Nc1c(C(=O)N2CCC[C@@]3(C2)OC(=O)Nc2ccc(Cl)c(F)c23)cnn1Cc1ccccc1] | (R)-1'-(5-Amino-1-benzyl-1H-pyrazole-4-carbonyl)-6-chloro-5-fluorospiro[benzo[d][1,3]oxazine-4,3'-piperidin]-2(1H)-one | Calcd. 470.1, found 469.9 |
| 9 | 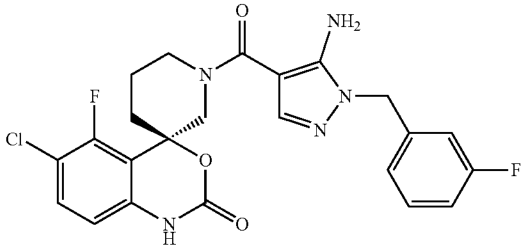 [SMILES: Nc1c(C(=O)N2CCC[C@@]3(C2)OC(=O)Nc2ccc(Cl)c(F)c23)cnn1Cc1cccc(F)c1] | (R)-1'-(5-Amino-1-(3-fluorobenzyl)-1H-pyrazole-4-carbonyl)-6-chloro-5-fluorospiro[benzo[d][1,3]oxazine-4,3'-piperidin]-2(1H)-one | Calcd. 488.1, found 488.0 |

TABLE 1-continued

Following procedures similar to those described for Examples 1-4, the following compounds were prepared using appropriate starting materials.

| Example | Structure | Name | Exact Mass $[M + H]^+$ |
| --- | --- | --- | --- |
| 10 | 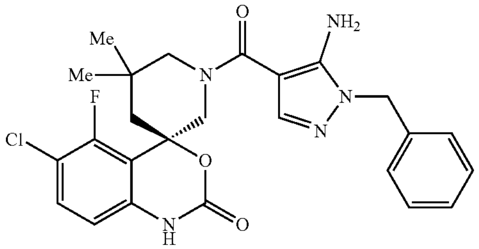 [SMILES: CC1(C)CN(C(=O)c2cnn(Cc3ccccc3)c2N)C[C@]2(C1)OC(=O)Nc1ccc(Cl)c(F)c12] | (R)-1'-(5-Amino-1-benzyl-1H-pyrazole-4-carbonyl)-6-chloro-5-fluoro-5',5'-dimethylspiro[benzo[d][1,3]oxazine-4,3'-piperidin]-2(1H)-one | Calcd. 498.2, found 498.1 |
| 11 | 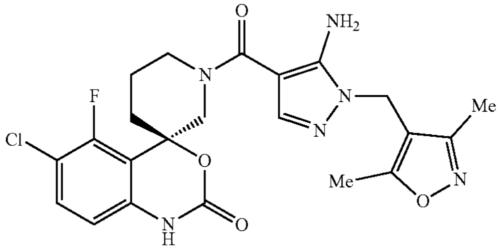 [SMILES: Cc1noc(C)c1Cn1ncc(C(=O)N2CCC[C@@]3(C2)OC(=O)Nc2ccc(Cl)c(F)c23)c1N] | (R)-1'-(5-Amino-1-((3,5-dimethylisoxazol-4-yl)methyl)-1H-pyrazole-4-carbonyl)-6-chloro-5-fluorospiro[benzo[d][1,3]oxazine-4,3'-piperidin]-2(1H)-one | Calcd. 489.1, found 489.2 |
| 12 | 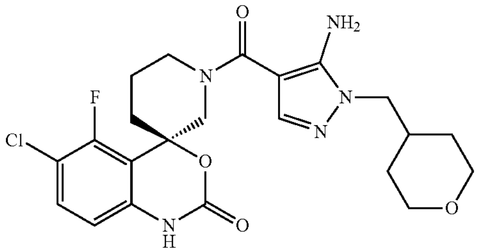 [SMILES: Nc1c(C(=O)N2CCC[C@@]3(C2)OC(=O)Nc2ccc(Cl)c(F)c23)cnn1CC1CCOCC1] | (R)-1'-(5-Amino-1-((tetrahydro-2H-pyran-4-yl)methyl)-1H-pyrazole-4-carbonyl)-6-chloro-5-fluorospiro[benzo[d][1,3]oxazine-4,3'-piperidin]-2(1H)-one | Calcd. 478.2, found 478.2 |
| 13 | 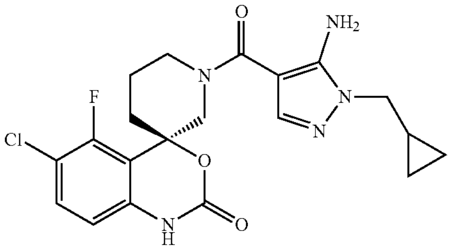 [SMILES: Nc1c(C(=O)N2CCC[C@@]3(C2)OC(=O)Nc2ccc(Cl)c(F)c23)cnn1CC1CC1] | (R)-1'-(5-Amino-1-(cyclopropylmethyl)-1H-pyrazole-4-carbonyl)-6-chloro-5-fluorospiro[benzo[d][1,3]oxazine-4,3'-piperidin]-2(1H)-one | Calcd. 434.1, found 434.4 |
| 14 | 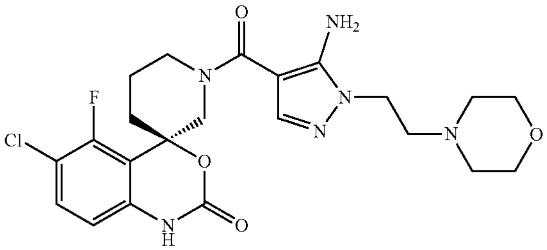 [SMILES: Nc1c(C(=O)N2CCC[C@@]3(C2)OC(=O)Nc2ccc(Cl)c(F)c23)cnn1CCN1CCOCC1] | (R)-1'-(5-Amino-1-(2-morpholinoethyl)-1H-pyrazole-4-carbonyl)-6-chloro-5-fluorospiro[benzo[d][1,3]oxazine-4,3'-piperidin]-2(1H)-one | Calcd. 493.2, found 493.4 |

TABLE 1-continued

| Example | Structure | Name | Exact Mass $[M + H]^+$ |
|---|---|---|---|
| Following procedures similar to those described for Examples 1-4, the following compounds were prepared using appropriate starting materials. | | | |
| 15 | 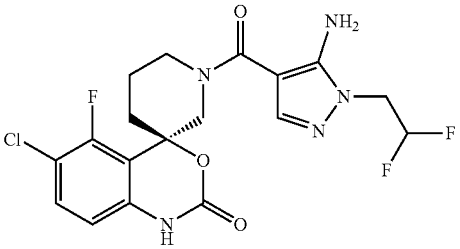 [SMILES: Nc1c(C(=O)N2CCC[C@@]3(C2)OC(=O)Nc2ccc(Cl)c(F)c23)cnn1CC(F)F] | (R)-1'-(5-Amino-1-(2,2-difluoroethyl)-1H-pyrazole-4-carbonyl)-6-chloro-5-fluorospiro[benzo[d][1,3]oxazine-4,3'-piperidin]-2(1H)-one | Calcd. 444.1, found 444.4 |
| 16 | 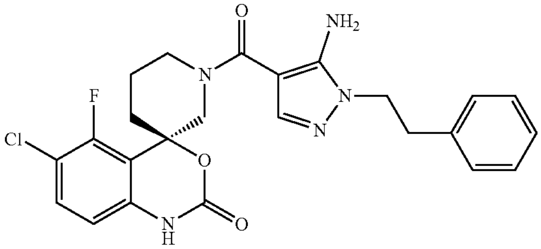 [SMILES: Nc1c(C(=O)N2CCC[C@@]3(C2)OC(=O)Nc2ccc(Cl)c(F)c23)cnn1CCc1ccccc1] | (R)-1'-(5-Amino-1-phenethyl-1H-pyrazole-4-carbonyl)-6-chloro-5-fluorospiro[benzo[d][1,3]oxazine-4,3'-piperidin]-2(1H)-one | Calcd. 484.2, found 484.4 |
| 17 | 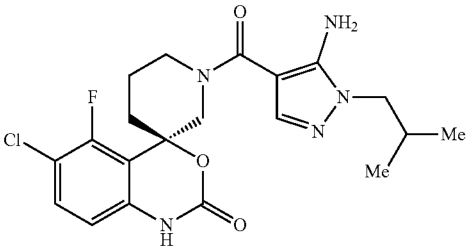 [SMILES: CC(C)Cn1ncc(C(=O)N2CCC[C@@]3(C2)OC(=O)Nc2ccc(Cl)c(F)c23)c1N] | (R)-1'-(5-Amino-1-isobutyl-1H-pyrazole-4-carbonyl)-6-chloro-5-fluorospiro[benzo[d][1,3]oxazine-4,3'-piperidin]-2(1H)-one | Calcd. 436.2, found 436.4 |
| 18 | 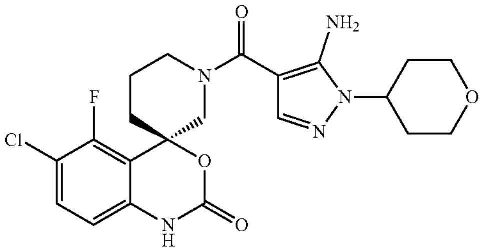 [SMILES: Nc1c(C(=O)N2CCC[C@@]3(C2)OC(=O)Nc2ccc(Cl)c(F)c23)cnn1C1CCOCC1] | (R)-1'-(5-Amino-1-(tetrahydro-2H-pyran-4-yl)-1H-pyrazole-4-carbonyl)-6-chloro-5-fluorospiro[benzo[d][1,3]oxazine-4,3'-piperidin]-2(1H)-one | Calcd. 464.1, found 464.4 |
| 19 | 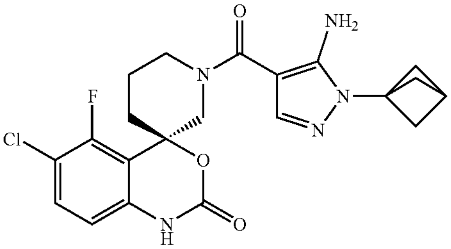 [SMILES: Nc1c(C(=O)N2CCC[C@@]3(C2)OC(=O)Nc2ccc(Cl)c(F)c23)cnn1C12CC(C1)C2] | (R)-1'-(5-Amino-1-(bicyclo[1.1.1]pentan-1-yl)-1H-pyrazole-4-carbonyl)-6-chloro-5-fluorospiro[benzo[d][1,3]oxazine-4,3'-piperidin]-2(1H)-one | Calcd. 446.1, found 446.4 |

TABLE 1-continued

Following procedures similar to those described for Examples 1-4, the following compounds were prepared using appropriate starting materials.

| Example | Structure | Name | Exact Mass $[M + H]^+$ |
|---|---|---|---|
| 20 | 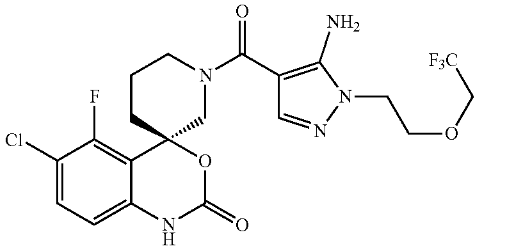 [SMILES: Nc1c(C(=O)N2CCC[C@@]3(C2)OC(=O)Nc2ccc(Cl)c(F)c23)cnn1CCOCC(F)(F)F] | (R)-1'-(5-Amino-1-(2-(2,2,2-trifluoroethoxy)ethyl)-1H-pyrazole-4-carbonyl)-6-chloro-5-fluorospiro[benzo[d][1,3]oxazine-4,3'-piperidin]-2(1H)-one | Calcd. 506.1, found 506.4 |
| 21 | 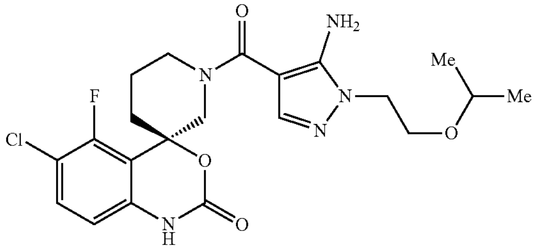 [SMILES: CC(C)OCCn1ncc(C(=O)N2CCC[C@@]3(C2)OC(=O)Nc2ccc(Cl)c(F)c23)c1N] | (R)-1'-(5-Amino-1-(2-isopropoxyethyl)-1H-pyrazole-4-carbonyl)-6-chloro-5-fluorospiro[benzo[d][1,3]oxazine-4,3'-piperidin]-2(1H)-one | Calcd. 466.2, found 466.4 |
| 22 | 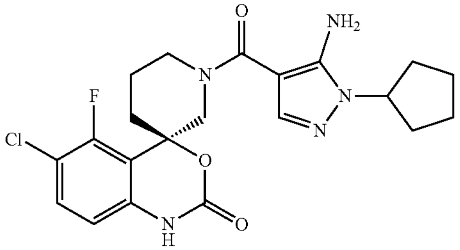 [SMILES: Nc1c(C(=O)N2CCC[C@@]3(C2)OC(=O)Nc2ccc(Cl)c(F)c23)cnn1C1CCCC1] | (R)-1'-(5-Amino-1-cyclopentyl-1H-pyrazole-4-carbonyl)-6-chloro-5-fluorospiro[benzo[d][1,3]oxazine-4,3'-piperidin]-2(1H)-one | Calcd. 448.2, found 448.4 |
| 23 | 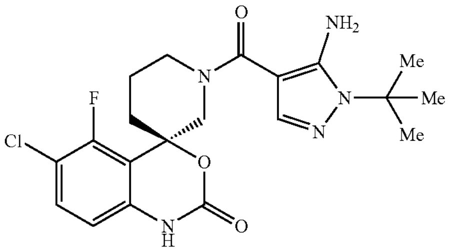 [SMILES: CC(C)(C)n1ncc(C(=O)N2CCC[C@@]3(C2)OC(=O)Nc2ccc(Cl)c(F)c23)c1N] | (R)-1'-(5-Amino-1-(tert-butyl)-1H-pyrazole-4-carbonyl)-6-chloro-5-fluorospiro[benzo[d][1,3]oxazine-4,3'-piperidin]-2(1H)-one | Calcd. 436.2, found 436.2 |
| 24 | 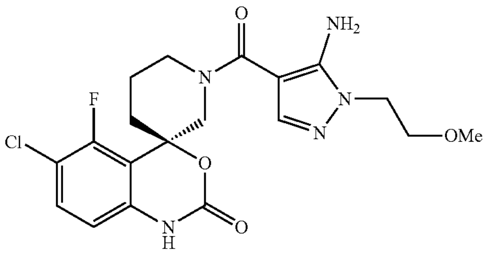 [SMILES: COCCn1ncc(C(=O)N2CCC[C@@]3(C2)OC(=O)Nc2ccc(Cl)c(F)c23)c1N] | (R)-1'-(5-Amino-1-(2-methoxyethyl)-1H-pyrazole-4-carbonyl)-6-chloro-5-fluorospiro[benzo[d][1,3]oxazine-4,3'-piperidin]-2(1H)-one | Calcd. 438.1, found 438.4 |

TABLE 1-continued

Following procedures similar to those described for Examples 1-4, the following compounds were prepared using appropriate starting materials.

| Example | Structure | Name | Exact Mass $[M + H]^+$ |
|---|---|---|---|
| 25 | 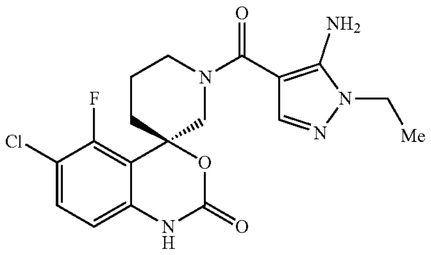 [SMILES: CCn1ncc(C(=O)N2CCC[C@@]3(C2)OC(=O)Nc2ccc(Cl)c(F)c23)c1N] | (R)-1'-(5-Amino-1-ethyl-1H-pyrazole-4-carbonyl)-6-chloro-5-fluorospiro[benzo[d][1,3]oxazine-4,3'-piperidin]-2(1H)-one | Calcd. 408.1, found 408.4 |
| 26 | 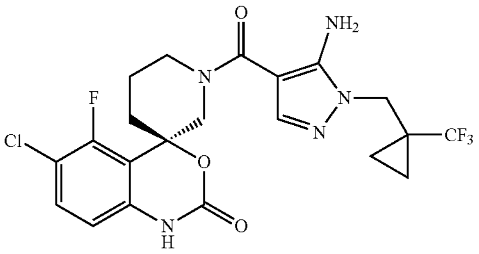 [SMILES: Nc1c(C(=O)N2CCC[C@@]3(C2)OC(=O)Nc2ccc(Cl)c(F)c23)cnn1CC1(C(F)(F)F)CC1] | (R)-1'-(5-Amino-1-((1-(trifluoromethyl)cyclopropyl)methyl)-1H-pyrazole-4-carbonyl)-6-chloro-5-fluorospiro[benzo[d][1,3]oxazine-4,3'-piperidin]-2(1H)-one | Calcd. 502.1, found 502.4 |
| 27 | 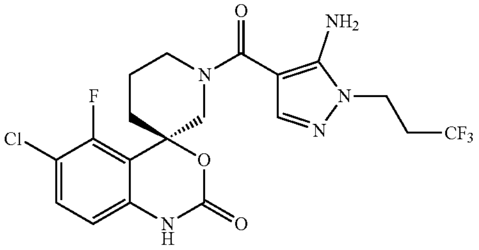 [SMILES: Nc1c(C(=O)N2CCC[C@@]3(C2)OC(=O)Nc2ccc(Cl)c(F)c23)cnn1CCC(F)(F)F] | (R)-1'-(5-Amino-1-(3,3,3-trifluoropropyl)-1H-pyrazole-4-carbonyl)-6-chloro-5-fluorospiro[benzo[d][1,3]oxazine-4,3'-piperidin]-2(1H)-one | Calcd. 476.1, found 476.4 |
| 28 | 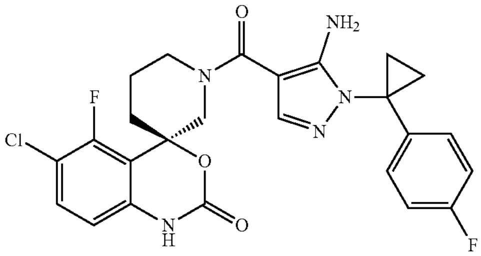 [SMILES: Nc1c(C(=O)N2CCC[C@@]3(C2)OC(=O)Nc2ccc(Cl)c(F)c23)cnn1C1(c2ccc(F)cc2)CC1] | (R)-1'-(5-Amino-1-(1-(4-fluorophenyl)cyclopropyl)-1H-pyrazole-4-carbonyl)-6-chloro-5-fluorospiro[benzo[d][1,3]oxazine-4,3'-piperidin]-2(1H)-one | Calcd. 514.1, found 514.1 |
| 29 | 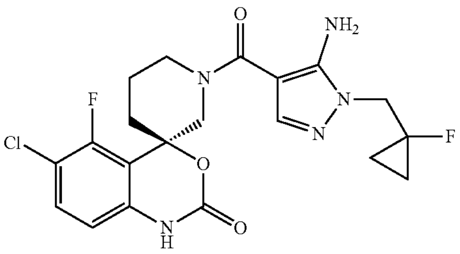 [SMILES: Nc1c(C(=O)N2CCC[C@@]3(C2)OC(=O)Nc2ccc(Cl)c(F)c23)cnn1CC1(F)CC1] | (R)-1'-(5-Amino-1-((1-fluorocyclopropyl)methyl)-1H-pyrazole-4-carbonyl)-6-chloro-5-fluorospiro[benzo[d][1,3]oxazine-4,3'-piperidin]-2(1H)-one | Calcd. 452.1, found 452.4 |

TABLE 1-continued

Following procedures similar to those described for Examples 1-4, the following compounds were prepared using appropriate starting materials.

| Example | Structure | Name | Exact Mass $[M + H]^+$ |
|---|---|---|---|
| 30 | 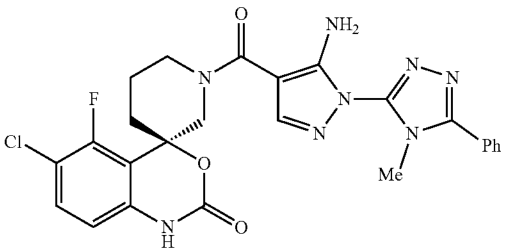 [SMILES: Cn1c(-c2ccccc2)nnc1-n1ncc(C(=O)N2CCC[C@@]3(C2)OC(=O)Nc2ccc(Cl)c(F)c23)c1N] | (R)-1'-(5-Amino-1-(4-methyl-5-phenyl-4H-1,2,4-triazol-3-yl)-1H-pyrazole-4-carbonyl)-6-chloro-5-fluorospiro[benzo[d][1,3]oxazine-4,3'-piperidin]-2(1H)-one | Calcd. 537.2, found 537.2 |
| 31 | 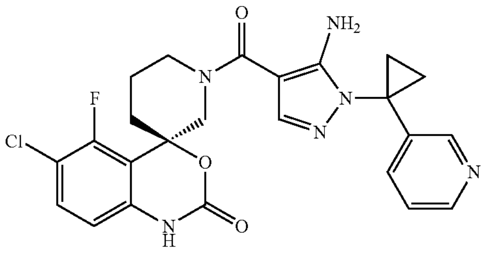 [SMILES: Nc1c(C(=O)N2CCC[C@@]3(C2)OC(=O)Nc2ccc(Cl)c(F)c23)cnn1C1(c2cccnc2)CC1] | (R)-1'-(5-Amino-1-(pyridin-3-ylmethyl)-1H-pyrazole-4-carbonyl)-6-chloro-5-fluorospiro[benzo[d][1,3]oxazine-4,3'-piperidin]-2(1H)-one | Calcd. 471.1, found 471.1 |
| 32 | 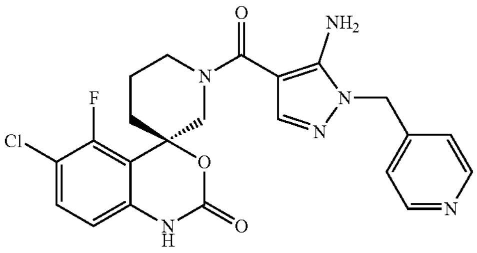 [SMILES: Nc1c(C(=O)N2CCC[C@@]3(C2)OC(=O)Nc2ccc(Cl)c(F)c23)cnn1Cc1ccncc1] | (R)-1'-(5-Amino-1-(pyridin-4-ylmethyl)-1H-pyrazole-4-carbonyl)-6-chloro-5-fluorospiro[benzo[d][1,3]oxazine-4,3'-piperidin]-2(1H)-one | Calcd. 471.1, found 471.1 |
| 33 | 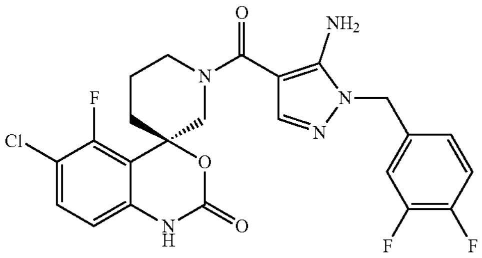 [SMILES: Nc1c(C(=O)N2CCC[C@@]3(C2)OC(=O)Nc2ccc(Cl)c(F)c23)cnn1Cc1ccc(F)c(F)c1] | (R)-1'-(5-Amino-1-(3,4-difluorobenzyl)-1H-pyrazole-4-carbonyl)-6-chloro-5-fluorospiro[benzo[d][1,3]oxazine-4,3'-piperidin]-2(1H)-one | Calcd. 506.1, found 506.1 |
| 34 | 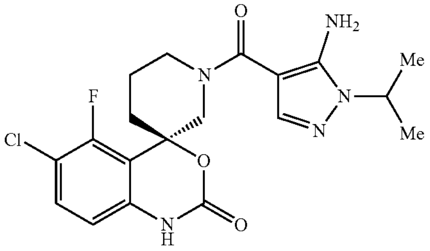 [SMILES: CC(C)n1ncc(C(=O)N2CCC[C@@]3(C2)OC(=O)Nc2ccc(Cl)c(F)c23)c1N] | (R)-1'-(5-Amino-1-isopropyl-1H-pyrazole-4-carbonyl)-6-chloro-5-fluorospiro[benzo[d][1,3]oxazine-4,3'-piperidin]-2(1H)-one | Calcd. 422.1, found 422.1 |

TABLE 1-continued

Following procedures similar to those described for Examples 1-4, the following compounds were prepared using appropriate starting materials.

| Example | Structure | Name | Exact Mass $[M + H]^+$ |
|---|---|---|---|
| 35 | 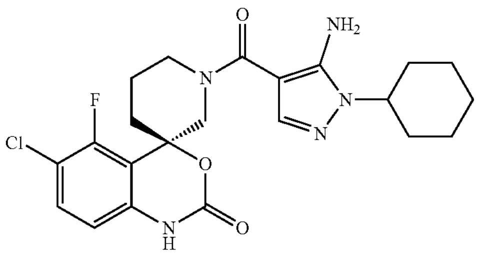 [SMILES: Nc1c(C(=O)N2CCC[C@@]3(C2)OC(=O)Nc2ccc(Cl)c(F)c23)cnn1C1CCCCC1] | (R)-1'-(5-Amino-1-cyclohexyl-1H-pyrazole-4-carbonyl)-6-chloro-5-fluorospiro[benzo[d][1,3]oxazine-4,3'-piperidin]-2(1H)-one | Calcd. 462.2, found 462.2 |
| 36 | 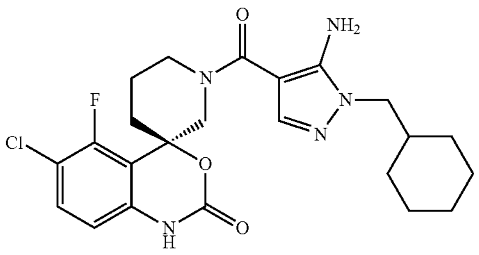 [SMILES: Nc1c(C(=O)N2CCC[C@@]3(C2)OC(=O)Nc2ccc(Cl)c(F)c23)cnn1CC1CCCCC1] | (R)-1'-(5-Amino-1-(cyclohexylmethyl)-1H-pyrazole-4-carbonyl)-6-chloro-5-fluorospiro[benzo[d][1,3]oxazine-4,3'-piperidin]-2(1H)-one | Calcd. 476.2, found 476.2 |
| 37 | 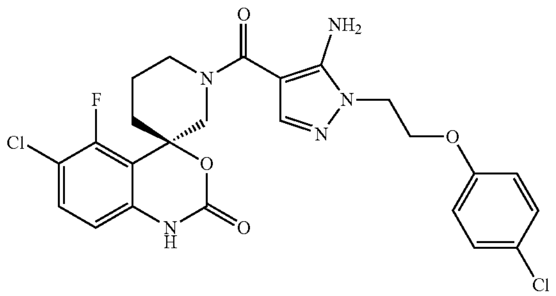 [SMILES: Nc1c(C(=O)N2CCC[C@@]3(C2)OC(=O)Nc2ccc(Cl)c(F)c23)cnn1CCOc1ccc(Cl)cc1] | (R)-1'-(5-Amino-1-(2-(4-chlorophenoxy)ethyl)-1H-pyrazole-4-carbonyl)-6-chloro-5-fluorospiro[benzo[d][1,3]oxazine-4,3'-piperidin]-2(1H)-one | Calcd. 534.1, found 534.1 |
| 38 | 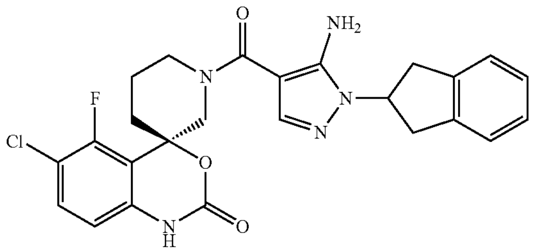 [SMILES: Nc1c(C(=O)N2CCC[C@@]3(C2)OC(=O)Nc2ccc(Cl)c(F)c23)cnn1C1Cc2ccccc2C1] | (R)-1'-(5-Amino-1-(2,3-dihydro-1H-inden-2-yl)-1H-pyrazole-4-carbonyl)-6-chloro-5-fluorospiro[benzo[d][1,3]oxazine-4,3'-piperidin]-2(1H)-one | Calcd. 496.2, found 496.2 |
| 39 | 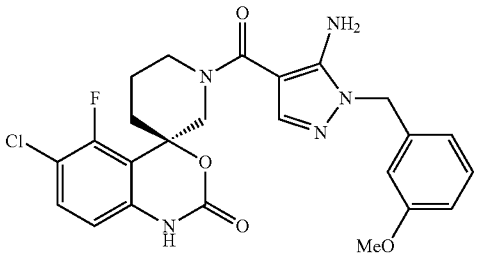 [SMILES: COc1cccc(Cn2ncc(C(=O)N3CCC[C@@]4(C3)OC(=O)Nc3ccc(Cl)c(F)c34)c2N)c1] | (R)-1'-(5-Amino-1-(3-methoxybenzyl)-1H-pyrazole-4-carbonyl)-6-chloro-5-fluorospiro[benzo[d][1,3]oxazine-4,3'-piperidin]-2(1H)-one | Calcd. 500.1, found 500.1 |

TABLE 1-continued

Following procedures similar to those described for Examples 1-4, the following compounds were prepared using appropriate starting materials.

| Example | Structure | Name | Exact Mass $[M + H]^+$ |
|---|---|---|---|
| 40 | 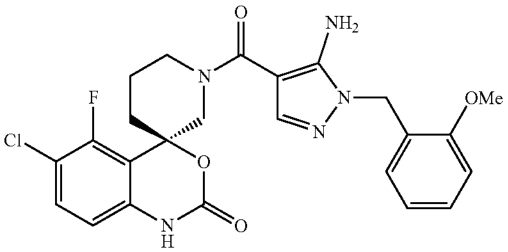 [SMILES: COc1ccccc1Cn1ncc(C(=O)N2CCC[C@@]3(C2)OC(=O)Nc2ccc(Cl)c(F)c23)c1N] | (R)-1'-(5-Amino-1-(2-methoxybenzyl)-1H-pyrazole-4-carbonyl)-6-chloro-5-fluorospiro[benzo[d][1,3]oxazine-4,3'-piperidin]-2(1H)-one | Calcd. 500.1, found 500.1 |
| 41 | 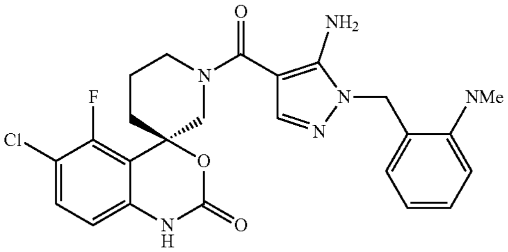 | (R)-1'-(5-Amino-1-(2-(dimethylamino)benzyl)-1H-pyrazole-4-carbonyl)-6-chloro-5-fluorospiro[benzo[d][1,3]oxazine-4,3'-piperidin]-2(1H)-one | Calcd. 513.2, found 513.2 |
| 42 | 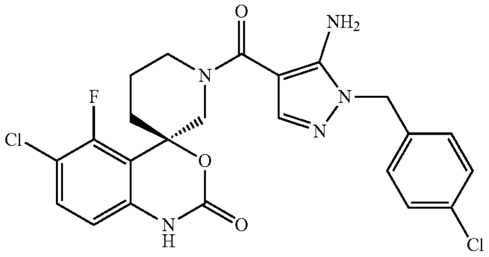 [SMILES: Nc1c(C(=O)N2CCC[C@@]3(C2)OC(=O)Nc2ccc(Cl)c(F)c23)cnn1Cc1ccc(Cl)cc1] | (R)-1'-(5-Amino-1-(4-chlorobenzyl)-1H-pyrazole-4-carbonyl)-6-chloro-5-fluorospiro[benzo[d][1,3]oxazine-4,3'-piperidin]-2(1H)-one | Calcd. 504.1, found 504.1 |
| 43 | 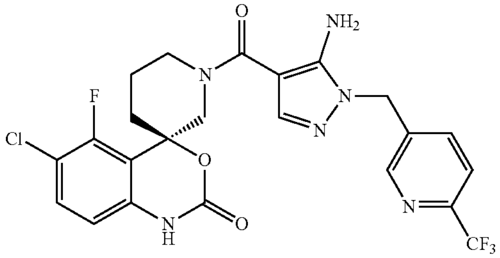 [SMILES: Nc1c(C(=O)N2CCC[C@@]3(C2)OC(=O)Nc2ccc(Cl)c(F)c23)cnn1Cc1ccc(C(F)(F)F)nc1] | (R)-1'-(5-Amino-1-((6-(trifluoromethyl)pyridin-3-yl)methyl)-1H-pyrazole-4-carbonyl)-6-chloro-5-fluorospiro[benzo[d][1,3]oxazine-4,3'-piperidin]-2(1H)-one | Calcd. 539.1, found 539.1 |
| 44 | 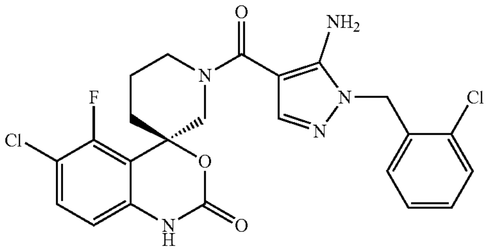 [SMILES: Nc1c(C(=O)N2CCC[C@@]3(C2)OC(=O)Nc2ccc(Cl)c(F)c23)cnn1Cc1ccccc1Cl] | (R)-1'-(5-Amino-1-(2-chlorobenzyl)-1H-pyrazole-4-carbonyl)-6-chloro-5-fluorospiro[benzo[d][1,3]oxazine-4,3'-piperidin]-2(1H)-one | Calcd. 504.1, found 504.1 |

TABLE 1-continued

| Example | Structure | Name | Exact Mass [M + H]$^+$ |
| --- | --- | --- | --- |
| | Following procedures similar to those described for Examples 1-4, the following compounds were prepared using appropriate starting materials. | | |
| 45 | 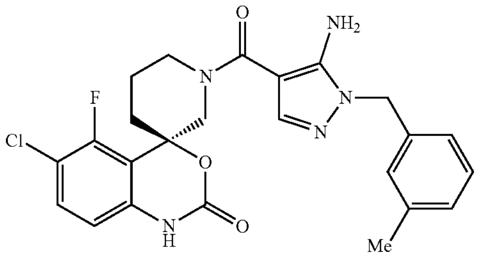 | (R)-1'-(5-Amino-1-(3-methylbenzyl)-1H-pyrazole-4-carbonyl)-6-chloro-5-fluorospiro[benzo[d][1,3]oxazine-4,3'-piperidin]-2(1H)-one | Calcd. 484.2, found 484.2 |
| 46 | 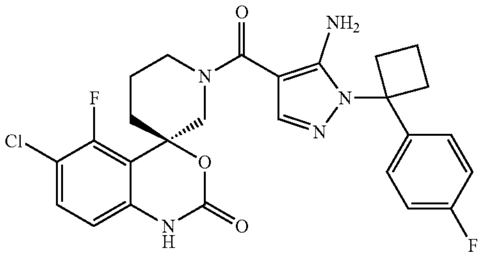 [SMILES: Nc1c(C(=O)N2CCC[C@@]3(C2)OC(=O)Nc2ccc(Cl)c(F)c23)cnn1C1(c2ccc(F)cc2)CCC1] | (R)-1'-(5-Amino-1-(1-(4-fluorophenyl)cyclobutyl)-1H-pyrazole-4-carbonyl)-6-chloro-5-fluorospiro[benzo[d][1,3]oxazine-4,3'-piperidin]-2(1H)-one | Calcd. 528.2, found 528.4 |
| 47 | 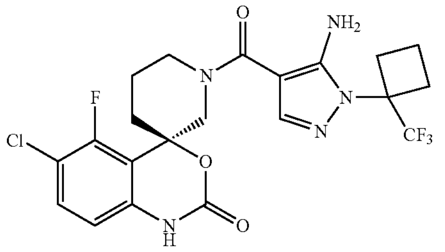 [SMILES: Nc1c(C(=O)N2CCC[C@@]3(C2)OC(=O)Nc2ccc(Cl)c(F)c23)cnn1C1(C(F)(F)F)CCC1] | (R)-1'-(5-Amino-1-(1-(trifluoromethyl)cyclobutyl)-1H-pyrazole-4-carbonyl)-6-chloro-5-fluorospiro[benzo[d][1,3]oxazine-4,3'-piperidin]-2(1H)-one | Calcd. 502.1, found 502.4 |
| 48 | 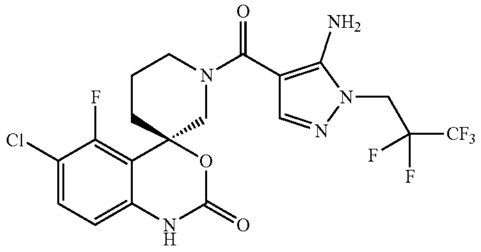 [SMILES: Nc1c(C(=O)N2CCC[C@@]3(C2)OC(=O)Nc2ccc(Cl)c(F)c23)cnn1CC(F)(F)C(F)(F)F] | (R)-1'-(5-Amino-1-(2,2,3,3,3-pentafluoropropyl)-1H-pyrazole-4-carbonyl)-6-chloro-5-fluorospiro[benzo[d][1,3]oxazine-4,3'-piperidin]-2(1H)-one | Calcd. 512.1, found 512.3 |
| 49 | 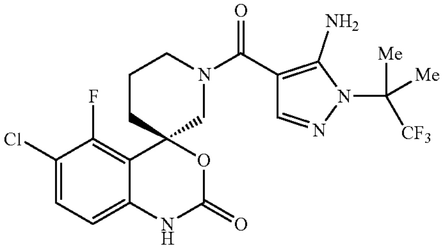 [SMILES: CC(C)(n1ncc(C(=O)N2CCC[C@@]3(C2)OC(=O)Nc2ccc(Cl)c(F)c23)c1N)C(F)(F)F] | (R)-1'-(5-Amino-1-(1,1,1-trifluoro-2-methylpropan-2-yl)-1H-pyrazole-4-carbonyl)-6-chloro-5-fluorospiro[benzo[d][1,3]oxazine-4,3'-piperidin]-2(1H)-one | Calcd. 490.1, found 490.1 |

TABLE 1-continued

Following procedures similar to those described for Examples 1-4, the following compounds were prepared using appropriate starting materials.

| Example | Structure | Name | Exact Mass [M + H]+ |
|---|---|---|---|
| 50 | 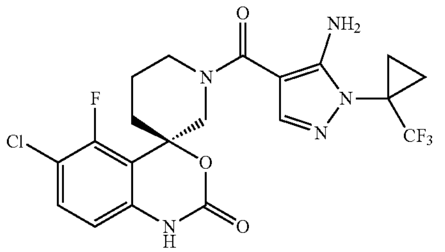 [SMILES: Nc1c(C(=O)N2CCC[C@@]3(C2)OC(=O)Nc2ccc(Cl)c(F)c23)cnn1C1(C(F)(F)F)CC1] | (R)-1'-(5-Amino-1-(1-(trifluoromethyl)cyclopropyl)-1H-pyrazole-4-carbonyl)-6-chloro-5-fluorospiro[benzo[d][1,3]oxazine-4,3'-piperidin]-2(1H)-one | Calcd. 488.1, found 488.1 |
| 51 | 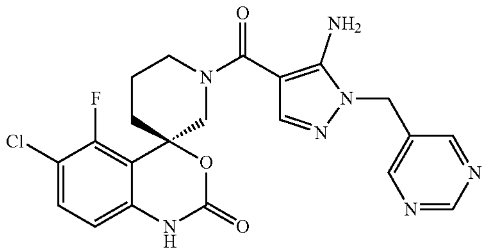 [SMILES: Nc1c(C(=O)N2CCC[C@@]3(C2)OC(=O)Nc2ccc(Cl)c(F)c23)cnn1Cc1cncnc1] | (R)-1'-(5-Amino-1-(pyrimidin-5-ylmethyl)-1H-pyrazole-4-carbonyl)-6-chloro-5-fluorospiro[benzo[d][1,3]oxazine-4,3'-piperidin]-2(1H)-one | Calcd. 472.1, found 472.2 |
| 52 | 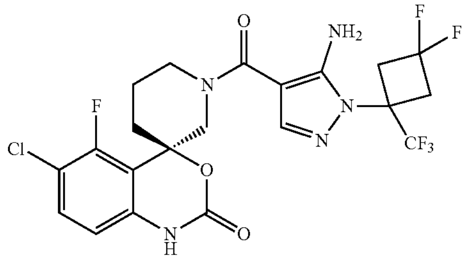 [SMILES: Nc1c(C(=O)N2CCC[C@@]3(C2)OC(=O)Nc2ccc(Cl)c(F)c23)cnn1C1(C(F)(F)F)CC(F)(F)C1] | (R)-1'-(5-Amino-1-(3,3-difluoro-1-(trifluoromethyl)cyclobutyl)-1H-pyrazole-4-carbonyl)-6-chloro-5-fluorospiro[benzo[d][1,3]oxazine-4,3'-piperidin]-2(1H)-one | Calcd. 538.1, found 538.0 |
| 53 | 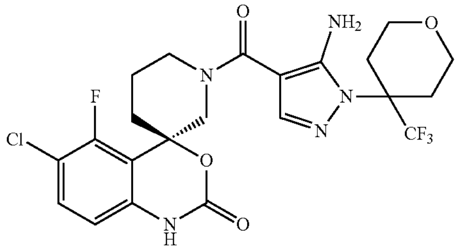 [SMILES: Nc1c(C(=O)N2CCC[C@@]3(C2)OC(=O)Nc2ccc(Cl)c(F)c23)cnn1C1(C(F)(F)F)CCOCC1] | (R)-1'-(5-Amino-1-(4-(trifluoromethyl)tetrahydro-2H-pyran-4-yl)-1H-pyrazole-4-carbonyl)-6-chloro-5-fluorospiro[benzo[d][1,3]oxazine-4,3'-piperidin]-2(1H)-one | Calcd. 532.1, found 532.1 |
| 54 | 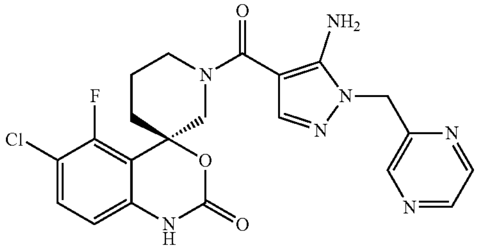 [SMILES: Nc1c(C(=O)N2CCC[C@@]3(C2)OC(=O)Nc2ccc(Cl)c(F)c23)cnn1Cc1cnccn1] | (R)-1'-(5-Amino-1-(pyrazin-2-ylmethyl)-1H-pyrazole-4-carbonyl)-6-chloro-5-fluorospiro[benzo[d][1,3]oxazine-4,3'-piperidin]-2(1H)-one | Calcd. 472.1, found 472.0 |

TABLE 1-continued

Following procedures similar to those described for Examples 1-4, the following compounds were prepared using appropriate starting materials.

| Example | Structure | Name | Exact Mass $[M + H]^+$ |
|---|---|---|---|
| 55 | 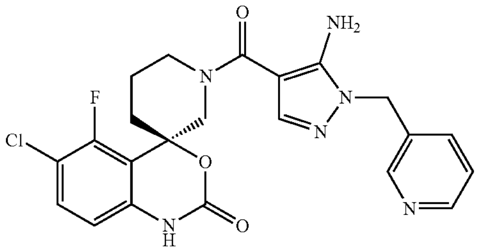 [SMILES: Nc1c(C(=O)N2CCC[C@@]3(C2)OC(=O)Nc2ccc(Cl)c(F)c23)cnn1Cc1cccnc1] | (R)-1'-(5-Amino-1-(pyridin-3-ylmethyl)-1H-pyrazole-4-carbonyl)-6-chloro-5-fluorospiro[benzo[d][1,3]oxazine-4,3'-piperidin]-2(1H)-one | Calcd. 471.1, found 471.1 |
| 56 | 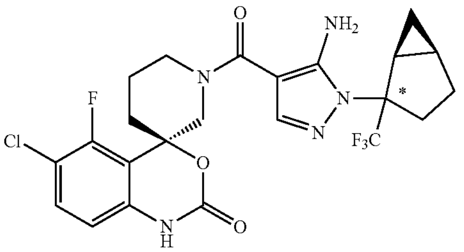 [SMILES: Nc1c(C(=O)N2CCC[C@@]3(C2)OC(=O)Nc2ccc(Cl)c(F)c23)cnn1C1(C(F)(F)F)CC[C@@H]2C[C@@H]21] | (R)-1'-(5-Amino-1-((1S,2S or R,5R)-2-(trifluoromethyl)bicyclo[3.1.0]hexan-2-yl)-1H-pyrazole-4-carbonyl)-6-chloro-5-fluorospiro[benzo[d][1,3]oxazine-4,3'-piperidin]-2(1H)-one | Calcd. 528.1, found 528.4 |
| 57 | 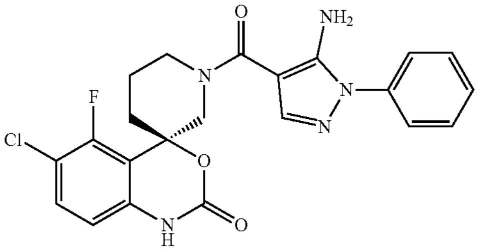 [SMILES: Nc1c(C(=O)N2CCC[C@@]3(C2)OC(=O)Nc2ccc(Cl)c(F)c23)cnn1-c1ccccc1] | (R)-1'-(5-Amino-1-phenyl-1H-pyrazole-4-carbonyl)-6-chloro-5-fluorospiro[benzo[d][1,3]oxazine-4,3'-piperidin]-2(1H)-one | Calcd. 456.1, found 456.4 |
| 58 | 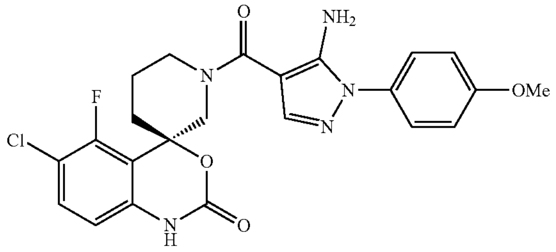 [SMILES: COc1ccc(-n2ncc(C(=O)N3CCC[C@@]4(C3)OC(=O)Nc3ccc(Cl)c(F)c34)c2N)cc1] | (R)-1'-(5-Amino-1-(4-methoxyphenyl)-1H-pyrazole-4-carbonyl)-6-chloro-5-fluorospiro[benzo[d][1,3]oxazine-4,3'-piperidin]-2(1H)-one | Calcd. 486.1, found 485.9 |
| 59 | 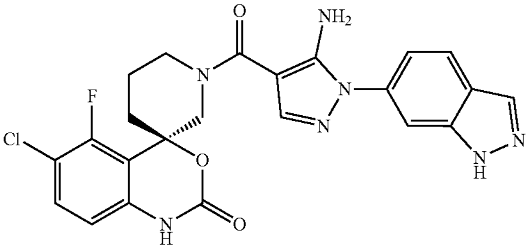 [SMILES: Nc1c(C(=O)N2CCC[C@@]3(C2)OC(=O)Nc2ccc(Cl)c(F)c23)cnn1-c1ccc2cn[nH]c2c1] | (R)-1'-(5-Amino-1-(1H-indazol-6-yl)-1H-pyrazole-4-carbonyl)-6-chloro-5-fluorospiro[benzo[d][1,3]oxazine-4,3'-piperidin]-2(1H)-one | Calcd. 496.1, found 495.9 |

TABLE 1-continued

| Following procedures similar to those described for Examples 1-4, the following compounds were prepared using appropriate starting materials. | | | |
|---|---|---|---|
| Example | Structure | Name | Exact Mass $[M + H]^+$ |
| 60 | 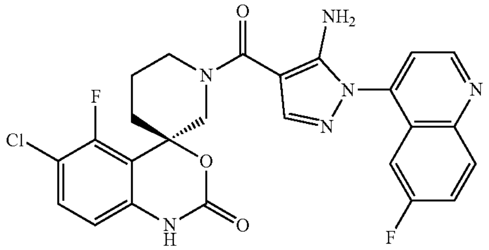 [SMILES: Nc1c(C(=O)N2CCC[C@@]3(C2)OC(=O)Nc2ccc(Cl)c(F)c23)cnn1-c1ccnc2ccc(F)cc12] | (R)-1'-(5-Amino-1-(6-fluoroquinolin-4-yl)-1H-pyrazole-4-carbonyl)-6-chloro-5-fluorospiro[benzo[d][1,3]oxazine-4,3'-piperidin]-2(1H)-one | Calcd. 525.1, found 524.9 |
| 61 | 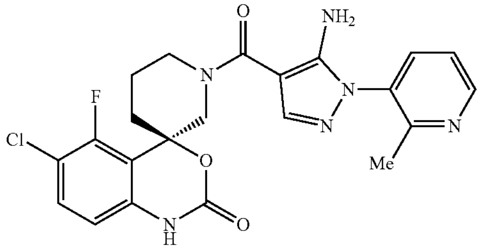 [SMILES: Cc1ncccc1-n1ncc(C(=O)N2CCC[C@@]3(C2)OC(=O)Nc2ccc(Cl)c(F)c23)c1N] | (R)-1'-(5-Amino-1-(2-methylpyridin-3-yl)-1H-pyrazole-4-carbonyl)-6-chloro-5-fluorospiro[benzo[d][1,3]oxazine-4,3'-piperidin]-2(1H)-one | Calcd. 471.1, found 470.1 |
| 62 | 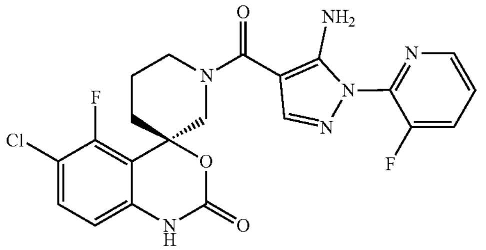 [SMILES: Nc1c(C(=O)N2CCC[C@@]3(C2)OC(=O)Nc2ccc(Cl)c(F)c23)cnn1-c1ncccc1F] | (R)-1'-(5-Amino-1-(3-fluoropyridin-2-yl)-1H-pyrazole-4-carbonyl)-6-chloro-5-fluorospiro[benzo[d][1,3]oxazine-4,3'-piperidin]-2(1H)-one | Calcd. 475.1, found 475.0 |
| 63 | 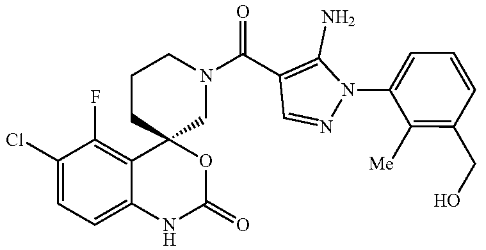 [SMILES: Cc1c(CO)cccc1-n1ncc(C(=O)N2CCC[C@@]3(C2)OC(=O)Nc2ccc(Cl)c(F)c23)c1N] | (R)-1'-(5-Amino-1-(3-(hydroxymethyl)-2-methylphenyl)-1H-pyrazole-4-carbonyl)-6-chloro-5-fluorospiro[benzo[d][1,3]oxazine-4,3'-piperidin]-2(1H)-one | Calcd. 500.1, found 500.1 |
| 64 | 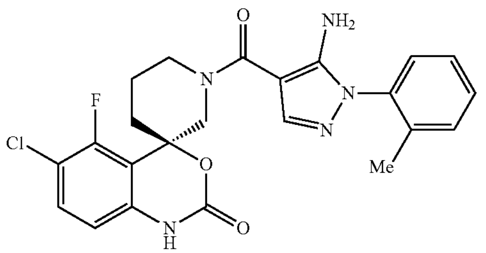 | (R)-1'-(5-Amino-1-(o-tolyl)-1H-pyrazole-4-carbonyl)-6-chloro-5-fluorospiro[benzo[d][1,3]oxazine-4,3'-piperidin]-2(1H)-one | Calcd. 470.1, found 469.9 |

TABLE 1-continued

| Following procedures similar to those described for Examples 1-4, the following compounds were prepared using appropriate starting materials. | | | |
|---|---|---|---|
| Example | Structure | Name | Exact Mass $[M + H]^+$ |
| 65 | 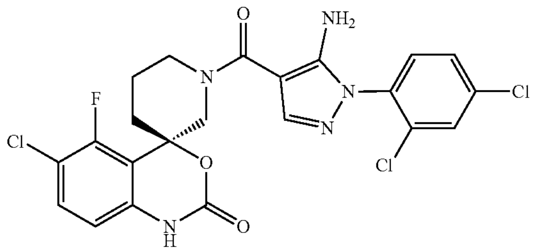 [SMILES: Nc1c(C(=O)N2CCC[C@@]3(C2)OC(=O)Nc2ccc(Cl)c(F)c23)cnn1-c1ccc(Cl)cc1Cl] | (R)-1'-(5-Amino-1-(2,4-dichlorophenyl)-1H-pyrazole-4-carbonyl)-6-chloro-5-fluorospiro[benzo[d][1,3]oxazine-4,3'-piperidin]-2(1H)-one | Calcd. 524.0, found 524.2 |
| 66 | 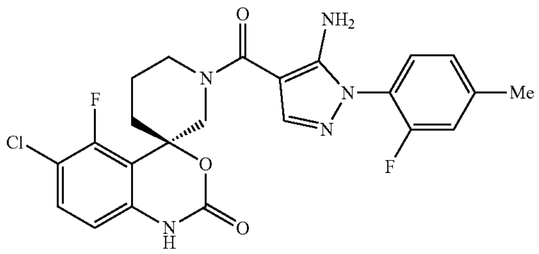 [SMILES: Cc1ccc(-n2ncc(C(=O)N3CCC[C@@]4(C3)OC(=O)Nc3ccc(Cl)c(F)c34)c2N)c(F)c1] | (R)-1'-(5-Amino-1-(2-fluoro-4-methylphenyl)-1H-pyrazole-4-carbonyl)-6-chloro-5-fluorospiro[benzo[d][1,3]oxazine-4,3'-piperidin]-2(1H)-one | Calcd. 488.1, found 488.3 |
| 67 | 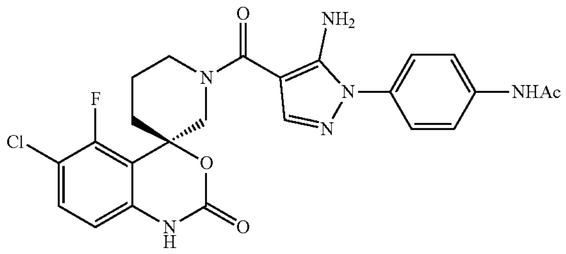 [SMILES: CC(=O)Nc1ccc(-n2ncc(C(=O)N3CCC[C@@]4(C3)OC(=O)Nc3ccc(Cl)c(F)c34)c2N)cc1] | (R)-N-(4-(5-Amino-4-(6-chloro-5-fluoro-2-oxo-1,2-dihydrospiro[benzo[d][1,3]oxazine-4,3'-piperidine]-1'-carbonyl)-1H-pyrazol-1-yl)phenyl)acetamide | Calcd. 513.1, found 513.3 |
| 68 | 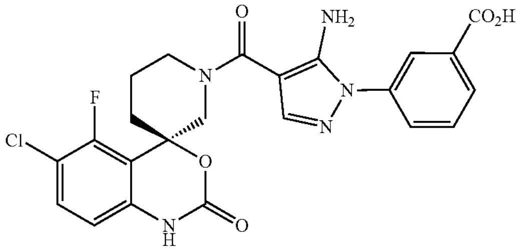 | (R)-3-(5-Amino-4-(6-chloro-5-fluoro-2-oxo-1,2-dihydrospiro[benzo[d][1,3]oxazine-4,3'-piperidine]-1'-carbonyl)-1H-pyrazol-1-yl)benzoic acid | Calcd. 500.1, found 500.4 |
| 69 | 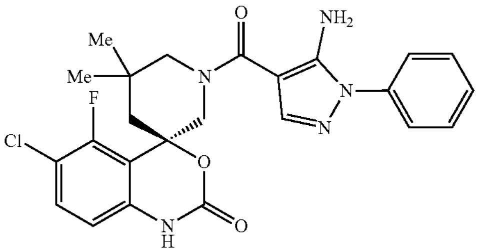 [SMILES: CC1(C)CN(C(=O)c2cnn(-c3ccccc3)c2N)C[C@]2(C1)OC(=O)Nc1ccc(Cl)c(F)c12] | (R)-1'-(5-Amino-1-phenyl-1H-pyrazole-4-carbonyl)-6-chloro-5-fluoro-5',5'-dimethylspiro[benzo[d][1,3]oxazine-4,3'-piperidin]-2(1H)-one | Calcd. 484.2, found 484.3 |

TABLE 1-continued

| Following procedures similar to those described for Examples 1-4, the following compounds were prepared using appropriate starting materials. | | | |
|---|---|---|---|
| Example | Structure | Name | Exact Mass [M + H]$^+$ |
| 70 | 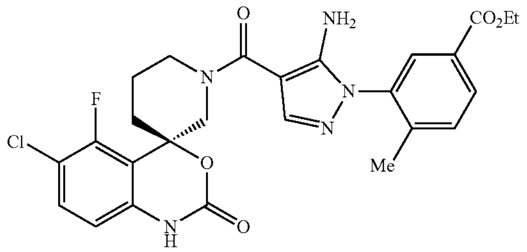 [SMILES: CCOC(=O)c1ccc(C)c(-n2ncc(C(=O)N3CCC[C@@]4(C3)OC(=O)Nc3ccc(Cl)c(F)c34)c2N)c1] | Ethyl (R)-3-(5-amino-4-(6-chloro-5-fluoro-2-oxo-1,2-dihydrospiro[benzo[d][1,3]oxazine-4,3'-piperidine]-1'-carbonyl)-1H-pyrazol-1-yl)-4-methylbenzoate | Calcd. 542.2, found 542.3 |
| 71 | 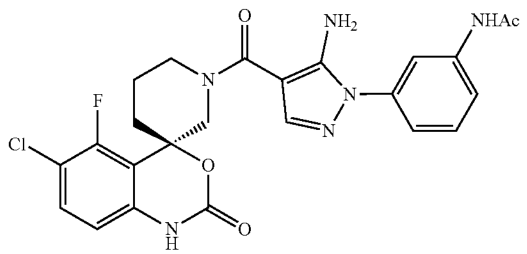 [SMILES: CC(=O)Nc1cccc(-n2ncc(C(=O)N3CCC[C@@]4(C3)OC(=O)Nc3ccc(Cl)c(F)c34)c2N)c1] | (R)-N-(3-(5-Amino-4-(6-chloro-5-fluoro-2-oxo-1,2-dihydrospiro[benzo[d][1,3]oxazine-4,3'-piperidine]-1'-carbonyl)-1H-pyrazol-1-yl)phenyl)acetamide | Calcd. 513.1, found 513.3 |
| 72 | 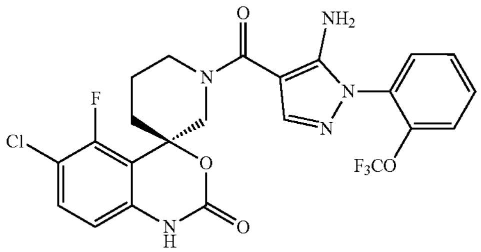 [SMILES: Nc1c(C(=O)N2CCC[C@@]3(C2)OC(=O)Nc2ccc(Cl)c(F)c23)cnn1-c1ccccc1OC(F)(F)F] | (R)-1'-(5-Amino-1-(2-(trifluoromethoxy)phenyl)-1H-pyrazole-4-carbonyl)-6-chloro-5-fluorospiro[benzo[d][1,3]oxazine-4,3'-piperidin]-2(1H)-one | Calcd. 540.1, found 540.0 |
| 73 | 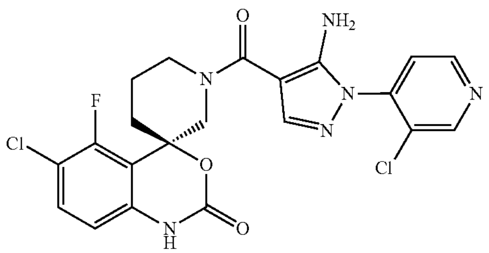 [SMILES: Nc1c(C(=O)N2CCC[C@@]3(C2)OC(=O)Nc2ccc(Cl)c(F)c23)cnn1-c1ccncc1Cl] | (R)-1'-(5-Amino-1-(3-chloropyridin-4-yl)-1H-pyrazole-4-carbonyl)-6-chloro-5-fluorospiro[benzo[d][1,3]oxazine-4,3'-piperidin]-2(1H)-one | Calcd. 491.1, found 491.3 |
| 74 | 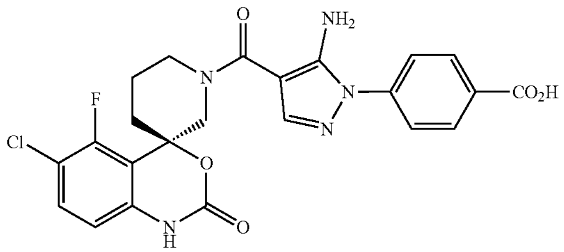 [SMILES: Nc1c(C(=O)N2CCC[C@@]3(C2)OC(=O)Nc2ccc(Cl)c(F)c23)cnn1-c1ccc(C(=O)O)cc1] | (R)-4-(5-Amino-4-(6-chloro-5-fluoro-2-oxo-1,2-dihydrospiro[benzo[d][1,3]oxazine-4,3'-piperidine]-1'-carbonyl)-1H-pyrazol-1-yl)benzoic acid | Calcd. 500.1, found 500.3 |

TABLE 1-continued

Following procedures similar to those described for Examples 1-4, the following compounds were prepared using appropriate starting materials.

| Example | Structure | Name | Exact Mass [M + H]$^+$ |
|---|---|---|---|
| 75 | 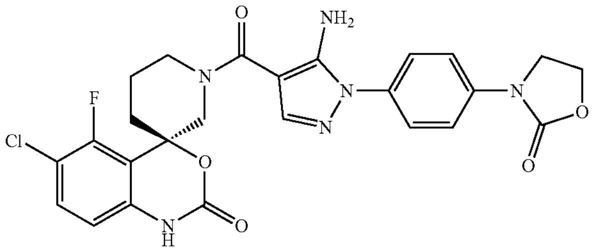 [SMILES: Nc1c(C(=O)N2CCC[C@@]3(C2)OC(=O)Nc2ccc(Cl)c(F)c23)cnn1-c1ccc(N2CCOC2=O)cc1] | (R)-1'-(5-Amino-1-(4-(2-oxooxazolidin-3-yl)phenyl)-1H-pyrazole-4-carbonyl)-6-chloro-5-fluorospiro[benzo[d][1,3]oxazine-4,3'-piperidin]-2(1H)-one | Calcd. 541.1, found 541.3 |
| 76 | 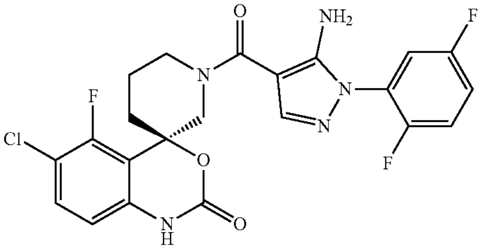 [SMILES: Nc1c(C(=O)N2CCC[C@@]3(C2)OC(=O)Nc2ccc(Cl)c(F)c23)cnn1-c1cc(F)ccc1F] | (R)-1'-(5-Amino-1-(2,5-difluorophenyl)-1H-pyrazole-4-carbonyl)-6-chloro-5-fluorospiro[benzo[d][1,3]oxazine-4,3'-piperidin]-2(1H)-one | Calcd. 492.1, found 492.3 |
| 77 | 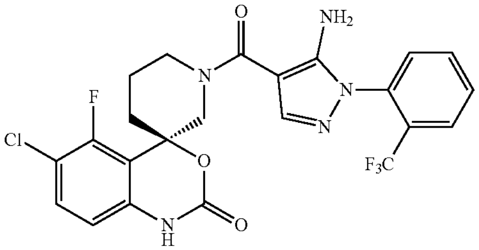 | (R)-1'-(5-Amino-1-(2-(trifluoromethyl)phenyl)-1H-pyrazole-4-carbonyl)-6-chloro-5-fluorospiro[benzo[d][1,3]oxazine-4,3'-piperidin]-2(1H)-one | Calcd. 524.1, found 524.3 |
| 78 | 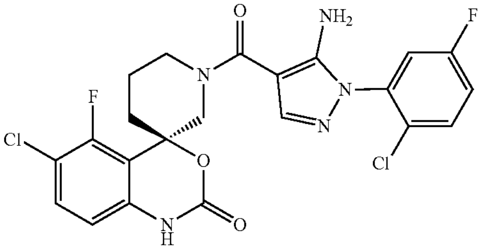 [SMILES: Nc1c(C(=O)N2CCC[C@@]3(C2)OC(=O)Nc2ccc(Cl)c(F)c23)cnn1-c1cc(F)ccc1Cl] | (R)-1'-(5-Amino-1-(2-chloro-5-fluorophenyl)-1H-pyrazole-4-carbonyl)-6-chloro-5-fluorospiro[benzo[d][1,3]oxazine-4,3'-piperidin]-2(1H)-one | Calcd. 508.1, found 508.2 |
| 79 | 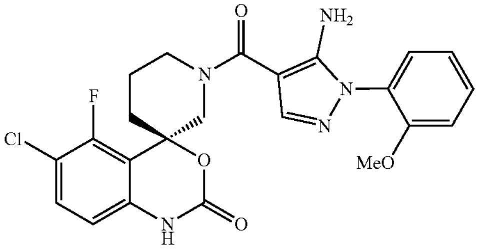 [SMILES: COc1ccccc1-n1ncc(C(=O)N2CCC[C@@]3(C2)OC(=O)Nc2ccc(Cl)c(F)c23)c1N] | (R)-1'-(5-Amino-1-(2-methoxyphenyl)-1H-pyrazole-4-carbonyl)-6-chloro-5-fluorospiro[benzo[d][1,3]oxazine-4,3'-piperidin]-2(1H)-one | Calcd. 486.1, found 486.0 |

TABLE 1-continued

Following procedures similar to those described for Examples 1-4, the following compounds were prepared using appropriate starting materials.

| Example | Structure | Name | Exact Mass [M + H]+ |
|---|---|---|---|
| 80 | 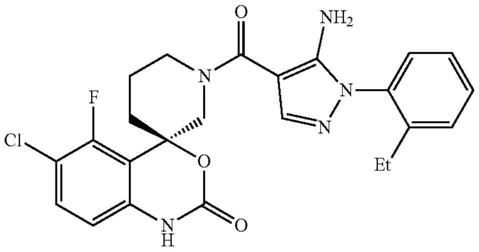 [SMILES: CCc1ccccc1-n1ncc(C(=O)N2CCC[C@@]3(C2)OC(=O)Nc2ccc(Cl)c(F)c23)c1N] | (R)-1'-(5-Amino-1-(2-ethylphenyl)-1H-pyrazole-4-carbonyl)-6-chloro-5-fluorospiro[benzo[d][1,3]oxazine-4,3'-piperidin]-2(1H)-one | Calcd. 484.2, found 484.4 |
| 81 | 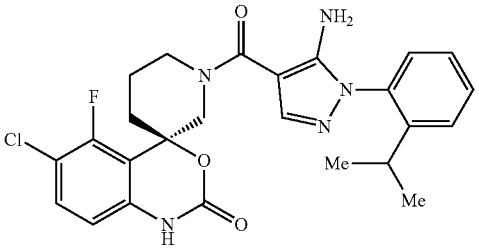 [SMILES: CC(C)c1ccccc1-n1ncc(C(=O)N2CCC[C@@]3(C2)OC(=O)Nc2ccc(Cl)c(F)c23)c1N] | (R)-1'-(5-Amino-1-(2-isopropylphenyl)-1H-pyrazole-4-carbonyl)-6-chloro-5-fluorospiro[benzo[d][1,3]oxazine-4,3'-piperidin]-2(1H)-one | Calcd. 498.2, found 498.4 |
| 82 | 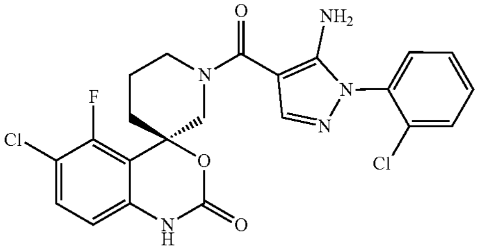 [SMILES: Nc1c(C(=O)N2CCC[C@@]3(C2)OC(=O)Nc2ccc(Cl)c(F)c23)cnn1-c1ccccc1Cl] | (R)-1'-(5-Amino-1-(2-chlorophenyl)-1H-pyrazole-4-carbonyl)-6-chloro-5-fluorospiro[benzo[d][1,3]oxazine-4,3'-piperidin]-2(1H)-one | Calcd. 490.1, found 490.3 |
| 83 | 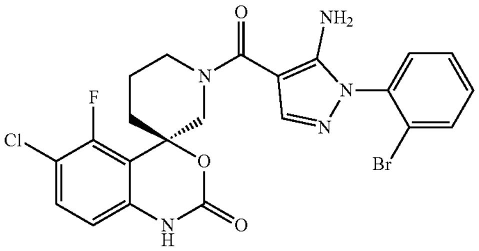 | (R)-1'-(5-Amino-1-(2-bromophenyl)-1H-pyrazole-4-carbonyl)-6-chloro-5-fluorospiro[benzo[d][1,3]oxazine-4,3'-piperidin]-2(1H)-one | Calcd. 534.0, found 534.2 |
| 84 | 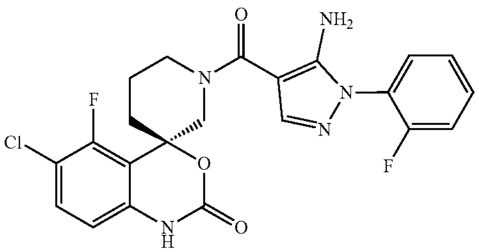 [SMILES: Nc1c(C(=O)N2CCC[C@@]3(C2)OC(=O)Nc2ccc(Cl)c(F)c23)cnn1-c1ccccc1F] | (R)-1'-(5-Amino-1-(2-fluorophenyl)-1H-pyrazole-4-carbonyl)-6-chloro-5-fluorospiro[benzo[d][1,3]oxazine-4,3'-piperidin]-2(1H)-one | Calcd. 474.1, found 474.4 |

TABLE 1-continued

Following procedures similar to those described for Examples 1-4, the following compounds were prepared using appropriate starting materials.

| Example | Structure | Name | Exact Mass [M + H]$^+$ |
|---|---|---|---|
| 85 | 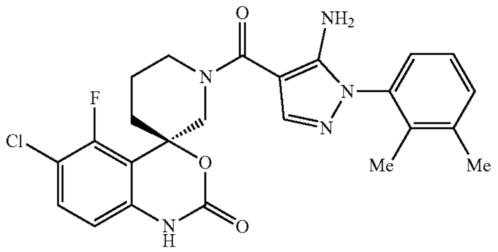 [SMILES: Cc1cccc(-n2ncc(C(=O)N3CCC[C@@]4(C3)OC(=O)Nc3ccc(Cl)c(F)c34)c2N)c1C] | (R)-1'-(5-Amino-1-(2,3-dimethylphenyl)-1H-pyrazole-4-carbonyl)-6-chloro-5-fluorospiro[benzo[d][1,3]oxazine-4,3'-piperidin]-2(1H)-one | Calcd. 484.2, found 484.4 |
| 86 | 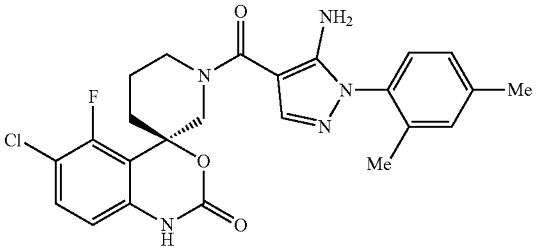 | (R)-1'-(5-Amino-1-(2,4-dimethylphenyl)-1H-pyrazole-4-carbonyl)-6-chloro-5-fluorospiro[benzo[d][1,3]oxazine-4,3'-piperidin]-2(1H)-one | Calcd. 484.2, found 484.4 |
| 87 | 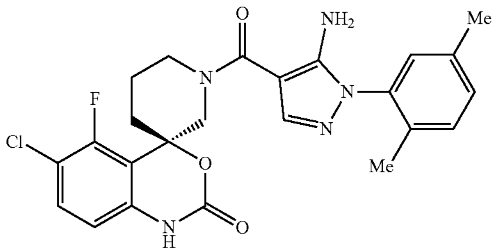 [SMILES: Cc1ccc(C)c(-n2ncc(C(=O)N3CCC[C@@]4(C3)OC(=O)Nc3ccc(Cl)c(F)c34)c2N)c1] | (R)-1'-(5-Amino-1-(2,5-dimethylphenyl)-1H-pyrazole-4-carbonyl)-6-chloro-5-fluorospiro[benzo[d][1,3]oxazine-4,3'-piperidin]-2(1H)-one | Calcd. 484.2, found 484.4 |
| 88 | 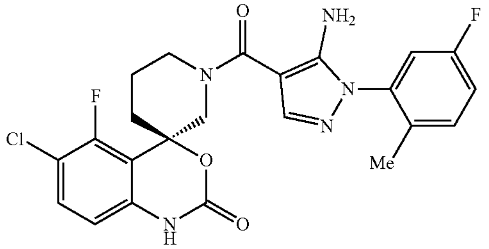 | (R)-1'-(5-Amino-1-(5-fluoro-2-methylphenyl)-1H-pyrazole-4-carbonyl)-6-chloro-5-fluorospiro[benzo[d][1,3]oxazine-4,3'-piperidin]-2(1H)-one | Calcd. 488.1, found 488.3 |
| 89 | 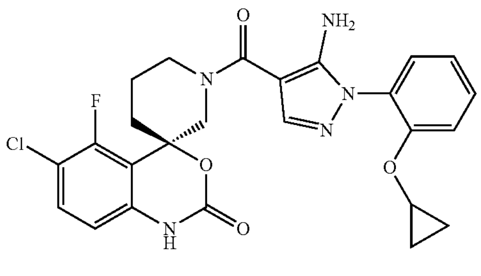 [SMILES: Nc1c(C(=O)N2CCC[C@@]3(C2)OC(=O)Nc2ccc(Cl)c(F)c23)cnn1-c1ccccc1OC1CC1] | (R)-1'-(5-Amino-1-(2-cyclopropoxyphenyl)-1H-pyrazole-4-carbonyl)-6-chloro-5-fluorospiro[benzo[d][1,3]oxazine-4,3'-piperidin]-2(1H)-one | Calcd. 512.1, found 512.9 |

TABLE 1-continued

| Example | Structure | Name | Exact Mass $[M + H]^+$ |
|---|---|---|---|
| Following procedures similar to those described for Examples 1-4, the following compounds were prepared using appropriate starting materials. | | | |
| 90 | 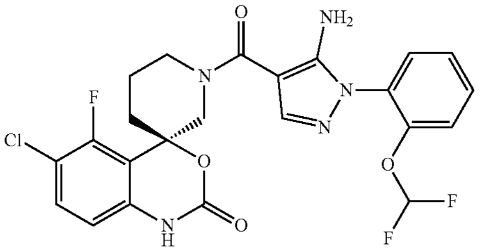 [SMILES: Nc1c(C(=O)N2CCC[C@@]3(C2)OC(=O)Nc2ccc(Cl)c(F)c23)cnn1-c1ccccc1OC(F)F] | (R)-1'-(5-Amino-1-(2-(difluoromethoxy)phenyl)-1H-pyrazole-4-carbonyl)-6-chloro-5-fluorospiro[benzo[d][1,3]oxazine-4,3'-piperidin]-2(1H)-one | Calcd. 522.1, found 522.0 |
| 91 | 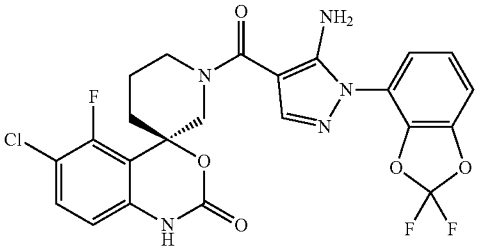 [SMILES: Nc1c(C(=O)N2CCC[C@@]3(C2)OC(=O)Nc2ccc(Cl)c(F)c23)cnn1-c1cccc2c1OC(F)(F)O2] | (R)-1'-(5-Amino-1-(2,2-difluorobenzo[d][1,3]dioxol-4-yl)-1H-pyrazole-4-carbonyl)-6-chloro-5-fluorospiro[benzo[d][1,3]oxazine-4,3'-piperidin]-2(1H)-one | Calcd. 536.1, found 536.3 |
| 92 | 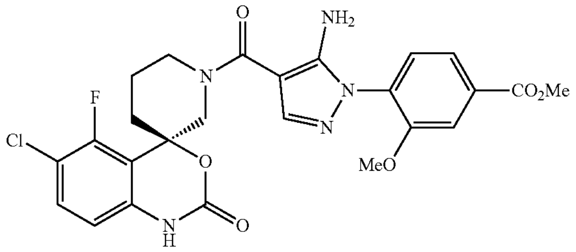 [SMILES: COC(=O)c1ccc(-n2ncc(C(=O)N3CCC[C@@]4(C3)OC(=O)Nc3ccc(Cl)c(F)c34)c2N)c(OC)c1] | Methyl (R)-4-(5-amino-4-(6-chloro-5-fluoro-2-oxo-1,2-dihydrospiro[benzo[d][1,3]oxazine-4,3'-piperidine]-1'-carbonyl)-1H-pyrazol-1-yl)-3-methoxybenzoate | Calcd. 544.1, found 544.3 |
| 93 | 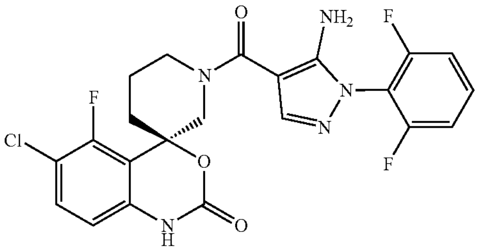 [SMILES: Nc1c(C(=O)N2CCC[C@@]3(C2)OC(=O)Nc2ccc(Cl)c(F)c23)cnn1-c1c(F)cccc1F] | (R)-1'-(5-Amino-1-(2,6-difluorophenyl)-1H-pyrazole-4-carbonyl)-6-chloro-5-fluorospiro[benzo[d][1,3]oxazine-4,3'-piperidin]-2(1H)-one | Calcd. 492.1, found 492.3 |
| 94 | 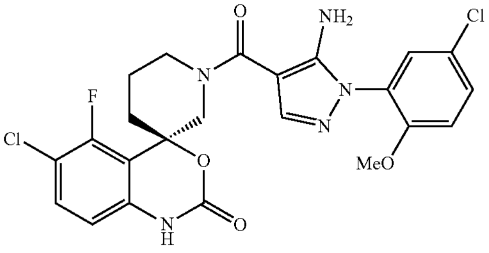 [SMILES: COc1ccc(Cl)cc1-n1ncc(C(=O)N2CCC[C@@]3(C2)OC(=O)Nc2ccc(Cl)c(F)c23)c1N] | (R)-1'-(5-Amino-1-(5-chloro-2-methoxyphenyl)-1H-pyrazole-4-carbonyl)-6-chloro-5-fluorospiro[benzo[d][1,3]oxazine-4,3'-piperidin]-2(1H)-one | Calcd. 520.1, found 520.3 |

TABLE 1-continued

| Following procedures similar to those described for Examples 1-4, the following compounds were prepared using appropriate starting materials. | | | |
|---|---|---|---|
| Example | Structure | Name | Exact Mass $[M + H]^+$ |
| 95 | 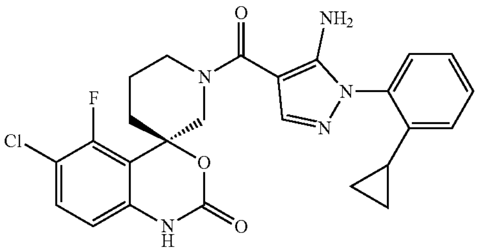 [SMILES: Nc1c(C(=O)N2CCC[C@@]3(C2)OC(=O)Nc2ccc(Cl)c(F)c23)cnn1-c1ccccc1C1CC1] | (R)-1'-(5-Amino-1-(2-cyclopropylphenyl)-1H-pyrazole-4-carbonyl)-6-chloro-5-fluorospiro[benzo[d][1,3]oxazine-4,3'-piperidin]-2(1H)-one | Calcd. 496.2, found 496.4 |
| 96 | 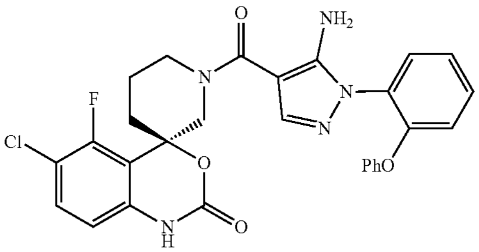 | (R)-1'-(5-Amino-1-(2-phenoxyphenyl)-1H-pyrazole-4-carbonyl)-6-chloro-5-fluorospiro[benzo[d][1,3]oxazine-4,3'-piperidin]-2(1H)-one | Calcd. 548.1, found 548.3 |
| 97 | 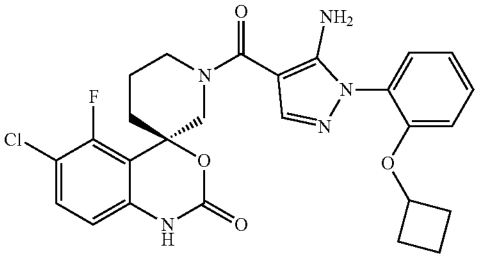 [SMILES: Nc1c(C(=O)N2CCC[C@@]3(C2)OC(=O)Nc2ccc(Cl)c(F)c23)cnn1-c1ccccc1OC1CCC1] | (R)-1'-(5-Amino-1-(2-cyclobutoxyphenyl)-1H-pyrazole-4-carbonyl)-6-chloro-5-fluorospiro[benzo[d][1,3]oxazine-4,3'-piperidin]-2(1H)-one | Calcd. 526.2, found 526.3 |
| 98 | 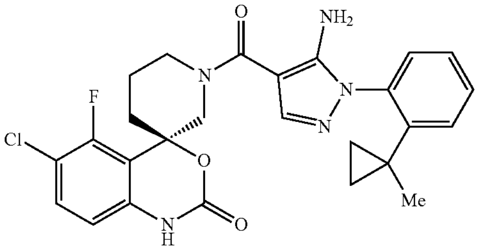 [SMILES: CC1(c2ccccc2-n2ncc(C(=O)N3CCC[C@@]4(C3)OC(=O)Nc3ccc(Cl)c(F)c34)c2N)CC1] | (R)-1'-(5-Amino-1-(2-(1-methylcyclopropyl)phenyl)-1H-pyrazole-4-carbonyl)-6-chloro-5-fluorospiro[benzo[d][1,3]oxazine-4,3'-piperidin]-2(1H)-one | Calcd. 510.2, found 510.4 |
| 99 | 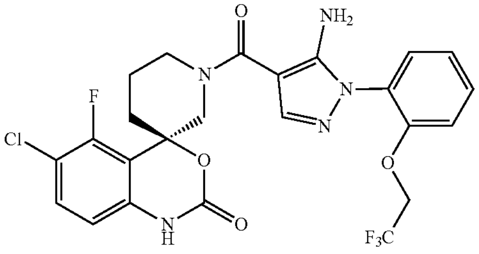 | (R)-1'-(5-Amino-1-(2-(2,2,2-trifluoroethoxy)phenyl)-1H-pyrazole-4-carbonyl)-6-chloro-5-fluorospiro[benzo[d][1,3]oxazine-4,3'-piperidin]-2(1H)-one | Calcd. 554.1, found 554.3 |

TABLE 1-continued

Following procedures similar to those described for Examples 1-4, the following compounds were prepared using appropriate starting materials.

| Example | Structure | Name | Exact Mass $[M + H]^+$ |
|---|---|---|---|
| 100 | 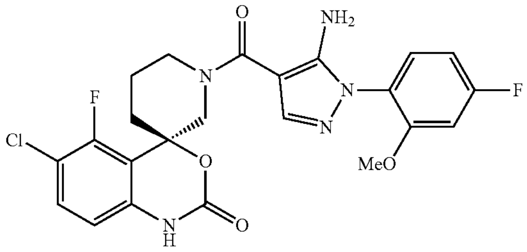 [SMILES: COc1cc(F)ccc1-n1ncc(C(=O)N2CCC[C@@]3(C2)OC(=O)Nc2ccc(Cl)c(F)c23)c1N] | (R)-1'-(5-Amino-1-(4-fluoro-2-methoxyphenyl)-1H-pyrazole-4-carbonyl)-6-chloro-5-fluorospiro[benzo[d][1,3]oxazine-4,3'-piperidin]-2(1H)-one | Calcd. 504.1, found 504.3 |
| 101 | 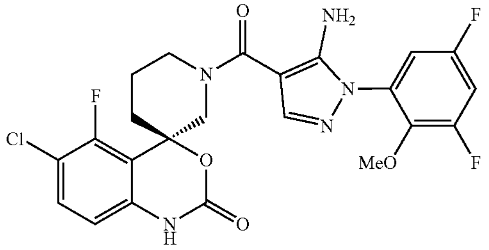 [SMILES: COc1c(F)cc(F)cc1-n1ncc(C(=O)N2CCC[C@@]3(C2)OC(=O)Nc2ccc(Cl)c(F)c23)c1N] | (R)-1'-(5-Amino-1-(3,5-difluoro-2-methoxyphenyl)-1H-pyrazole-4-carbonyl)-6-chloro-5-fluorospiro[benzo[d][1,3]oxazine-4,3'-piperidin]-2(1H)-one | Calcd. 522.1, found 522.3 |
| 102 | 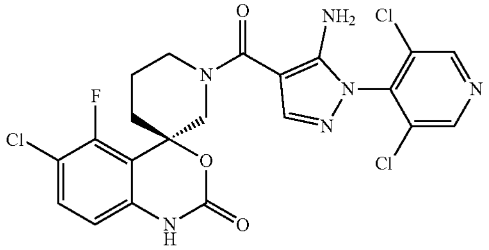 [SMILES: Nc1c(C(=O)N2CCC[C@@]3(C2)OC(=O)Nc2ccc(Cl)c(F)c23)cnn1-c1c(Cl)cncc1Cl] | (R)-1'-(5-Amino-1-(3,5-dichloropyridin-4-yl)-1H-pyrazole-4-carbonyl)-6-chloro-5-fluorospiro[benzo[d][1,3]oxazine-4,3'-piperidin]-2(1H)-one | Calcd. 525.0, found 525.0 |
| 103 | 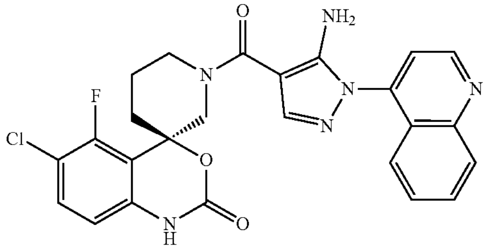 [SMILES: Nc1c(C(=O)N2CCC[C@@]3(C2)OC(=O)Nc2ccc(Cl)c(F)c23)cnn1-c1ccnc2ccccc12] | (R)-1'-(5-Amino-1-(quinolin-4-yl)-1H-pyrazole-4-carbonyl)-6-chloro-5-fluorospiro[benzo[d][1,3]oxazine-4,3'-piperidin]-2(1H)-one | Calcd. 507.1, found 507.1 |
| 104 | 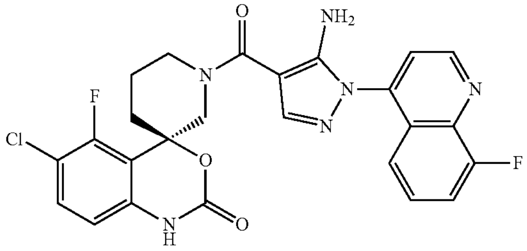 [SMILES: Nc1c(C(=O)N2CCC[C@@]3(C2)OC(=O)Nc2ccc(Cl)c(F)c23)cnn1-c1ccnc2c(F)cccc12] | (R)-1'-(5-Amino-1-(8-fluoroquinolin-4-yl)-1H-pyrazole-4-carbonyl)-6-chloro-5-fluorospiro[benzo[d][1,3]oxazine-4,3'-piperidin]-2(1H)-one | Calcd. 525.1, found 525.1 |

TABLE 1-continued

Following procedures similar to those described for Examples 1-4, the following compounds were prepared using appropriate starting materials.

| Example | Structure | Name | Exact Mass $[M + H]^+$ |
|---|---|---|---|
| 105 | 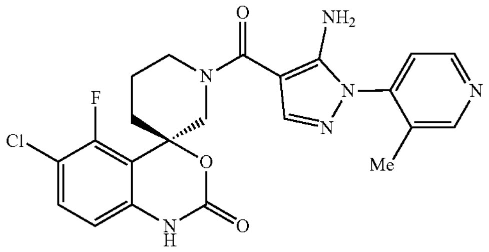 | (R)-1'-(5-Amino-1-(3-methylpyridin-4-yl)-1H-pyrazole-4-carbonyl)-6-chloro-5-fluorospiro[benzo[d][1,3]oxazine-4,3'-piperidin]-2(1H)-one | Calcd. 471.1, found 471.1 |
| 106 | 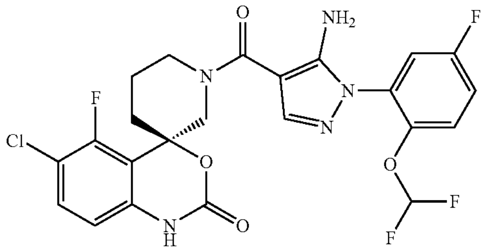 [SMILES: Nc1c(C(=O)N2CCC[C@@]3(C2)OC(=O)Nc2ccc(Cl)c(F)c23)cnn1-c1cc(F)ccc1OC(F)F] | (R)-1'-(5-Amino-1-(2-(difluoromethoxy)-5-fluorophenyl)-1H-pyrazole-4-carbonyl)-6-chloro-5-fluorospiro[benzo[d][1,3]oxazine-4,3'-piperidin]-2(1H)-one | Calcd. 540.1, found 540.3 |
| 107 | 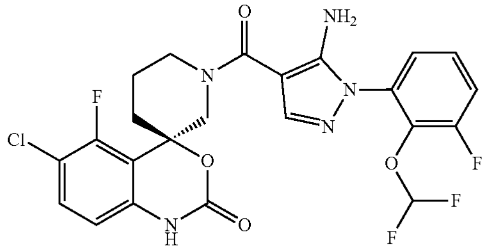 [SMILES: Nc1c(C(=O)N2CCC[C@@]3(C2)OC(=O)Nc2ccc(Cl)c(F)c23)cnn1-c1cccc(F)c1OC(F)F] | (R)-1'-(5-Amino-1-(2-(difluoromethoxy)-3-fluorophenyl)-1H-pyrazole-4-carbonyl)-6-chloro-5-fluorospiro[benzo[d][1,3]oxazine-4,3'-piperidin]-2(1H)-one | Calcd. 540.1, found 540.3 |
| 108 | 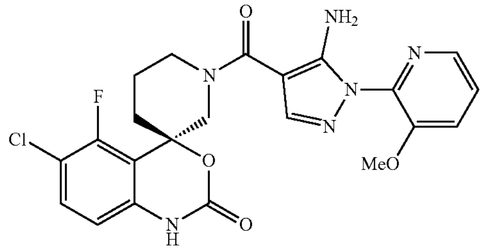 [SMILES: COc1cccnc1-n1ncc(C(=O)N2CCC[C@@]3(C2)OC(=O)Nc2ccc(Cl)c(F)c23)c1N] | (R)-1'-(5-Amino-1-(3-methoxypyridin-2-yl)-1H-pyrazole-4-carbonyl)-6-chloro-5-fluorospiro[benzo[d][1,3]oxazine-4,3'-piperidin]-2(1H)-one | Calcd. 487.1, found 487.0 |
| 109 | 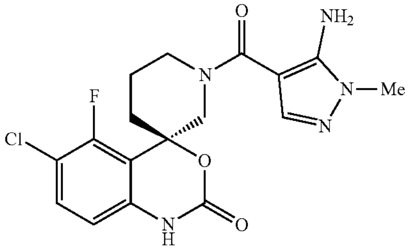 [SMILES: Cn1ncc(C(=O)N2CCC[C@@]3(C2)OC(=O)Nc2ccc(Cl)c(F)c23)c1N] | (R)-1'-(5-Amino-1-methyl-1H-pyrazole-4-carbonyl)-6-chloro-5-fluorospiro[benzo[d][1,3]oxazine-4,3'-piperidin]-2(1H)-one | Calcd. 394.1, found 394.0 |

TABLE 1-continued

Following procedures similar to those described for Examples 1-4, the following compounds were prepared using appropriate starting materials.

| Example | Structure | Name | Exact Mass $[M + H]^+$ |
|---|---|---|---|
| 110 | 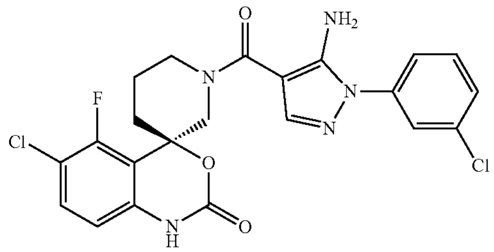 [SMILES: Nc1c(C(=O)N2CCC[C@@]3(C2)OC(=O)Nc2ccc(Cl)c(F)c23)cnn1-c1cccc(Cl)c1] | (R)-1'-(5-Amino-1-(3-chlorophenyl)-1H-pyrazole-4-carbonyl)-6-chloro-5-fluorospiro[benzo[d][1,3]oxazine-4,3'-piperidin]-2(1H)-one | Calcd. 490.1, found 490.3 |
| 111 | 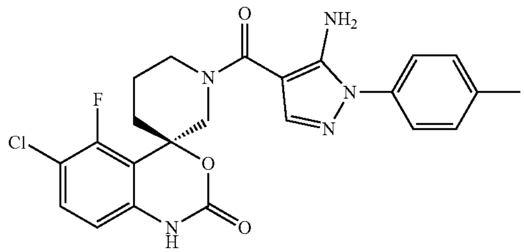 [SMILES: Cc1ccc(-n2ncc(C(=O)N3CCC[C@@]4(C3)OC(=O)Nc3ccc(Cl)c(F)c34)c2N)cc1] | (R)-1'-(5-Amino-1-(p-tolyl)-1H-pyrazole-4-carbonyl)-6-chloro-5-fluorospiro[benzo[d][1,3]oxazine-4,3'-piperidin]-2(1H)-one | Calcd. 470.1, found 469.9 |

TABLE 2

Following procedures similar to those described for Examples 3 and 4, the following compounds were prepared using appropriate starting materials .. Diastereomeric products were separated using chiral SFC methods specified in the table. For those pairs of diastereomers, the fast-eluting isomer is listed first.

| Example | Structure | Name | Exact Mass $[M + H]^+$ | Chiral Method |
|---|---|---|---|---|
| 112 | 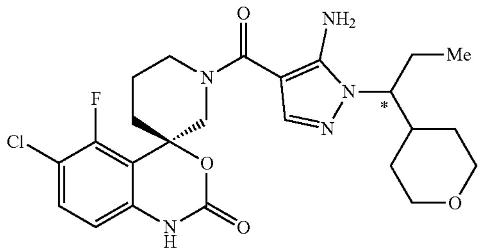 [SMILES: CCC(C1CCOCC1)n1ncc(C(=O)N2CCC[C@@]3(C2)OC(=O)Nc2ccc(Cl)c(F)c23)c1N] | (R)-1'-(5-Amino-1-((R or S)-1-(tetrahydro-2H-pyran-4-yl)propyl)-1H-pyrazole-4-carbonyl)-6-chloro-5-fluorospiro[benzo[d][1,3]oxazine-4,3'-piperidin]-2(1H)-one | found 506.2 | J |
| 113 | 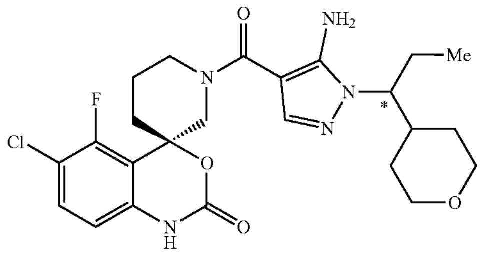 [SMILES: CCC(C1CCOCC1)n1ncc(C(=O)N2CCC[C@@]3(C2)OC(=O)Nc2ccc(Cl)c(F)c23)c1N] | (R)-1'-(5-Amino-1-((S or R)-1-(tetrahydro-2H-pyran-4-yl)propyl)-1H-pyrazole-4-carbonyl)-6-chloro-5-fluorospiro[benzo[d][1,3]oxazine-4,3'-piperidin]-2(1H)-one | Calcd. 506.2, found 506.2 | J |

TABLE 2-continued

Following procedures similar to those described for Examples 3 and 4, the following compounds were prepared using appropriate starting materials .. Diastereomeric products were separated using chiral SFC methods specified in the table. For those pairs of diastereomers, the fast-eluting isomer is listed first.

| Example | Structure | Name | Exact Mass $[M + H]^+$ | Chiral Method |
|---|---|---|---|---|
| 114 | 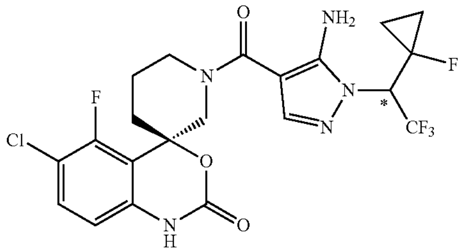 [SMILES: Nc1c(C(=O)N2CCC[C@@]3(C2)OC(=O)Nc2ccc(Cl)c(F)c23)cnn1C(C(F)(F)F)C1(F)CC1] | (R)-1'-(5-Amino-1-((R or S)-2,2,2-trifluoro-1-(1-fluorocyclopropyl)ethyl)-1H-pyrazole-4-carbonyl)-6-chloro-5-fluorospiro[benzo[d][1,3]oxazine-4,3'-piperidin]-2(1H)-one | Calcd. 520.1, found 520.0 | G |
| 115 | 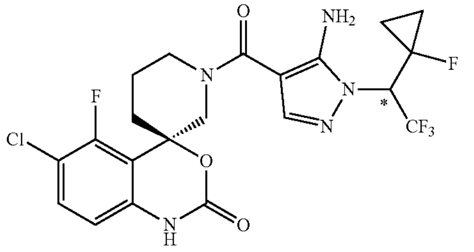 [SMILES: Nc1c(C(=O)N2CCC[C@@]3(C2)OC(=O)Nc2ccc(Cl)c(F)c23)cnn1C(C(F)(F)F)C1(F)CC1] | (R)-1'-(5-Amino-1-((S or R)-2,2,2-trifluoro-1-(1-fluorocyclopropyl)ethyl)-1H-pyrazole-4-carbonyl)-6-chloro-5-fluorospiro[benzo[d][1,3]oxazine-4,3'-piperidin]-2(1H)-one | Calcd. 520.1, found 520.0 | G |
| 116 | 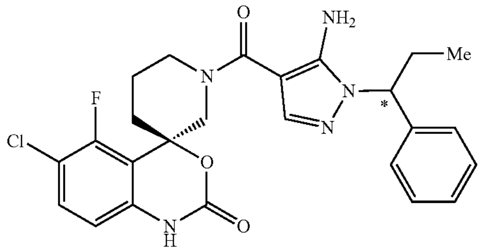 [SMILES: CCC(c1ccccc1)n1ncc(C(=O)N2CCC[C@@]3(C2)OC(=O)Nc2ccc(Cl)c(F)c23)c1N] | (R)-1'-(5-Amino-1-((S or R)-1-phenylpropyl)-1H-pyrazole-4-carbonyl)-6-chloro-5-fluorospiro[benzo[d][1,3]oxazine-4,3'-piperidin]-2(1H)-one | Calcd. 498.2, found 498.2 | J |
| 117 | 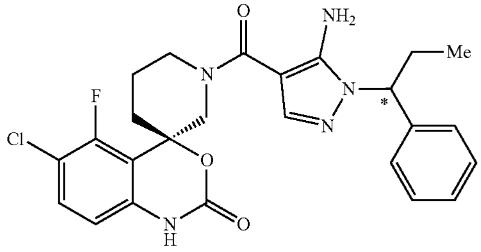 [SMILES: CCC(c1ccccc1)n1ncc(C(=O)N2CCC[C@@]3(C2)OC(=O)Nc2ccc(Cl)c(F)c23)c1N] | (R)-1'-(5-Amino-1-((R or S)-1-phenylpropyl)-1H-pyrazole-4-carbonyl)-6-chloro-5-fluorospiro[benzo[d][1,3]oxazine-4,3'-piperidin]-2(1H)-one | Calcd. 498.2, found 498.2 | J |
| 118 | 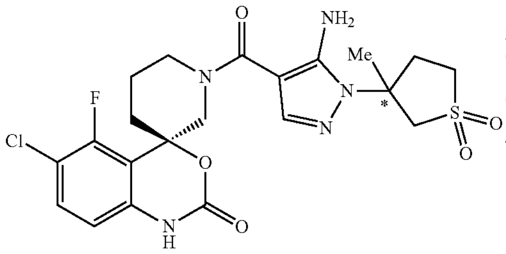 [SMILES: CC1(n2ncc(C(=O)N3CCC[C@@]4(C3)OC(=O)Nc3ccc(Cl)c(F)c34)c2N)CCS(=O)(=O)C1] | (R)-1'-(5-Amino-1-((R or S)-3-methyl-1,1-dioxidotetrahydrothiophen-3-yl)-1H-pyrazole-4-carbonyl)-6-chloro-5-fluorospiro[benzo[d][1,3]oxazine-4,3'-piperidin]-2(1H)-one | Calcd. 512.1, found 512.3 | C |

TABLE 2-continued

Following procedures similar to those described for Examples 3 and 4, the following compounds were prepared using appropriate starting materials .. Diastereomeric products were separated using chiral SFC methods specified in the table. For those pairs of diastereomers, the fast-eluting isomer is listed first.

| Example | Structure | Name | Exact Mass [M + H]+ | Chiral Method |
|---|---|---|---|---|
| 119 | 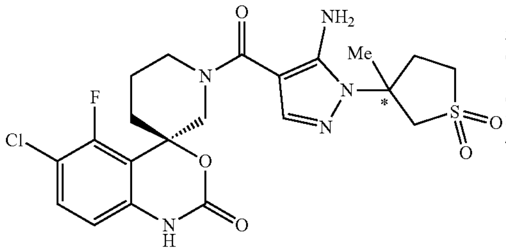 [SMILES: CC1(n2ncc(C(=O)N3CCC[C@@]4(C3)OC(=O)Nc3ccc(Cl)c(F)c34)c2N)CCS(=O)(=O)C1] | (R)-1'-(5-Amino-1-((Sor R)-3-methyl-1,1-dioxidotetrahydrothiophen-3-yl)-1H-pyrazole-4-carbonyl)-6-chloro-5-fluorospiro[benzo[d][1,3]oxazine-4,3'-piperidin]-2(1H)-one | Calcd. 512.1, found 512.3 | C |
| 120 | 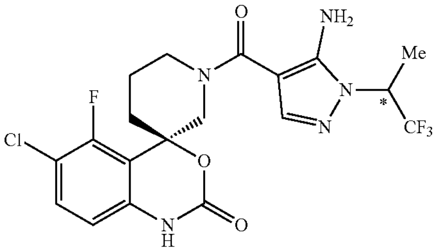 | (R)-1'-(5-Amino-1-((R or S)-1,1,1-trifluoropropan-2-yl)-1H-pyrazole-4-carbonyl)-6-chloro-5-fluorospiro[benzo[d][1,3]oxazine-4,3'-piperidin]-2(1H)-one | Calcd. 476.1, found 476.4 | D |
| 121 | 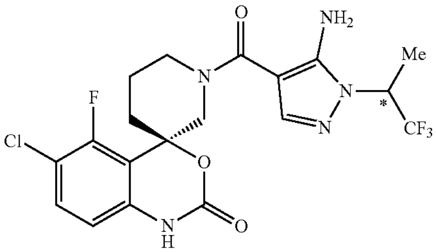 [SMILES: CC(n1ncc(C(=O)N2CCC[C@@]3(C2)OC(=O)Nc2ccc(Cl)c(F)c23)c1N)C(F)(F)F] | (R)-1'-(5-Amino-1-((S or R)-1,1,1-trifluoropropan-2-yl)-1H-pyrazole-4-carbonyl)-6-chloro-5-fluorospiro[benzo[d][1,3]oxazine-4,3'-piperidin]-2(1H)-one | Calcd. 476.1, found 476.4 | D |
| 122 | 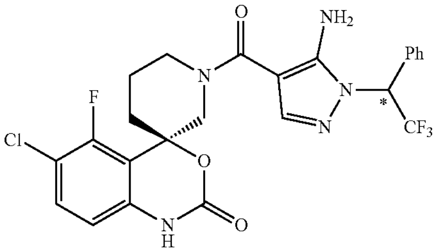 [SMILES: Nc1c(C(=O)N2CCC[C@@]3(C2)OC(=O)Nc2ccc(Cl)c(F)c23)cnn1C(c1ccccc1)C(F)(F)F] | (R)-1'-(5-Amino-1-((R or S)-2,2,2-trifluoro-1-phenylethyl)-1H-pyrazole-4-carbonyl)-6-chloro-5-fluorospiro[benzo[d][1,3]oxazine-4,3'-piperidin]-2(1H)-one | Calcd. 538.1, found 538.0 | H |
| 123 | 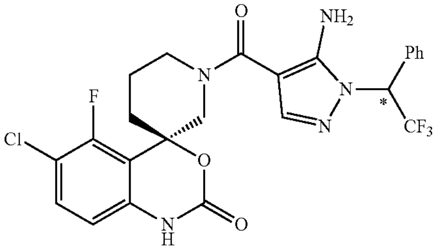 [SMILES: Nc1c(C(=O)N2CCC[C@@]3(C2)OC(=O)Nc2ccc(Cl)c(F)c23)cnn1C(c1ccccc1)C(F)(F)F] | (R)-1'-(5-Amino-1-((Sor R)-2,2,2-trifluoro-1-phenylethyl)-1H-pyrazole-4-carbonyl)-6-chloro-5-fluorospiro[benzo[d][1,3]oxazine-4,3'-piperidin]-2(1H)-one | Calcd. 538.1, found 538.0 | H |

TABLE 2-continued

Following procedures similar to those described for Examples 3 and 4, the following compounds were prepared using appropriate starting materials .. Diastereomeric products were separated using chiral SFC methods specified in the table. For those pairs of diastereomers, the fast-eluting isomer is listed first.

| Example | Structure | Name | Exact Mass $[M + H]^+$ | Chiral Method |
|---|---|---|---|---|
| 124 | 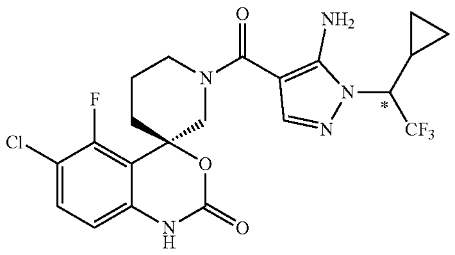 [SMILES: Nc1c(C(=O)N2CCC[C@@]3(C2)OC(=O)Nc2ccc(Cl)c(F)c23)cnn1C(C1CC1)C(F)(F)F] | (R)-1'-(5-Amino-1-((R or S)-1-cyclopropyl-2,2,2-trifluoroethyl)-1H-pyrazole-4-carbonyl)-6-chloro-5-fluorospiro[benzo[d][1,3]oxazine-4,3'-piperidin]-2(1H)-one | Calcd. 502.1, found 502.1 | E |
| 125 | 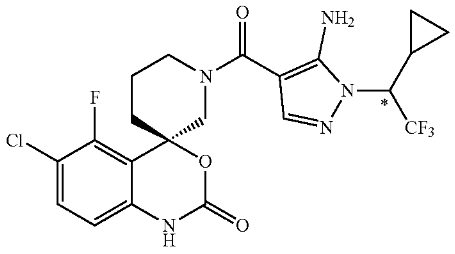 [SMILES: Nc1c(C(=O)N2CCC[C@@]3(C2)OC(=O)Nc2ccc(Cl)c(F)c23)cnn1C(C1CC1)C(F)(F)F] | (R)-1'-(5-Amino-1-((S or R)-1-cyclopropyl-2,2,2-trifluoroethyl)-1H-pyrazole-4-carbonyl)-6-chloro-5-fluorospiro[benzo[d][1,3]oxazine-4,3'-piperidin]-2(1H)-one | Calcd. 502.1, found 502.1 | E |
| 126 | 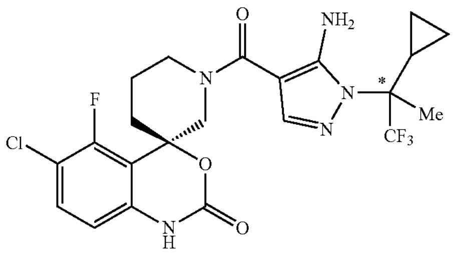 [SMILES: CC(C1CC1)(n1ncc(C(=O)N2CCC[C@@]3(C2)OC(=O)Nc2ccc(Cl)c(F)c23)c1N)C(F)(F)F] | (R)-1'-(5-Amino-1-((R or S)-2-cyclopropyl-1,1,1-trifluoropropan-2-yl)-1H-pyrazole-4-carbonyl)-6-chloro-5-fluorospiro[benzo[d][1,3]oxazine-4,3'-piperidin]-2(1H)-one | Calcd. 516.1, found 516.2 | F |
| 127 | 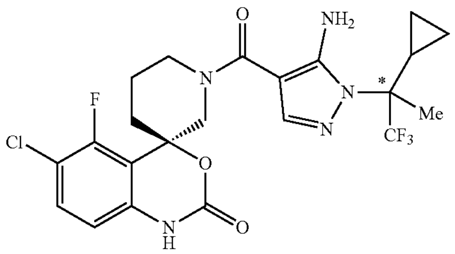 [SMILES: CC(C1CC1)(n1ncc(C(=O)N2CCC[C@@]3(C2)OC(=O)Nc2ccc(Cl)c(F)c23)c1N)C(F)(F)F] | (R)-1'-(5-Amino-1-((S or R)-2-cyclopropyl-1,1,1-trifluoropropan-2-yl)-1H-pyrazole-4-carbonyl)-6-chloro-5-fluorospiro[benzo[d][1,3]oxazine-4,3'-piperidin]-2(1H)-one | Calcd. 516.1, found 516.2 | F |
| 128 | 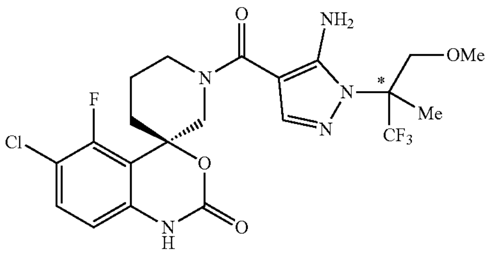 [SMILES: COCC(C)(n1ncc(C(=O)N2CCC[C@@]3(C2)OC(=O)Nc2ccc(Cl)c(F)c23)c1N)C(F)(F)F] | (R)-1'-(5-Amino-1-((R or S)-1,1,1-trifluoro-3-methoxy-2-methylpropan-2-yl)-1H-pyrazole-4-carbonyl)-6-chloro-5-fluorospiro[benzo[d][1,3]oxazine-4,3'-piperidin]-2(1H)-one | Calcd. 520.1, found 520.3 | B |

TABLE 2-continued

Following procedures similar to those described for Examples 3 and 4, the following compounds were prepared using appropriate starting materials .. Diastereomeric products were separated using chiral SFC methods specified in the table. For those pairs of diastereomers, the fast-eluting isomer is listed first.

| Example | Structure | Name | Exact Mass $[M + H]^+$ | Chiral Method |
| --- | --- | --- | --- | --- |
| 129 | 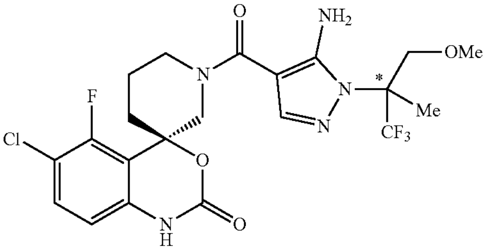 [SMILES: COCC(C)(n1ncc(C(=O)N2CCC[C@@]3(C2)OC(=O)Nc2ccc(Cl)c(F)c23)c1N)C(F)(F)F] | (R)-1'-(5-Amino-1-((Sor R)-1,1,1-trifluoro-3-methoxy-2-methylpropan-2-yl)-1H-pyrazole-4-carbonyl)-6-chloro-5-fluorospiro[benzo[d][1,3]oxazine-4,3'-piperidin]-2(1H)-one | Calcd. 520.1, found 520.3 | B |
| 130 | 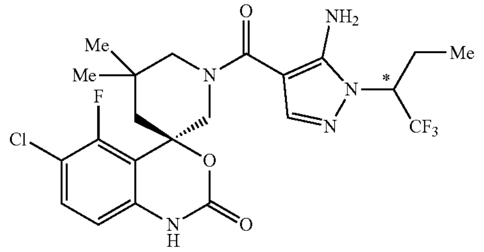 [SMILES: CCC(n1ncc(C(=O)N2CC(C)(C)C[C@@]3(C2)OC(=O)Nc2ccc(Cl)c(F)c23)c1N)C(F)(F)F] | (R)-1'-(5-Amino-1-((R or S)-1,1,1-trifluorobutan-2-yl)-1H-pyrazole-4-carbonyl)-6-chloro-5-fluoro-5',5'-dimethylspiro[benzo[d][1,3] oxazine-4,3'-piperidin]-2(1H)-one | Calcd. 518.2, found 518.4 | D |
| 131 | 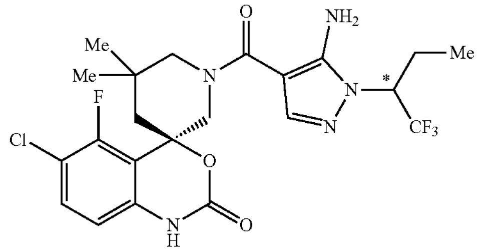 [SMILES: CCC(n1ncc(C(=O)N2CC(C)(C)C[C@@]3(C2)OC(=O)Nc2ccc(Cl)c(F)c23)c1N)C(F)(F)F] | (R)-1'-(5-Amino-1-((S or R)-1,1,1-trifluorobutan-2-yl)-1H-pyrazole-4-carbonyl)-6-chloro-5-fluoro-5',5'-dimethylspiro[benzo[d][1,3] oxazine-4,3'-piperidin]-2(1H)-one | Calcd. 518.2, found 518.4 | D |

Example 132

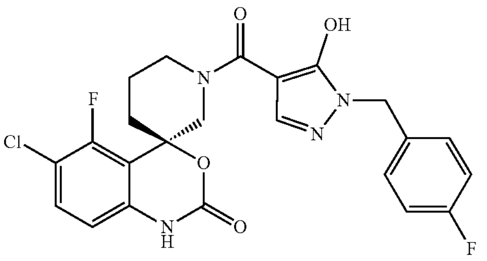 [SMILES: O=C1Nc2ccc(Cl)c(F)c2[C@@]2(CCCN(C(=O)c3cnn(Cc4ccc(F)cc4)c3O)C2)O1]

(R)-6-Chloro-5-fluoro-1'-(1-(4-fluorobenzyl)-5-hydroxy-1H-pyrazole-4-carbonyl)spiro[benzo[d][1,3] oxazine-4,3'-piperidin]-2(1H)-one Step 1: Ethyl 1-(4-fluorobenzyl)-5-hydroxy-1H-pyrazole-4-carboxylate: To a solution of (4-fluorobenzyl)hydrazine hydrochloride (650 mg, 3.68 mmol) and diethyl 2-(ethoxymethylene)malonate (875 mg, 4.05 mmol) in $H_2O$ (3 mL) was added $K_2CO_3$ (1.27 g, 9.20 mmol), and the resulting mixture was heated to 100° C. for 3 h. The reaction was cooled to rt, and the mixture was washed with EtOAc. The aq. phase was acidified with 1 M HCl to pH 2 and extracted with EtOAc. The organic layers were dried over $Na_2SO_4$, filtered, and concentrated under reduced pressure to give the crude title compound that was carried forward without further purification. LCMS $[M+H]^+$=265.0 (calcd. 265.1).

Step 2: 1-(4-Fluorobenzyl)-5-hydroxy-1H-pyrazole-4-carboxylic acid: To a solution of ethyl 1-(4-fluorobenzyl)-5-hydroxy-1H-pyrazole-4-carboxylate (25 mg, 0.095 mmol) in EtOH (1 mL) and $H_2O$ (0.2 mL) was added NaOH (38 mg, 0.95 mmol), and the resulting mixture was heated to 90° C. for 4 h. The reaction was cooled to rt and concentrated to afford a crude residue that was acidified with 1 M HCl to pH 2 and extracted with EtOAc. The organic layers were dried over $Na_2SO_4$, filtered, and concentrated under reduced pressure to give the crude title compound that was carried forward without further purification. LCMS $[M+H]^+$=237.0 (calcd. 237.1).

Step 3: (R)-6-Chloro-5-fluoro-1'-(1-(4-fluorobenzyl)-5-hydroxy-1H-pyrazole-4-carbonyl)spiro[benzo[d][1,3]oxazine-4,3'-piperidin]-2(1H)-one: To a solution of 1-(4-fluorobenzyl)-5-hydroxy-1H-pyrazole-4-carboxylic acid (20 mg, 0.085 mmol) and (R)-6-chloro-5-fluorospiro[benzo[d][1,3] oxazine-4,3'-piperidin]-2(1H)-one (31 mg, 0.085 mmol) in ACN (2 mL) was added TCFH (26 mg, 0.093 mmol) and 1-methylimidazole (21 mg, 0.25 mmol), and the resulting mixture was stirred at rt for 12 h. The reaction was concentrated to afford a crude residue that was purified by preparative reverse phase HPLC (C18 stationary phase, ACN/water+0.1% TFA) to afford mixture of diastereomers of the title compound. $^1$H NMR (500 MHz, $CD_3OD$) δ 7.91 (br s, 1H), 7.46 (t, J=8.2 Hz, 1H), 7.32 (br s, 2H), 7.09 (br t, J=8.5 Hz, 2H), 6.76 (br d, J=8.4 Hz, 1H), 5.13 (br s, 2H), 4.36 (s, 2H), 3.19 (br s, 2H), 2.52 (br s, 1H), 2.31 (br d, J=13.7 Hz, 1H), 2.17 (br d, J=13.1 Hz, 1H), 1.75 (br d, J=14.5 Hz, 1H). LCMS $[M+H]^+$=489.1 (calcd. 489.1).

Example 133

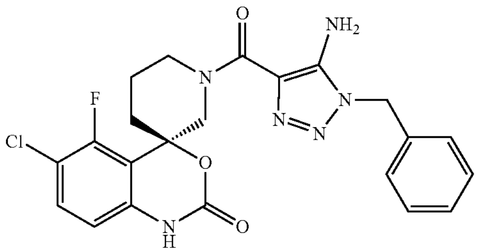 [SMILES: Nc1c(C(=O)N2CCC[C@@]3(C2)OC(=O)Nc2ccc(Cl)c(F)c23)nnn1Cc1ccccc1]

(R)-1'-(5-Amino-1-benzyl-1H-1,2,3-triazole-4-carbonyl)-6-chloro-5-fluorospiro[benzo[d][1,3]oxazine-4,3'-piperidin]-2(1H)-one A 4 mL vial was charged with (R)-6-chloro-5-fluoro-2-oxo-1,2-dihydrospiro[benzo[d][1,3]oxazine-4,3'-piperidin]-1'-ium 2,2,2-trifluoroacetate (50 mg, 0.13 mmol) and 5-amino-1-benzyl-1H-1,2,3-triazole-4-carboxylic acid (28 mg, 0.13 mmol) in DMF (5 mL). To this mixture, DIEA (23 μL, 0.13 mmol) was added followed by the addition of HATU (49 mg, 0.13 mmol) in one portion, and the resulting mixture was allowed to stir at rt for 2 h. The reaction mixture was purified directly via preparative reverse phase HPLC (C18 stationary phase, ACN/water+0.05% TFA) to afford the title compound. $^1$H NMR (500 MHz, $CD_3OD$) δ 7.91 (br s, 1H), 7.46 (t, J=8.2 Hz, 1H), 7.32 (br s, 2H), 7.09 (br t, J=8.5 Hz, 2H), 6.76 (br d, J=8.4 Hz, 1H), 5.13 (br s, 2H), 4.36 (s, 2H), 3.19 (br s, 2H), 2.52 (br s, 1H), 2.31 (br d, J=13.7 Hz, 1H), 2.17 (br d, J=13.1 Hz, 1H), 1.75 (br d, J=14.5 Hz, 1H). LCMS $[M+H]^+$=489.1 (calcd. 489.1).

Factor XIa Assay

The effectiveness of a compound of the present invention as an inhibitor of Coagulation factor XIa can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at rt or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the half-maximal inhibitory concentrations ($IC_{50}$), or the inhibitory constant, $K_i$.

Compounds were pre-incubated for 30 min at 25° C. with human (0.04 nM) factor XIa in 50 mM HEPES buffer with 150 mM sodium chloride, 5 mM calcium chloride, 0.1% PEG 8000, pH 7.4. factor XIa enzymatic activity was determined by addition of the substrate glycine-proline-arginine-7-amido-4-trifluoromethylcoumarin (GPR-AFC) and measurement of the fluorescence at 400/505 nm after a 60 min incubation at 25° C. The % inhibition for each data point was calculated from the data and analyzed using the log (inhibitor) vs. response four parameters equation to determine the half-maximal inhibitory concentrations ($IC_{50}$). The $IC_{50}$ were converted to equilibrium inhibitory constants (Ki) using the Cheng-Prusoff equation.

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

Plasma Kallikrein Assay

The effectiveness of a compound of the present invention as an inhibitor of plasma kallikrein can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at rt or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the half-maximal inhibitory concentrations ($IC_{50}$), or the inhibitory constant, $K_i$.

Plasma kallikrein determinations were made in 50 mM HEPES buffer at pH 7.4 containing 150 mM NaCl, 5 mM $CaCl_2$), and 0.1% PEG 8000 (polyethylene glycol; Fisher Scientific). Determinations were made using purified Human plasma kallikrein at a final concentration of 0.5 nM (Enzyme Research Laboratories) and the synthetic substrate, Acetyl-K—P—R-AFC (Sigma #C6608) at a concentration of 100 mM.

Activity assays were performed by diluting a stock solution of substrate at least tenfold to a final concentration≤0.2 Km into a solution containing enzyme or enzyme equilibrated with inhibitor. Times required to achieve equilibration between enzyme and inhibitor were determined in control experiments. The reactions were performed under linear progress curve conditions and fluorescence increase measured at 405 Ex/510 Em nm. Values were converted to percent inhibition of the control reaction (after subtracting 100% Inhibition value). $IC_{50}$ was determined by inflection point from a four parameter logistic curve fit. Ki was calculated using the Cheng Prusoff equation, $Ki=IC_{50}/IC_{50}/(1+([S]/Km))$.

The activities shown by this assay indicate that the compounds of the invention may be therapeutically useful for treating or preventing various ophthalmic, cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, reocclusion or restenosis of recanalized vessels, hereditary angioedema, uveitis, posterior uveitis, wet age related macular edema, diabetic macular edema, diabetic retinopathy and retinal vein occlusion.

Plasma Kallikrein $IC_{50}$ (nM) and FXIa $IC_{50}$ (nM) for Selected Compounds are as Follows:

| Example | PKal $IC_{50}$ (nM) | FXIa $IC_{50}$ (nM) |
|---|---|---|
| 1 | 11.2 | 408 |
| 2 | 2.7 | 211 |
| 3 | 1.0 | 105 |
| 4 | 0.8 | 9 |
| 5 | 1.7 | 726 |
| 6 | 0.5 | 177 |
| 7 | 0.5 | 201 |
| 8 | 0.6 | 68 |
| 9 | 0.9 | 252 |
| 10 | 1.3 | 122 |
| 11 | 1.7 | 438 |
| 12 | 8.1 | 476 |
| 13 | 7.2 | 582 |
| 14 | 42.8 | 3177 |
| 15 | 16.9 | 882 |
| 16 | 4.1 | 441 |
| 17 | 8.0 | 328 |
| 18 | 39.1 | 1651 |
| 19 | 28.9 | 2944 |
| 20 | 5.9 | 882 |
| 21 | 12.6 | 1096 |
| 22 | 15.3 | 1122 |
| 23 | 13.5 | 2249 |
| 24 | 10.9 | 425 |
| 25 | 24.8 | 2002 |
| 26 | 8.3 | 352 |
| 27 | 18.8 | 699 |
| 28 | 2.9 | 112 |
| 29 | 7.9 | 705 |
| 30 | 18.4 | 2830 |
| 31 | 2.5 | 358 |
| 32 | 1.7 | 268 |
| 33 | 1.0 | 438 |
| 34 | 8.9 | 1201 |
| 35 | 15.7 | 1076 |
| 36 | 2.0 | 140 |
| 37 | 10.5 | 4599 |
| 38 | 2.4 | 449 |
| 39 | 1.2 | 293 |
| 40 | 2.3 | 249 |
| 41 | 11.4 | 746 |
| 42 | 1.4 | 504 |
| 43 | 8.0 | 905 |
| 44 | 1.1 | 251 |
| 45 | 0.7 | 156 |
| 46 | 1.2 | 167 |
| 47 | 6.3 | 731 |
| 48 | 13.1 | 516 |
| 49 | 16.9 | 2931 |
| 50 | 8.3 | 684 |
| 51 | 9.8 | 996 |
| 52 | 9.1 | 978 |
| 53 | 8.7 | 1110 |
| 54 | 3.4 | 601 |
| 55 | 2.0 | 418 |
| 56 | 2.9 | 932 |
| 57 | 40.0 | 4142 |
| 58 | 39.7 | 3130 |
| 59 | 25.7 | 1158 |
| 60 | 8.0 | 599 |

-continued

| Example | PKal $IC_{50}$ (nM) | FXIa $IC_{50}$ (nM) |
|---|---|---|
| 61 | 42.5 | 1745 |
| 62 | 22.9 | 855 |
| 63 | 29.0 | 1579 |
| 64 | 28.1 | 1314 |
| 65 | 37.5 | 160 |
| 66 | 39.0 | 242 |
| 67 | 46.2 | 7317 |
| 68 | 13.5 | 1482 |
| 69 | 41.7 | 4591 |
| 70 | 13.4 | 1143 |
| 71 | 36.6 | 4054 |
| 72 | 6.4 | 262 |
| 73 | 22.5 | 316 |
| 74 | 8.4 | 378 |
| 75 | 50.7 | 4720 |
| 76 | 29.5 | 1063 |
| 77 | 17.3 | 399 |
| 78 | 35.9 | 813 |
| 79 | 5.8 | 377 |
| 80 | 11.6 | 325 |
| 81 | 5.5 | 353 |
| 82 | 28.4 | 739 |
| 83 | 35.5 | 862 |
| 84 | 27.3 | 923 |
| 85 | 9.2 | 1955 |
| 86 | 46.0 | 645 |
| 87 | 26.4 | 1173 |
| 88 | 47.0 | 1691 |
| 89 | 1.6 | 162 |
| 90 | 6.6 | 215 |
| 91 | 5.8 | 525 |
| 92 | 13.2 | 1709 |
| 93 | 10.4 | 418 |
| 94 | 11.8 | 1289 |
| 95 | 10.0 | 305 |
| 96 | 1.1 | 1373 |
| 97 | 8.0 | 1286 |
| 98 | 8.4 | 219 |
| 99 | 13.3 | 1079 |
| 100 | 9.0 | 375 |
| 101 | 30.6 | 1307 |
| 102 | 3.8 | 12 |
| 103 | 10.1 | 610 |
| 104 | 9.5 | 562 |
| 105 | 13.2 | 421 |
| 106 | 34.8 | 1071 |
| 107 | 15.2 | 461 |
| 108 | 39.6 | 1692 |
| 109 | 338.3 | >10000 |
| 110 | 66.1 | >10000 |
| 111 | 80.3 | 2990 |
| 112 | 2.2 | 62 |
| 113 | 0.6 | 2 |
| 114 | 2.8 | 103 |
| 115 | 0.6 | 42 |
| 116 | 0.7 | 4 |
| 117 | 0.9 | 30 |
| 118 | 24.0 | 1002 |
| 119 | 21.0 | 1461 |
| 120 | 4.3 | 221 |
| 121 | 4.9 | 591 |
| 122 | 1.0 | 95 |
| 123 | 0.9 | 74 |
| 124 | 1.4 | 75 |
| 125 | 4.5 | 154 |
| 126 | 2.2 | 459 |
| 127 | 6.8 | 1022 |
| 128 | 4.7 | 973 |
| 129 | 6.5 | 898 |
| 130 | 1.6 | 8 |
| 131 | 1.2 | 70 |
| 132 | 17.8 | 10000 |
| 133 | 190.2 | 328 |

What is claimed is:

1. A compound of the formula:

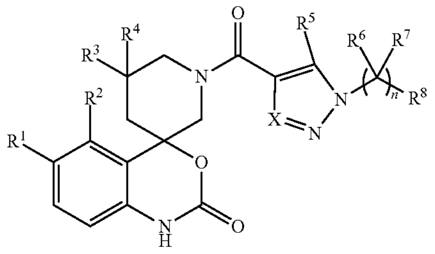

wherein X is N or CH;

$R^1$ is selected from the group consisting of hydrogen, halo, hydroxy and $C_{1-6}$ alkyl;

$R^2$ is selected from the group consisting of hydrogen, halo, hydroxy and $C_{1-6}$ alkyl;

$R^3$ is selected from the group consisting of hydrogen, halo, hydroxy and $C_{1-6}$ alkyl, wherein said alkyl group is optionally substituted with one to four substituents independently selected from the group consisting of halo, cyano and $OR^x$;

$R^4$ is selected from the group consisting of hydrogen, halo, hydroxy and $C_{1-6}$ alkyl;

wherein said alkyl group is optionally substituted with one to four substituents independently selected from the group consisting of halo, cyano and $OR^x$;

$R^5$ is $NR^9R^{10}$ or $OR^x$;

each $R^6$ is independently selected from the group consisting of hydrogen, halo, hydroxy and $C_{1-6}$ alkyl, wherein said alkyl group is optionally substituted with one to three halo;

each $R^7$ is selected from the group consisting of hydrogen, halo, hydroxy and $C_{1-6}$ alkyl, wherein said alkyl group is optionally substituted with one to three halo;

or $R^6$ and $R^7$ can be taken together with the carbon atom to which they are attached to form a 3-6 membered cycloalkyl group, which is optionally substituted with one or two halo;

$R^8$ is selected from the group consisting of hydrogen; halo; hydroxy; $R^x$; $OR^x$; phenyl; indane; $OR^y$; heteroaryl, which can be monocyclic or bicyclic; heterocyclyl; and $C_{3-6}$ cycloalkyl, which can be monocyclic or bicyclic; wherein said phenyl and heteroaryl groups are optionally substituted with one to three substituents independently selected from the group consisting of oxo, halo, $R^x$, $OR^x$, $NR^9R^{10}$, $NR^9(C{=}O)R^x$, $NR^9(C{=}O)OR^x$, $(C{=}O)OR^x$, $(C{=}O)NR^9$, $R^y$ and $OR^y$;

wherein said cycloalkyl and heterocyclyl groups are optionally substituted with one to three substituents independently selected from the group consisting of oxo, halo, $R^x$ and $OR^x$;

$R^9$ is hydrogen or $C_{1-3}$ alkyl;

$R^{10}$ is hydrogen or $C_{1-3}$ alkyl;

$R^x$ is hydrogen or $C_{1-6}$ alkyl, which is optionally substituted with one to three substituents selected from the group consisting of halo and hydroxy, $R^y$ is phenyl, heterocyclyl or $C_{3-6}$ cycloalkyl, wherein said phenyl group is optionally substituted with one to three halo, said heterocyclyl group is optionally substituted with one or two oxo and said cycloalkyl group is optionally substituted with $C_{1-6}$ alkyl;

and n is an integer from zero to two;

or a pharmaceutically salt thereof.

2. The compound of claim 1 wherein $R^1$ is halo and $R^2$ is halo; or a pharmaceutically acceptable salt thereof.

3. The compound of claim 1 wherein $R^3$ is hydrogen or methyl and $R^4$ is hydrogen or methyl; or a pharmaceutically acceptable salt thereof.

4. The compound of claim 1 wherein $R^5$ is $NH_2$; or a pharmaceutically acceptable salt thereof.

5. The compound of claim 1 wherein n is zero or one; or a pharmaceutically acceptable salt thereof.

6. The compound of claim 1 wherein $R^8$ is phenyl; wherein said phenyl is optionally substituted with one to three substituents independently selected from the group consisting of halo, $R^x$, $OR^x$, $NR^9R^{10}$, $NR^9(C{=}O)R^x$, $NR^9(C{=}O)OR^x$, $(C{=}O)NR^9$, $(C{=}O)OR^y$, $R^y$ and $OR^y$; or a pharmaceutically acceptable salt thereof.

7. The compound of claim 1 wherein $R^8$ is phenyl; wherein said phenyl is optionally substituted with one to three substituents independently selected from the group consisting of halo, $R^x$, $OR^x$, $R^y$ and $OR^y$; or a pharmaceutically acceptable salt thereof.

8. The compound of claim 1 wherein n is one; $R^6$ is hydrogen and $R^7$ is hydrogen; or a pharmaceutically acceptable salt thereof.

9. The compound of claim 1 selected from any one of compounds (R)-1'-(5-Amino-1-(2,2,2-trifluoroethyl-1H-pyrazole-4-carbonyl)-6-chloro-5-fluorospiro[benzo[d][1,3]oxazine-4,3'-piperidin]-2(1H)-one, (R)-1'-(5-Amino-1-(2,2,2-trifluoroethyl)-1H-pyrazole-4-carbonyl)-6-chloro-5-fluoro-5',5'-dimethylspiro[benzo[d][1,3]oxazine-4,3'-piperidin]-2(1H)-one, (R)-1'-(5-amino-1-((R)-1,1,1-trifluorobutan-2-yl)-1H-pyrazole-4-carbonyl)-6-chloro-5-fluorospiro[benzo[d][1,3]oxazine-4,3'-piperidin]-2(1H)-one, (R)-1'-(5-amino-1-((S)-1,1,1-trifluorobutan-2-yl)-1H-pyrazole-4-carbonyl)-6-chloro-5-fluorospiro[benzo[d][1,3]oxazine-4,3'-piperidin]-2(1H)-one, (R)-1'-(5-Amino-1-(3-(trifluoromethyl)benzyl)-1H-pyrazole-4-carbonyl)-6-chloro-5-fluorospiro[benzo[d][1,3]oxazine-4,3'-piperidin]-2(1H)-one, (R)-1'-(5-Amino-1-(3-chlorobenzyl)-1H-pyrazole-4-carbonyl)-6-chloro-5-fluorospiro[benzo[d][1,3]oxazine-4,3'-piperidin]-2(1H)-one, (R)-1'-5-Amino-1-(4-methylbenzyl)-1H-pyrazole-4-carbonyl)-6-chloro-5-fluorospiro[benzo[d][1,3]oxazine-4,3'-piperidin]-2(1H)-one, (R)-1'-(5-Amino-1-benzyl-1H-pyrazole-4-carbonyl)-6-chloro-5-fluorospiro[benzo[d][1,3]oxazine-4,3'-piperidin]-2(1H)-one, (R)-1'-5-Amino-1-(3-fluorobenzyl)-1H-pyrazole-4-carbonyl)-6-chloro-5-fluorospiro[benzo[d][1,3]oxazine-4,3'-piperidin]-2(1H)-one, (R)-1'-(5-Amino-1-benzyl-1H-pyrazole-4-carbonyl)-6-chloro-5-fluoro-5',5'-dimethylspiro[benzo[d][1,3]oxazine-4,3'-piperidin]-2(1H)-one, (R)-1'-(5-Amino-1-((3,5-dimethylisoxazol-4-yl)methyl)-1H-pyrazole-4-carbonyl)-6-chloro-5-fluorospiro[benzo[d][1,3]oxazine-4,3'-piperidin]-2(1H)-one, (R)-1'-(5-Amino-1-((tetrahydro-2H-pyran-4-yl)methyl)-1H-pyrazole-4-carbonyl)-6-chloro-5-fluorospiro[benzo[d][1,3]oxazine-4,3'-piperidin]-2(1H)-one, (R)-1'-(5-Amino-1-(cyclopropylmethyl)-1H-pyrazole-4-carbonyl)-6-chloro-5-fluorospiro[benzo[d][1,3]oxazine-4,3'-piperidin]-2(1H)-one, (R)-1'-(5-Amino-1-(2-morpholinoethyl)-1H-pyrazole-4-carbonyl)-6-chloro-5-fluorospiro[benzo[d][1,3]oxazine-4,3'-piperidin]-2(1H)-one, (R)-1'-(5-Amino-1-(2,2-difluorethyl)-1H-Pyrazole-4-carbonyl)-6-chloro-5-fluorospiro[benzo[d][1,3]oxazine-4,3'-piperidin]-2(1H)-one, (R)-1'-(5-Amino-1-phenethyl-1H-pyrazole-4-carbonyl)-6-chloro-5-fluorospiro[benzo[d][1,3]oxazine-4,3'-piperidin-2(1H)-one, (R)-1'-(5-Amino-1-isobutyl-1H-pyrazole-4-carbonyl-6-chloro-5-fluorospiro[benzo[d][1,3]oxazine-4,3'-piperidin]-2(1H)-one, (R)-1'-(5-Amino-1-(tetrahydro-2H-pyran-4-yl)-1H-pyrazole-4-carbonyl)-6-chloro-5-fluorospiro[benzo[d][1,3]oxazine-4,3'-piperidin]-2(1H)-one, (R)-1'-(5-Amino-1-(bicyclo[1.1.1]pentan-1-yl)-1H-pyrazole-4-carbonyl)-6-chloro-5-fluorospiro[benzo[d][1,3]oxazine-4,3'-piperidin]-2(1H)-one, (R)-1'-(5-Amino-1-(2-(2,2,2-trifluoroethoxy)ethyl)-1H-pyrazole-4-carbonyl)-6-chloro-5-fluorospiro[benzo[d][1,3]oxazine-4,3'-piperidin-2 (1H)-one, (R)-1'-(5-Amino-1-(2-isopropoxyethyl)-1H-pyrazole-4-carbonyl)-6-chloro-5-fluorospiro[benzo[d][1,3]oxazine-4,3'-piperidin]-2(1H)-one, (R)-1'-(5-Amino-1-cyclopentyl-1H-pyrazole-4-carbonyl)-6-chloro-5-fluorospiro[benzo[d][1,3]oxazine-4,3'-piperidin]-2(1H)-one, (R)-1'-(5-Amino-1-(tert-butyl)-1H-pyrazole-4-carbonyl)-6-chloro-5-fluorospiro[benzo[d][1,3]oxazine-4,3'-piperidin]-2(1H)-one, (R)-1'-(5-Amino-1-(2-methoxyethyl)-1H-pyrazole-4-carbonyl)-6-chloro-5-fluorospiro[benzo[d][1,3]oxazine-4,3'-piperidin]-2(1H)-one, (R)-1'-(5-Amino-1-ethyl-1-1H-pyrazole-4-carbonyl)-6-chloro-5-fluorospiro[benzo[d][1,3]oxazine-4,3'-piperidin]-2(1H)-one, (R)-1'-(5-Amino-1-((1-(trifluoromethyl)cyclopropyl)methyl)-1H-pyrazole-4-carbonyl)-6-chloro-5-fluorospiro[benzo[d][1,3]oxazine-4,3'-piperidin]-2(1H)-one, (R)-1'-(5-Amino-1-(3,3,3-trifluoropropyl)-1H-pyrazole-4-carbonyl)-6-chloro-5-fluorospiro[benzo[d][1,3]oxazine-4,3'-piperidin]-2(1H)-one, (R)-1'-(5-Amino-1-(1-(4-fluorophenyl)cyclopropyl)-1H-pyrazole-4-carbonyl)-6-chloro-5-fluorospiro[benzo[d][1,3]oxazine-4,3'-piperidin]-2(1H)-one, (R)-1'-(5-Amino-1-((1-fluorocyclopropyl)methyl)-1H-pyrazole-4-carbonyl)-6-chloro-5-fluorospiro[benzo[d][1,3]oxazine-4,3'-piperidin]-2(1H)-one, (R)-1'-(5-Amino-1-(4-methyl-5-phenyl-4H-1,2,4-triazol-3-yl)-1H-pyrazole-4-carbonyl)-6-chloro-5-fluorospiro[benzo[d][1,3]oxazine-4,3'-piperidin]-2(1H)-one, (R)-1'-(5-Amino-1-(pyridin-3-ylmethyl)-1H-pyrazole-4-carbonyl)-6-chloro-5-fluorospiro[benzo[d][1,3]oxazine-4,3'-piperidin]-2(1H)-one, (R)-1'-(5-Amino-1-(pyridin-4-ylmethyl)-1H-pyrazole-4-carbonyl)-6-chloro-5-fluorospiro[benzo[d][1,3]oxazine-4,3'-piperidin]-2(1H)-one, (R)-1'-(5-Amino-1-(3,4-difluorobenzyl)-1H-pyrazole-4-carbonyl)-6-chloro-5-fluorospiro[benzo[d][1,3]oxazine-4,3'-piperidin]-2(1H)-one, (R)-1'-(5-Amino-1-isopropyl-1H-pyrazole-4-carbonyl)-6-chloro-5-fluorospiro[benzo[d][1,3]oxazine-4,3'-piperidin]-2(1H)-one, (R)-1'-(5-Amino-1-cyclohexyl-1H-pyrazole-4-carbonyl)-6-chloro-5-fluorospiro[benzo[d][1,3]oxazine-4,3'-piperidin-2-(1H)-one, (R)-1'-(5-Amino-1-(cyclohexylmethyl)-1H-pyrazole-4-carbonyl)-6-chloro-5-fluorospiro[benzo[d][1,3]oxazine-4,3'-piperidin]-2(1H)-one, (R)-1'-(5-Amino-1-(2-(4-chlorophenoxy)ethyl)-1H-pyrazole-4-carbonyl-6-chloro-5-fluorospiro[benzo[d][1,3]oxazine-4,3'-piperidin]-2(1H)-one, (R)-1'-(5-Amino-1-(2,3-dihydro-1H-inden-2-yl)-1H-pyrazole-4-carbonyl)-6-chloro-5-fluorospiro[benzo[d][1,3]oxazine-4,3'-piperidin]-2(1H)-one, (R)-1'-5-Amino-1-(3-methoxybenzyl)-1H-pyrazole]-carbonyl)-6-chloro-5-fluorospiro[benzo[d][1,3]oxazine-4,3'-piperidin]-2(1H)-one, (R)-1'-(5-Amino-1-(2-methoxybenzyl-1H-pyrazole-4-carbonyl-6-chloro-5-fluorospiro[benzo[d][1,3]oxazine-4,3'-piperidin]-2(1H)-one, (R)-1'-(5-Amino-1-(2-(dimethylamino)benzyl)-1H-pyrazole-4-carbonyl)-6-chloro-5-fluorospiro[benzo[d][1,3]oxazine-4,3'-piperidin]-2(1H)-one, (R)-1'-(5-Amino-1-(4-chlorobenzyl)-1H-pyrazole-4-carbonyl)-6-chloro-5-fluorospiro[benzo[d][1,3]oxazine-4,3'-piperidin]-2(1H)-one, (R)-1'-(5-Amino-1-((6-(trifluoromethyl)pyridin-3-yl)methyl)-1H-pyrazole-4-carbonyl)-6-chloro-5-fluorospiro[benzo[d][1,3]oxazine-4,3'-piperidin]-2(1H)-one, (R)-1'-(5-Amino-1-(2-chlorobenzyl)-1H-pyrazole-4-carbonyl)-6-chloro-5-fluorospiro[benzo[d][1,3]oxazine-4,3'-piperidin]-2(1H)-one, (R)-1'-(5-Amino-1-(3-methylbenzyl)-1H-pyrazole-4-carbonyl)-6-chloro-5-fluorospiro[benzo[d][1,3]oxazine-4,3'-piperidin]-2(1H)-one, (R)-1'-(5-Amino-1-(1-(4-fluorophenyl)cyclobutyl)-1H-pyrazole-4-carbonyl)-6-chloro-5-fluorospiro[benzo[d][1,3]oxazine-4,3'-piperidin]-2(1H)-one, (R)-1'-(5-Amino-1-(1-(trifluoromethyl)cyclobutyl)-1H-pyrazole-4-carbonyl)-6-chloro-5-fluorospiro[benzo[d][1,3]oxazine-4,3'-piperidin]-2(1H)-one, (R)-1'-(5-Amino-1-(2,2,3,3,3-pentafluoropropyl-1H-pyrazole-4-carbonyl)-6-chloro-5-fluorospiro[benzo[d][1,3]oxazine-4,3'-piperidin]-2(1H)-one, (R)-1'-(5-Amino-1-(1,1,1-trifluoro-2-methylpropan-2-yl)-1H-pyrazole-4-carbonyl)-6-chloro-5-fluorospiro[benzo[d][1,3]oxazine-4,3'-piperidin]-2(1H)-one, (R)-1'-(5-Amino-1-(1-(trifluoromethyl)cyclopropyl)-1H-pyrazole-4-carbonyl)-6-chloro-5-fluorospiro[benzo[d][1,3]oxazine-4,3'-piperidin]-2-(1H)-one, (R)-1'-(5-Amino-1-(pyrimidin-5-ylmethyl)-1H-pyrazole-4-carbonyl)-6-chloro-5-fluorospiro[benzo[d][1,3]oxazine-4,3'-piperidin]-2(1H)-one, (R)-1'-(5-Amino-1-(3,3-difluoro-1-(trifluoromethyl)cyclobutyl)-1H-pyrazole-4-carbonyl)-6-chloro-5-fluorospiro[benzo[d][1,3]oxazine-4,3-piperidin]-2(1H)-one, (R)-1'-(5-Amino-1-(4-(trifluoromethyl)tetrahydro-2H-pyran-4-yl)-1H-pyrazole-4-carbonyl)-6-chloro-5-fluorospiro[benzo[d][1,3]oxazine-4,3'-piperidin]-2(1H)-one, (R)-1'-(5-Amino-1-(pyrazin-2-ylmethyl)-1H-pyrazole-4-carbonyl)-6-chloro-5-fluorospiro[benzo[d][1,3]oxazine-4,3'-piperidin]-2(1H)-one, (R)-1'-(5-Amino-1-(pyridin-3-ylmethyl)-1H-pyrazole-4-carbonyl)-6-chloro-5-fluorospiro[benzo[d][1,3]oxazine-4,3'-piperidin]-2(1H)-one, (R)-1'-(5-Amino-1-((1S,2S or R,5R)-2-(trifluoromethyl)bicyclo[3.1.0]hexan-2-yl)-1H-pyrazole-4-carbonyl)-6-chloro-5-fluorospiro[benzo[d][1,3]oxazine-4,3'-piperidin]-2(1H)-one, (R)-1'-(5-Amino-1-phenyl-1H-pyrazole-4-carbonyl)-6-chloro-5-fluorospiro[benzo[d][1,3]oxazine-4,3'-piperidin]-2(1H)-one, (R)-1'-(5-Amino-1-(4-methoxyphenyl)-1H-pyrazole-4-carbonyl)-6-chloro-5-fluorospiro[benzo[d][1,3]oxazine-4,3'-piperidin]-2(1H)-one, (R)-1'-(5-Amino-1-(1H-indazol-6-yl)-1H-pyrazole-4-carbonyl)-6-chloro-5-fluorospiro[benzo[d][1,3]oxazine-4,3'-piperidin]-2(1H)-one, (R)-1'-(5-Amino-1-(6-fluoroquinolin-4-yl)-1H-pyrazole-4-carbonyl)-6-chloro-5-fluorospiro[benzo[d][1,3]oxazine-4,3'-piperidin]-2(1H)-one, (R)-1'-(5-Amino-1-(2-methylpyridin-3-yl)-1H-pyrazole-4-carbonyl)-6-chloro-5-fluorospiro[benzo[d][1,3]oxazine-4,3'-piperidin]-2(1H)-one, (R)-1'-(5-Amino-1-(3-fluoropyridin-2-yl)-1-pyrazole-4-carbonyl)-6-chloro-5-fluorospiro[benzo[d][1,3]oxazine-4,3'-piperidin]-2(1H)-one, (R)-1'-(5-Amino-1-(3-(hydroxymethyl)-2-methylphenyl)-1H-pyrazole-4-carbonyl)-6-chloro-5-fluorospiro[benzo[d][1,3]oxazine-4,3'-piperidin-2(1H)-one, (R)-1'-(5-Amino-1-(o-tolyl)-1H-pyrazole-4-carbonyl)-6-chloro-5-fluorospiro[benzo[d][1,3]oxazine-4,3'-piperidin]-2(1H)-one, (R)-1'-(5-Amino-1-(2,4-dichlorophenyl)-1H-pyrazole-4-carbonyl)-6-chloro-5-fluorospiro[benzo[d][1,3]oxazine-4,3'-piperidin-2-(1H)-one, (R)-1'-(5-Amino-1-(2-fluoro-4-methylphenyl)-1H-pyrazole-4-carbonyl)-6-chloro-5-fluorospiro[benzo[d][1,3]oxazine-4,3'-piperidin]-2(1H)-one, (R)—N-(4-(5-Amino-4-(6-chloro-5-fluoro-2-oxo-1,2-dihydrospiro[benzo[d][1,3]oxazine-4,3'-piperidine]-1'-carbonyl)-1H-pyrazol-1-yl)phenyl)acetamide, (R)-3-(5-Amino-4-(6-chloro-5-fluoro-2-oxo-1,2-dihydrospiro[benzo[d][1,3]oxazine-4,3'-piperidine]-1'-carbonyl)-1H-pyrazol-1-yl)benzoic acid, (R)-1'-(5-Amino-1-phenyl-1H-pyrazole-4-carbonyl)-6-chloro-5-fluoro-5',5'-dimethylspiro[benzo[d][1,3]oxazine-4,3'-piperidin]-2(1H)-one, Ethyl (R)-3-(5-amino-4-(6-chloro-5-fluoro-2-oxo-1,2-dihydrospiro[benzo[d][1,3]oxazine-4,3'-piperidine]-1'-carbonyl)-1H-pyrazol-1-yl)-4-methylbenzoate, (R)—N-(3-(5-Amino-4-(6-chloro-5-fluoro-2-oxo-1,2-dihydrospiro[benzo[d][1,3]oxazine-4,3'-piperidine]-1'-carbonyl)-1H-pyrazol-1-yl)phenyl)acetamide, (R)-1'-(5-Amino-1-(2-(trifluoromethoxy)phenyl)-1H-pyrazole-4-carbonyl)-6-chloro-5-fluorospiro[benzo[d][1,3]oxazine-4,3'-piperidin]-2(1H)-one, (R)-1'-(5-Amino-1-(3-chloropyridin-4-yl)-1H-pyrazole-4-carbonyl)-6-chloro-5-fluorospiro[benzo[d][1,3]oxazine-4,3'-piperidin]-2(1H)-one, (R)-4-(5-Amino-4-(6-chloro-5-fluoro-2-oxo-1,2-dihydrospiro[benzo[d][1,3]oxazine-4,3'-piperidine]-1'-carbonyl)-1H-pyrazol-1-yl)benzoic acid, (R)-1'-(5-Amino-1-(4-(2-oxooxazolidin-3-yl)phenyl-1H-pyrazole-4-carbonyl)-6-chloro-5-fluorospiro[benzo[d][1,3]oxazine-4,3'-piperidin]-2(1H)-one, (R)-1'-(5-Amino-1-(2,5-difluorophenyl)-1H-pyrazole-4-carbonyl)-6-chloro-5-fluorospiro[benzo[d][1,3]oxazine-4,3'-piperidin]-2(1H)-one, (R)-1'-(5-Amino-1-(2-(trifluoromethyl)phenyl)-1H-pyrazole-4-carbonyl)-6-chloro-5-fluorospiro[benzo[d][1,3]oxazine-4,3'-piperidin]-2(1H)-one, (R)-1'-(5-Amino-1-(2-chloro-5-fluorophenyl)-1H-pyrazole-4-carbonyl)-6-chloro-5-fluorospiro[benzo[d][1,3]oxazine-4,3'-piperidin-2(1H)-one, (R)-1'-(5-Amino-1-(2-methoxyphenyl)-1H-pyrazole-4-carbonyl)-6-chloro-5-fluorospiro[benzo[d][1,3]oxazine-4,3'-piperidin]-2(1H)-one, (R)-1'-(5-Amino-1-(2-ethylphenyl)-1H-pyrazole-4-carbonyl)-6-chloro-5-fluorospiro[benzo[d][1,3]oxazine-4,3'-piperidin-2-(1H)-one, (R)-1'-(5-Amino-1-(2-isopropylphenyl)-1H-pyrazole-4-carbonyl)-6-chloro-5-fluorospiro[benzo[d][1,3]oxazine-4,3'-piperidin]-2(1H)-one, (R)-1'-(5-Amino-1-(2-chlorophenyl)-1H-pyrazole-4-carbonyl)-6-chloro-5-fluorospiro[benzo[d][1,3]oxazine-4,3'-piperidin]-2(1H)-one, (R)-1'-(5-Amino-1-(2-bromophenyl)-1H-pyrazole-4-carbonyl)-6-chloro-5-fluorospiro[benzo[d][1,3]oxazine-4,3'-piperidin]-2(1H)-one, (R)-1'-(5-Amino-1-(2-fluorophenyl)-1H-pyrazole-4-carbonyl)-6-chloro-5-fluorospiro[benzo[d][1,3]oxazine-4,3'-piperidin]-2(1H)-one, (R)-1'-(5-Amino-1-(2,3-dimethylphenyl)-1H-pyrazole-4-carbonyl)-6-chloro-5-fluorospiro[benzo[d][1,3]oxazine-4,3'-piperidin]-2(1H)-one, (R)-1'-(5-Amino-1-(2,4-dimethylphenyl)-1H-pyrazole-4-carbonyl)-6-chloro-5-fluorospiro[benzo[d][1,3]oxazine-4,3'-piperidin]-2(1H)-one, (R)-1'-(5-Amino-1-(2,5-dimethylphenyl)-1H-pyrazole-4-carbonyl)-6-chloro-5-fluorospiro[benzo[d][1,3]oxazine-4,3'-piperidin]-2(1H)-one, (R)-1'-(5-Amino-1-(5-fluoro-2-methylphenyl)-1H-pyrazole-4-carbonyl)-6-chloro-5-fluorospiro[benzo[d][1,3]oxazine-4,3'-piperidin]-2(1H)-one, (R)-1'-(5-Amino-1-(2-cyclopropoxyphenyl)-1H-pyrazole-4-carbonyl)-6-chloro-5-fluorospiro[benzo[d][1,3]oxazine-4,3'-piperidin]-2(1H)-one, (R)-1'-(5-Amino-1-(2-(difluoromethoxy)phenyl)-1H-pyrazole-4-carbonyl)-6-chloro-5-fluorospiro[benzo[d][1,3]oxazine-4,3'-piperidin]-2(1H)-one, (R)-1'-(5-Amino-1-(2,2-difluorobenzo[d][1,3]dioxol-4-yl)-1H-pyrazole-4-carbonyl)-6-chloro-5-fluorospiro[benzo[d][1,3]oxazine-4,3'-piperidin-2(1H)-one, Methyl (R)-4-(S-amino-4-(6-chloro-5-fluoro-2-oxo-1,2-dihydrospiro[benzo[d][1,3]oxazine-4,3'-piperidine]-1'-carbonyl)-1H-pyrazol-1-yl)-3-methoxybenzoate, (R)-1'-(5-Amino-1-(2,6-difluorophenyl)-1H-pyrazole-4-carbonyl)-6-chloro-5-fluorospiro[benzo[d][1,3]oxazine-4,3'-piperidin]-2(1H)-one, (R)-1'-(5-Amino-1-(5-chloro-2-methoxyphenyl)-1H-pyrazole-4-carbonyl)-6-chloro-5-fluorospiro[benzo[d][1,3]oxazine-4,3'-piperidin]-2(1H)-one, (R)-1'-(5-Amino-1-(2-cyclopropylphenyl)-1H-pyrazole-4-carbonyl)-6-chloro-5-fluorospiro[benzo[d][1,3]oxazine-4,3'-piperidin-2-(1H)-one, (R)-1'-(5-Amino-1-(2-phenoxyphenyl)-1H-pyrazole-4-carbonyl)-6-chloro-5-fluorospiro[benzo[d][1,3]oxazine-4,3'-piperidin]-2(1H)-one, (R)-1'-(5-Amino-1-(2-cyclobutoxyphenyl)-1H-pyrazole-4-carbonyl)-6-chloro-5-fluorospiro[benzo[d][1,3]oxazine-4,3'-piperidin]-2(1H)-one, (R)-1'-(5-Amino-1-(2-(1-methylcyclopropyl)phenyl)-1H-pyrazole-4-carbonyl)-6-chloro-5-fluorospiro[benzo[d][1,3]oxazine-4,3'-piperidin]-2(1H)-one, (R)-1'-(5-Amino-1-(2-(2,2,2-trifluoroethoxy)phenyl)-1H-pyrazole]-carbonyl)-6-chloro-5-fluorospiro[benzo[d][1,3]oxazine-4,3'-piperidin]-2(1H)-one, (R)-1'-(5-Amino-1-(4-fluoro-2-methoxyphenyl)-1H-pyrazole-4-carbonyl)6-chloro-5-fluorospiro[benzo[d][1,3]oxazine-4,3'-piperidin]-2(1H)-one, (R)-1'-(5-Amino-1-(3,5-difluoro-2-methoxyphenyl)-1H-pyrazole-4-carbonyl)-6-chloro-5-fluorospiro[benzo[d][1,3]oxazine-4,3'-piperidin]-2(1H)-one, (R)-1'-(5-Amino-1-(3,5-dichloropyridin-4-yl)-1H-pyrazole-4-carbonyl)-6-chloro-5-fluorospiro[benzo[d][1,3]oxazine-4,3'-piperidin]-2(1H)-one, (R)-1'-(5-Amino-1-(quinolin-4-yl)-1H-pyrazole-4-carbonyl)-6-chloro-5-fluorospiro[benzo[d][1,3]oxazine-4,3'-piperidin]-2(1H)-one, (R)-1'-(5-Amino-1-(8-fluoroquinolin-4-yl) 1H-pyrazole-4-carbonyl)-6-chloro-5-fluorospiro[benzo[d][1,3]oxazine-4,3'-piperidin]-2(1H)-one, (R)-1'-(5-Amino-1-(3-methylpyridin-4-yl)-1H-pyrazole-4-carbonyl)-6-chloro-5-fluorospiro[benzo[d][1,3]oxazine-4,3'-piperidin]-2(1H)-one, (R)-1'-(5-Amino-1-(2-difluoromethoxy)-5-fluorophenyl)-1H-pyrazole-4-carbonyl)-6-chloro-5-fluorospiro[benzo[d][1,3]oxazine-4,3'-piperidin]-2(1H)-one, (R)-1'-(5-Amino-1-(2-(difluoromethoxy)-3-fluorophenyl)-1H-pyrazole-4-carbonyl)-6-chloro-5-fluorospiro[benzo[d][1,3]oxazine-4,3'-piperidin]-2(1H)-one, (R)-1'-(5-Amino-1-(3-methoxypyridin-2-yl)-1H-pyrazole-carbonyl)-6-chloro-5-fluorospiro[benzo[d][1,3]oxazine-4,3'-piperidin]-2(1H)-one, (R)-1'-(5-Amino-1-methyl-1H-pyrazole-4-carbonyl)-6-chloro-5-fluorospiro[benzo[d][1,3]oxazine-4,3'-piperidin]-2(1H)-one, (R)-1'-(5-Amino-1-(3-chlorophenyl)-1H-pyrazole-4-carbonyl)-6-chloro-5-fluorospiro[benzo[d][1,3]oxazine-4,3'-piperidin]-2-(1H)-one, (R)-1'-(5-Amino-1-(p-tolyl)-1H-pyrazole-4-carbonyl)-6-chloro-5-fluorospiro[benzo[d][1,3]oxazine-4,3'-piperidin]-2(1H)-one, (R)-1'-(5-Amino-1-((R or S)-1-(tetrahydro-2H-pyran-4-yl)propyl)-1H-pyrazole-4-carbonyl)-6-chloro-5-fluorospiro[benzo[d][1,3]oxazine-4,3'-piperidin]-2(1H)-one, (R)-1'-(5-Amino-1-((S or R)-1-(tetrahydro-2H-pyran-4-yl)propyl)-1H-pyrazole-4-carbonyl)-6-chloro-5-fluorospiro[benzo[d][1,3]oxazine-4,3'-piperidin]-2(1H)-one, (R)-1'-(5-Amino-1-((R or S)-2,2,2-trifluoro-1-(1-fluorocyclopropyl)ethyl)-1H-pyrazole-4-carbonyl)-6-chloro-5-fluorospiro[benzo[d][1,3]oxazine-4,3'-piperidin]-2(1H)-one, (R)-1'-(5-Amino-1-((S or R)-2,2,2-trifluoro-1-(1-fluorocyclopropyl)ethyl)-1H-pyrazole-4-carbonyl)-6-chloro-5-fluorospiro[benzo[d][1,3]oxazine-4,3'-piperidin]-2(1H)-one, (R)-1'-(5-Amino-1-((S or R)-1-phenylpropyl)-1H-pyrazole-4-carbonyl)-6-chloro-5-fluorospiro[benzo[d][1,3]oxazine-4,3'-piperidin]-2(1H)-one, (R)-1'-(5-Amino-1-((R or S)-1-phenylpropyl)-1H-pyrazole-4-carbonyl)-6-chloro-5-fluorospiro[benzo[d][1,3]oxazine-4,3'-piperidin]-2(1H)-one, (R)-1'-(5-Amino-1-((R or S)-3-methyl-1,1-dioxidotetrahydrothiophen-3-yl)-1H-pyrazole-4-carbonyl)-6-chloro-5-fluorospiro[benzo[d][1,3]oxazine-4,3'-piperidin]-2(1H)-one, (R)-1'-(5-Amino-1-((S or R)-3-methyl-1,1-dioxidotetrahydrothiophen-3-yl)-1H-pyrazole-4-carbonyl)-6-chloro-5-fluorospiro[benzo[d][1,3]oxazine-4,3'-piperidin-2(1H)-one, (R)-1'-(5-Amino-1-((R or S)-1,1,1-trifluoropropan-2-yl)-1H-pyrazole-4-carbonyl)-6-chloro-5-fluorospiro[benzo[d][1,3]oxazine-4,3'-piperidin]-2(1H)-one, (R)-1'-(5-Amino-1-((S or R)-1,1,1-trifluoropropan-2-yl)-1H-pyrazole-4-carbonyl)-6-chloro-5-fluorospiro[benzo[d][1,3]oxazine-4,3'-piperidin]-2(1H)-one, (R)-1'-(5-Amino-1-((R or S)-2,2,2-trifluoro-1-phenylethyl)-1H-pyrazole-4-carbonyl)-6-chloro-5-fluorospiro[benzo[d][1,3]oxazine-4,3'-piperidin]-2(1H)-one, (R)-1'-(5-Amino-1-((S or R)-2,2,2-trifluoro-1-phenylethyl)-1H-pyrazole-4-carbonyl)-6-chloro-5-fluorospiro[benzo[d][1,3]oxazine-4,3'-piperidin]-2(1H)-one, (R)-1'-(5-Amino-1-((R or S)-1-cyclopropyl-2,2,2-trifluoroethyl)-1H-pyrazole-4-carbonyl)-6-chloro-5-fluorospiro[benzo[d][1,3]oxazine-4,3'-piperidin]-2(1H)-one, (R)-1'-(5-Amino-1-((S or R)-1-cyclopropyl-2,2,2-trifluoroethyl)-1H-pyrazole-4-carbonyl)-6-chloro-5-fluorospiro[benzo[d][1,3]oxazine-4,3'-piperidin]-2-(1H)-one, (R)-1'-(5-Amino-1-((R or S)-2-cyclopropyl-1,1,1-trifluoropropan-2-yl)-1H-pyrazole-4-carbonyl)-6-chloro-S-fluorospiro[benzo[d][1,3]oxazine-4,3'-piperidin]-2(1H)-one, (R)-1'-(5-Amino-1-((S or R)-2-cyclopropyl-1,1,1-trifluoropropan-2-yl)-1H-pyrazole-4-carbonyl)-6-chloro-5-fluorospiro[benzo[d][1,3]oxazine-4,3'-piperidin]-2(1H)-one, (R)-1'-(5-Amino-1-((R or S)-1,1,1-trifluoro-3-methoxy-2-methylpropan-2-yl)-1H-pyrazole-4-carbonyl)-6-chloro-5-fluorospiro[benzo[d][1,3]oxazine-4,3'-piperidin]-2(1H)-one, (R)-1'-(5-Amino-1-((S or R)-1,1,1-trifluoro-3-methoxy-2-methylpropan-2-yl)-1H-pyrazole-4-carbonyl)-6-chloro-5-fluorospiro[benzo[d][1,3]oxazine-4,3'-piperidin]-2(1H)-one, (R)-1'-(5-Amino-1-((R or S)-1,1,1-trifluorobutan-2-yl)-1H-pyrazole-4-carbonyl)-6-chloro-5-fluoro-5',5'-dimethylspiro[benzo[d][1,3]oxazine-4,3'-piperidin]-2(1H)-one, (R)-1'-(5-Amino-1-((S or R)-1,1,1-trifluorobutan-2-yl)-1H-pyrazole-4-carbonyl)-6-chloro-5-fluoro-5',5'-dimethylspiro[benzo[d][1,3]oxazine-4,3'-piperidin]-2(1H)-one, (R)-6-Chloro-5-fluoro-1'-1-(4-fluorobenzyl)-5-hydroxy-1H-pyrazole-4-carbonyl)spiro[benzo[d][1,3]oxazine-4,3'-piperidin]-2(1H)-one, and (R)-1'-(5-Amino-1-benzyl-1H-1,2,3-triazole-4-carbonyl)-6-chloro-5-fluorospiro[benzo[d][1,3]oxazine-4,3'-piperidin]-2(1H)-one, or a pharmaceutically acceptable salt thereof.

10. A pharmaceutical composition comprising a compound of claim 1 or a pharmaceutically acceptable salt thereof and a pharmaceutically acceptable carrier.

11. A method for treating uveitis, posterior uveitis, wet age related macular edema, diabetic macular edema, diabetic retinopathy or retinal vein occlusion in a mammal comprising administering a composition of claim 10 to a mammal in need thereof.

12. A method of treating diabetic retinopathy or diabetic macular edema in a mammal comprising administering a composition of claim 10 to a mammal in need thereof.

13. A method of treating retinal vein occlusion in a mammal comprising administering a composition of claim 10 to a mammal in need thereof.

14. The composition of claim 10 further comprising another agent selected from the group consisting of anti-inflammatory agents, anti-VEGF agents, immunosuppressive agents, anticoagulants, antiplatelet agents, and thrombolytic agents.

15. A method for treating impaired visual activity, diabetic retinopathy, diabetic macular edema, retinal vein occlusion, hereditary angioedema, diabetes, pancreatitis, cerebral hemorrhage, or nephropathy, comprising administering a composition of claim 10 to a mammal in need of thereof.

16. The method of claim 15 further comprising another agent selected from the group consisting of anti-inflammatory agents, anti-VEGF agents, immunosuppressive agents, anticoagulants, antiplatelet agents, and thrombolytic agents.

* * * * *